(12) United States Patent
Obata et al.

(10) Patent No.: US 7,534,539 B2
(45) Date of Patent: May 19, 2009

(54) ELECTROPHOTOGRAPHIC PHOTORECEPTOR AND IMAGE FORMING APPARATUS HAVING THE SAME

(75) Inventors: Takatsugu Obata, Nara (JP); Akihiro Kondoh, Nara (JP); Kazuya Ishida, Kyoto (JP)

(73) Assignee: Sharp Kabushiki Kaisha, Osaka (JP)

( * ) Notice: Subject to any disclaimer, the term of this patent is extended or adjusted under 35 U.S.C. 154(b) by 418 days.

(21) Appl. No.: 10/559,187

(22) PCT Filed: May 31, 2004

(86) PCT No.: PCT/JP2004/007484

§ 371 (c)(1),
(2), (4) Date: Dec. 1, 2005

(87) PCT Pub. No.: WO2004/109406

PCT Pub. Date: Dec. 16, 2004

(65) Prior Publication Data

US 2006/0210895 A1    Sep. 21, 2006

(30) Foreign Application Priority Data

Jun. 3, 2003 (JP) .............................. 2003-157688

(51) Int. Cl.
*G03G 5/047* (2006.01)
(52) U.S. Cl. ..................................... 430/72; 430/58.85
(58) Field of Classification Search .............. 430/58.85, 430/72
See application file for complete search history.

(56) References Cited

U.S. PATENT DOCUMENTS

| | | | |
|---|---|---|---|
| 3,824,099 A | 7/1974 | Champ et al. | |
| 4,123,269 A | 10/1978 | Von Hoene et al. | |
| 4,150,987 A | 4/1979 | Anderson et al. | |
| 4,278,747 A | 7/1981 | Murayama et al. | |
| 4,338,388 A | 7/1982 | Sakai et al. | |
| 4,367,273 A | 1/1983 | Murayama et al. | |

(Continued)

FOREIGN PATENT DOCUMENTS

CN          1151536 A       6/1997

(Continued)

OTHER PUBLICATIONS

English language translation of JP 2002-365820, Dec. 18, 2002.*

(Continued)

*Primary Examiner*—Mark F Huff
*Assistant Examiner*—Rachel L Burney
(74) *Attorney, Agent, or Firm*—Nixon & Vanderhye P.C.

(57) ABSTRACT

An object of the invention is to provide a highly reliable electrophotographic photoreceptor having high sensitivity, excellent in light responsivity, not suffering from lowering of such characteristics even when it is used under a low temperature circumstance or in a high speed electrophotographic process, and with less fatigue degradation upon repetitive use. In a photosensitive layer of an electrophotoreceptor, an enamine compound represented by the following general formula (1), for example, the following structural formula is contained as a charge transporting substance, and further at least one of an antioxidant and a light stabilizer is contained. Accordingly, an electrophotographic photoreceptor excellent in sensitivity and light responsivity in various environments, and with less fatigue degradation upon repetitive use is realized.

7 Claims, 15 Drawing Sheets

U.S. PATENT DOCUMENTS

| | | | |
|---|---|---|---|
| 4,471,039 | A | 9/1984 | Borsenberger et al. |
| 4,522,483 | A | 6/1985 | Matsumoto |
| 4,557,868 | A | 12/1985 | Page et al. |
| 4,637,971 | A | 1/1987 | Takei |
| 4,724,194 | A | 2/1988 | Shirai |
| 4,725,519 | A | 2/1988 | Suzuki et al. |
| 4,851,960 | A | 7/1989 | Nakamura |
| 4,859,556 | A | 8/1989 | Sasaki |
| 4,892,949 | A | 1/1990 | Sasaki |
| 4,898,799 | A | 2/1990 | Fujimaki et al. |
| 4,971,877 | A | 11/1990 | Miyamoto et al. |
| 4,981,767 | A | 1/1991 | Tokura et al. |
| RE33,724 | E | 10/1991 | Takei |
| 5,106,536 | A | 4/1992 | Miyamoto et al. |
| 5,126,913 | A | 6/1992 | Araya |
| 5,132,197 | A | 7/1992 | Iuchi et al. |
| 5,250,990 | A | 10/1993 | Fujimura |
| 5,292,604 | A | 3/1994 | Nukada et al. |
| 5,430,526 | A | 7/1995 | Ohkubo |
| 5,492,786 | A | 2/1996 | Sugimura |
| 5,595,846 | A | 1/1997 | Shigematsu et al. |
| 5,618,646 | A | 4/1997 | Nogami et al. |
| RE35,581 | E | 8/1997 | Nakamura |
| 5,876,890 | A | 3/1999 | Kitamura |
| 5,900,342 | A | 5/1999 | Visser |
| 6,117,603 | A | 9/2000 | Yu |
| 6,150,063 | A | 11/2000 | Sugimura et al. |
| 6,171,742 | B1 | 1/2001 | Kawada |
| 6,178,303 | B1 | 1/2001 | Ishii |
| 6,210,847 | B1 | 4/2001 | Miyauchi et al. |
| 6,270,936 | B1 | 8/2001 | Tanaka |
| 6,485,658 | B1 | 11/2002 | Horiuchi et al. |
| 6,489,072 | B2 | 12/2002 | Sasaki |
| 6,852,462 | B2 | 2/2005 | Emoto |
| 6,879,794 | B2 | 4/2005 | Azuma |
| 7,074,531 | B2 | 7/2006 | Fukushima |
| 7,157,199 | B2 | 1/2007 | Emoto |
| 7,175,956 | B2 | 2/2007 | Obata |
| 2002/0045116 | A1 | 4/2002 | Morikawa et al. |
| 2003/0021612 | A1 | 1/2003 | Morikawa et al. |
| 2003/0054271 | A1* | 3/2003 | Yao et al. .................. 430/66 |
| 2003/0138718 | A1 | 7/2003 | Yagi |
| 2004/0101770 | A1 | 5/2004 | Obata et al. |
| 2004/0142258 | A1 | 7/2004 | Fukushima |
| 2005/0232657 | A1* | 10/2005 | Fujii et al. ............... 399/159 |

FOREIGN PATENT DOCUMENTS

| | | |
|---|---|---|
| JP | 52-4188 | 2/1977 |
| JP | 54-150128 A | 11/1979 |
| JP | 54-151955 A | 11/1979 |
| JP | 55-52063 A | 4/1980 |
| JP | 55-42380 B2 | 10/1980 |
| JP | 58-49960 | 3/1983 |
| JP | 58-32372 B2 | 7/1983 |
| JP | 58-198043 A | 11/1983 |
| JP | 59-155851 A | 9/1984 |
| JP | 60-022131 | 2/1985 |
| JP | 60-172045 | 9/1985 |
| JP | 61-28557 A | 2/1986 |
| JP | 61-062040 | 3/1986 |
| JP | 61-109056 | 5/1986 |
| JP | 63-085581 | 4/1988 |
| JP | 63-149669 | 6/1988 |
| JP | 63-170673 | 7/1988 |
| JP | 64-44946 A | 2/1989 |
| JP | 64-73365 | 3/1989 |
| JP | 1-142658 A | 6/1989 |
| JP | 1-142659 A | 6/1989 |
| JP | 1-172857 | 7/1989 |
| JP | 02-008256 | 1/1990 |
| JP | 2-51162 A | 2/1990 |
| JP | 2-84661 A | 3/1990 |
| JP | 2-170166 A | 6/1990 |
| JP | 2-190862 A | 7/1990 |
| JP | 2-233769 A | 9/1990 |
| JP | 2-272067 A | 11/1990 |
| JP | 3-20768 | 1/1991 |
| JP | 3-128973 A | 5/1991 |
| JP | 4-78858 A | 3/1992 |
| JP | 4-351673 A | 12/1992 |
| JP | 4-372663 A | 12/1992 |
| JP | 5-61215 | 3/1993 |
| JP | 5-55860 B2 | 8/1993 |
| JP | 6-43674 A | 2/1994 |
| JP | 6-89038 | 3/1994 |
| JP | 6-308744 A | 11/1994 |
| JP | 6-317917 | 11/1994 |
| JP | 7-48324 A | 2/1995 |
| JP | 7-114191 | 5/1995 |
| JP | 7-134430 A | 5/1995 |
| JP | 7-91486 B2 | 10/1995 |
| JP | 07-271073 | 10/1995 |
| JP | 8-67829 A | 3/1996 |
| JP | 8-113636 | 5/1996 |
| JP | 08-185089 | 7/1996 |
| JP | 8-234459 | 9/1996 |
| JP | 9-73182 A | 3/1997 |
| JP | 2700859 B2 | 10/1997 |
| JP | 2730744 B2 | 12/1997 |
| JP | 10-10761 | 1/1998 |
| JP | 10-20517 | 1/1998 |
| JP | 10-69107 A | 3/1998 |
| JP | 10-90926 A | 4/1998 |
| JP | 10-148953 A | 6/1998 |
| JP | 10-268535 | 10/1998 |
| JP | 11-125923 | 5/1999 |
| JP | 11-184110 A | 7/1999 |
| JP | 11-271995 A | 10/1999 |
| JP | 11-311875 | 11/1999 |
| JP | 2000-10320 | 1/2000 |
| JP | 2000-129155 A | 5/2000 |
| JP | 2000-221722 | 8/2000 |
| JP | 2000-313819 A | 11/2000 |
| JP | 2000-338696 A | 12/2000 |
| JP | 2001-33992 A | 2/2001 |
| JP | 2001-51434 A | 2/2001 |
| JP | 2001-56595 | 2/2001 |
| JP | 2001-117246 A | 4/2001 |
| JP | 2001-125298 | 5/2001 |
| JP | 2001-166502 | 6/2001 |
| JP | 2001-215741 | 8/2001 |
| JP | 2002-23396 A | 1/2002 |
| JP | 2002-82465 | 3/2002 |
| JP | 2002-244321 A | 8/2002 |
| JP | 2002-365820 | 12/2002 |
| JP | 2003-5408 | 1/2003 |
| JP | 2003-12619 | 1/2003 |
| JP | 2003-76050 | 3/2003 |
| JP | 2003-107763 A | 4/2003 |
| JP | 2004-151666 A | 5/2004 |
| JP | 2004-205542 | 7/2004 |
| JP | 2004-325686 | 11/2004 |
| JP | 2004-004266 | 1/2008 |

OTHER PUBLICATIONS

English translation of the International Preliminary Report on Patentability mailed May 11, 2006.
International Search Report for PCT/JP2004/007484 dated Sep. 7, 2004.
Chemical Abstracts 138:47243 of JP 2002-365820, 23-28-2002.
Translation of JP2002-365820. cited by Examiner in U.S. Appl. No. 10/653,293.

English Translation of JP 2003-12619 (pub 1-2003) cited by Examiner in U.S. Appl. NO. 11/051,640.

Partial translation of Kitazi et al "Extension of fowe's Formula and Evaluation of Surface Tension of Polymeric Solid" Nippon Sechaku Kyokaishi, Nippon Secchaku Kyokai, 1972, vol. 8, No. 3, pp. 131-141.

English translation of the Int'l. Preliminary Report on Patentability mailed Jun. 29, 2006 in corresponding PCT application PCT/JP2004/014967.

International Preliminary Report on Patentability, mailed March 9, 2006, issued in connection with PCT/JP2004/0005506.

International Preliminary Report on Patentability, mailed Nov. 10, 2005, issued in connection with PCT/JP2004/005506.

International Search Report, mailed Sep. 7, 2004, issued in connection with PCT/JP2004/005506.

International Search Report, mailed Nov. 16, 2004, issued in connection with PCT/JP2004/014967.

JP 2787305, Jun. 1998 (equivalent to JP 63-085581, published Apr. 16, 1988—English Abstract attached).

* cited by examiner

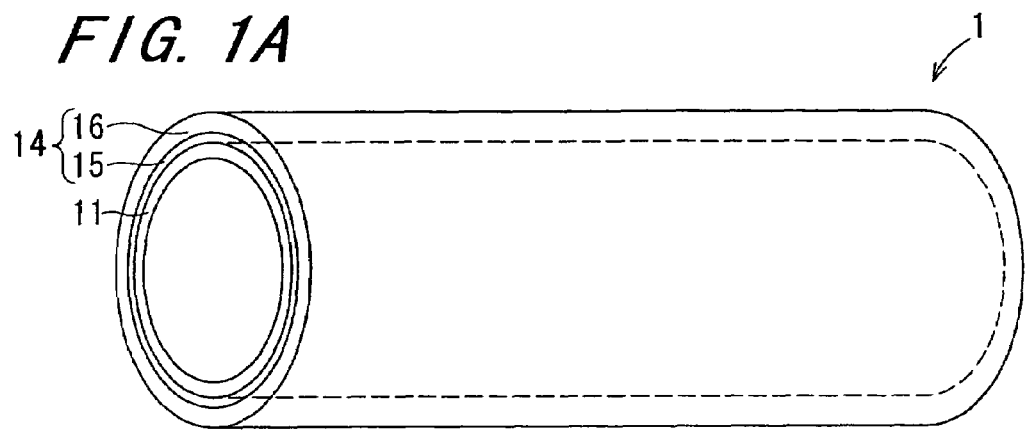
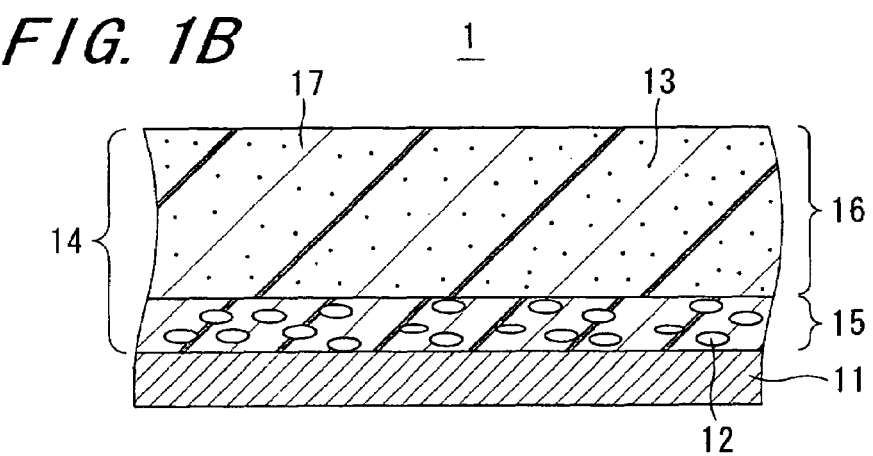

ELECTROPHOTOGRAPHIC PHOTORECEPTOR AND IMAGE FORMING APPARATUS HAVING THE SAME

This application is the US national phase of international application PCT/JP2004/007484 filed 31 May 2004 which designated the U.S. and claims priority to JP 2003-157688 filed 3 Jun. 2003, the entire contents of each of which are hereby incorporated by reference.

TECHNICAL FIELD

The present invention concerns an electrophotographic photoreceptor and an image forming apparatus having the same.

BACKGROUND ART

Electrophotographic image forming apparatus (hereinafter also referred to simply as "electrophotographic apparatus") have been often used, for example, in copying machines, printers, or facsimile units. In the electrophotographic apparatus, images are formed by way of the following electrophotographic process. At first, the surface of an electrophotographic photoreceptor provided to the apparatus (hereinafter also referred to simply as "photoreceptor") is charged to a predetermined potential uniformly by charging means such as a charging roller. Exposure is applied to the surface of the charged photoreceptor in accordance with image information to form electrostatic latent images. The formed electrostatic latent images are developed by a developer containing a toner and the like to form toner images as visible images. The formed toner images are transferred from the surface of the photoreceptor to a recording medium such as paper and transferred toner images are fixed to form images. After the transfer operation, the toner remaining on the surface of the photoreceptor without being transferred is removed by a cleaning blade or the like. Then, the surface charges on the photoreceptor are eliminated by a light from a charge elimination lamp, by which electrostatic latent images are eliminated from the surface of the photoreceptor.

An electrophotographic photoreceptor comprises a conductive substrate made of a conductive material and a photosensitive layer disposed on the conductive substrate. As the electrophotographic photoreceptor, an inorganic photoreceptor having a photosensitive layer comprising an inorganic photoconductive material such as selenium, zinc oxide or cadmium as a main ingredient has been used generally. While the inorganic photoreceptor has basic properties as the photoreceptor to some extent, it involves a problem that the formation of the film for the light sensitive layer is difficult, plasticity is poor, and the production cost is expensive. Further, the inorganic photoconductive material generally has high toxicity and suffers from great restriction in view of production and handling.

On the other hand, since an organic photoreceptor using an organic photoconductive material has advantages that it has good film forming property for a photosensitive layer, excellent flexibility, reduced weight and good transparency and a photoreceptor showing favorable sensitivity to wavelength region over a wide range can be easily designed by an appropriate sensitizing method, it has been gradually developed as a main material for the electrophotographic photoreceptor. While the organic photoreceptor in the initial state has drawback in view of the sensitivity and the durability, such drawbacks have been improved remarkably by the development of a function separated electrophotographic photoreceptor in which a charge generation function and a charge transportation function are shared to separate materials respectively.

The function separated photoreceptor includes a layered type and a single layer type. In the layered type photoreceptor, for example, a photoconductive layer in which a charge generating layer containing a charge generating substance sharing a charge generation function and a charge transporting layer containing a charge transporting substance sharing a charge transportation function are laminated is provided as a photosensitive layer. In the single layer type function separated photoreceptor, a single photoconductive layer containing both a charge generating substance and a charge transporting substance is disposed as a photosensitive layer. The function separated photoreceptor described above also has an advantage that a selection range for the charge generating substance and the charge transporting substance constituting the light sensitive layer is wide and a photoreceptor having optional characteristics can be manufactured relatively easily.

As the charge generating substance used in the function separated photoreceptor, various substances such as phthalocyanine pigment, squarylium dye, azo pigment, perylene pigment, polynuclear quinone pigment, cyanine dye, squaric acid dye, and pyrylium salt dye have been studied and various materials of excellent light fastness and having high charge generating ability have been proposed.

On the other hand, various compounds are known for the charge transporting substances, including, for example, pyrazoline compounds (e.g., refer to Japanese Examined Patent Publication JP-B2 52-4188 (1977)), hydrazone compounds (e.g., refer to Japanese Unexamined Patent Publication JP-A 54-150128 (1979), Japanese Examined Patent Publication JP-B2 55-42380 (1980), and Japanese Unexamined Patent Publication JP-A 55-52063 (1980)), triphenylamine compounds (e.g., refer to Japanese Examined Patent Publication JP-B2 58-32372 (1983) and Japanese Unexamined Patent Publication JP-A 2-190862 (1990)) and stilbene compounds (e.g., refer to Japanese Unexamined Patent Publications JP-A 54-151955 (1979) and JP-A 58-198043 (1983)). Recently, pyrene derivatives, naphthalene derivatives and terphenyl derivatives that have a condensed polycyclic hydrocarbon structure as the center nucleus have been developed (e.g., refer to Japanese Unexamined Patent Publication JP-A 7-48324 (1995)).

The charge transporting substances must satisfy the following requirements:
(1) they are stable to light and heat;
(2) they are stable to active substances such as ozone, nitrogen oxides (NOx) and nitric acid that may be generated in corona discharging on a photoreceptor;
(3) they have good charge transportability;
(4) they are compatible with organic solvents and binder resins;
(5) they are easy to produce and are inexpensive. Though partly satisfying some of these, however, the charge transporting substances disclosed in the above-mentioned patent publications could not satisfy all of these at high level.

Further, the charge transporting substance is required to have highly charge transportability, particularly, among the requirements described above. For example, in a case where the charge transporting layer in which a charge transporting substance is dispersed in the binder resin forms the surface layer of the photoreceptor, particularly high charge transportability is required for the charge transporting substance in order to ensure a sufficient light sensitivity.

In a case where, the photoreceptor is used being mounted on an electrophotographic apparatus, such as a copying machine or a laser beam printer, the surface layer of the photoreceptor is inevitably scraped off partially by a contact member such as a cleaning blade or a charging roller. In a case where the surface layer of the photoreceptor is scraped, the charge retainability of the photoreceptor lowers and images of good quality can no more be provided. Accordingly, for improving the durability of the copying machine, the laser beam printer, etc. it has been demanded for a photoreceptor having a surface layer resistant to the contact member, that is, a surface layer of high printing resistance with less amount scraped by the contact member.

In order to improve the durability of the photoreceptor by increasing the printing resistance of the surface layer, it may be considered to increase the content of the binder resin in the charge transporting layer as the surface layer. However, as the content of the binder resin in the charge transporting layer increases, it results in a problem that the light responsivity lowers. In a case where the light responsivity is low, that is, the decay speed of the surface potential after exposure is slow, since it is used repetitively in a state where the residual potential increases and the surface potential of the photoreceptor is not sufficiently decayed, the surface charges at the portion to be erased by the exposure are not erased sufficiently to result in troubles such as early lowering of the image quality.

Lowering of the light responsivity is attributable to a low charge transportability of the charge transporting substance. In the function separated photoreceptor, surface charges on the photoreceptor irradiated with a light are eliminated when charges generated in the charge generating substance by light absorption are transported by the charge transporting substance to the surface of the photoreceptor. Therefore, in a care where the content of the charge transporting substance in the charge transporting layer is lowered relatively along with increase of the content of the binder resin, the charge transportability of the charge transporting layer is further lowered when the charge transportability of the charge transporting substance is low to lower the light responsivity as described above. Accordingly, in order to prevent lowering of the light responsivity and ensure a sufficient light responsivity, a high charge transportability is required for the charge transporting substance.

Further, the size has been reduced and the speed has been increased recently in electrophotographic apparatus, for example, digital copying machines and printers, and improvement for the sensitivity has been required as the characteristics of the photoreceptor for coping with the increase of the speed, and high charge transportability has been demanded more and more as the charge transporting substance. Further, in the high speed electrophotographic process, since the time from exposure to development is short, a photoreceptor of high light responsivity is demanded. As described above, since the light responsivity depends on the charge transportability of the charge transporting substance, a charge transporting substance having a higher charge transportability is demanded also with such a view point.

As the charge transporting substance capable of satisfying such a demand, an enamine compound having a charge movability higher than that of the charge transporting substance described above has been proposed (refer, for example, to Japanese Unexamined Patent Publications JP-A 2-51162 (1990), JP-A 6-43674 (1994) and JP-A 10-69107 (1998)).

Further, a photoreceptor provided with a high charge transportability by the incorporation of a polysilane and improved with the chargeability and the film strength by the incorporation of an enamine compound having a specific structure has been proposed (refer to Japanese Unexamined Patent Publication JP-A 7-134430 (1995)).

On the other hand, in the electrophotographic process, the photoreceptor is exposed to an active gas such as ozone or NOx generated during charging by corona discharge, UV-rays contained in a light used for exposure and charge elimination, or heat. In a case where the photoreceptor is exposed to the active gas, UV-rays, or heat described above, free radicals are generated in the photosensitive layer to decompose or degrade the materials constituting the photosensitive layer. Accordingly, the charge transporting substance is required to be stable against light, heat, and active gas such as ozone or NOx as described above. However, charge transporting substance capable of satisfying such requirements has not yet been obtained and in a case where the photoreceptor is used repetitively, fatigue degradation such as lowering of the charge potential, increase of the residual potential, and lowering of the sensitivity are caused, particularly, due to the decomposition or degradation of the material consisting the photosensitive layer, particularly, the charge transporting substance to result in a problem of degradation of the image quality.

As the technique for preventing decomposition and degradation and for mitigating the fatigue degradation upon repetitive use of the charge transporting substance, etc. it has been known to add an antioxidant or a light stabilizer to the photosensitive layer (for example, refer to Japanese Examined Patent Publication JP-B2 2730744). However, when the antioxidant or light stabilizer is added to the photosensitive layer, while the fatigue degradation can be mitigated, it results in a problem of lowering the sensitivity and the light responsivity. Lowering of the sensitivity and the light responsivity develops particularly remarkably under a low temperature circumstance.

In order to suppress the lowering of the sensitivity and the light responsivity upon addition of the antioxidant, light stabilizer, etc. it may be considered to use a charge transporting substance of high charge movability. Then, it has been studied on combined use of the antioxidant and the light stabilizer with a specified charge transporting substance. For example, it has been proposed a combination of a hydrazone compound and an antioxidant (refer to Japanese Unexamined Patent Publication JP-A 64-44946 (1989)), a combination of an alkenylamine compound and an antioxidant (refer to Japanese Unexamined Patent Publication JP-A 11-271995 (1999)), and a combination of a diamine compound and a light stabilizer (refer to Japanese Unexamined Patent Publication JP-A 2001-51434).

Also in a case of using the antioxidant and the light stabilizer in combination with the specified charge transporting substance as described in JP-A 64-44946, 11-271995, and 2001-51434, its involves a problem that degradation due to repetitive use can not be improved sufficiently for those having good initial sensitivity, while the initial sensitivity and the chargeability are not sufficient for those showing a less degradation by the repetitive use.

Further, no sufficient sensitivity and light responsivity can be obtained under a low temperature circumstance even by the combined use of the antioxidant and the light stabilizer with the enamine compound of high charge transportability as described in JP-A 2-51162, 6-43674 or 10-69107. Further, in the photoreceptor described in JP-A 7-134430, while a high charge transportability is provided by the incorporation of polysilane, the photoreceptor using polysilane involves a problem that it is sensitive to light exposure and characteristic as the photoreceptor is lowered by exposure to light, for example, during maintenance even when the light stabilizer is added to the photosensitive layer.

DISCLOSURE OF THE INVENTION

It is an object of the invention to provide a highly reliable electrophotographic photoreceptor having high sensitivity, excellent in light responsivity, not suffering from lowering of such characteristics even when it is used under a low temperature circumstance or in a high speed electrophotographic process, or when it is exposed to light and stable against an active gas such as ozone or NOx, UV-rays, and heat, and with less fatigue degradation upon repetitive use, as well as an image forming apparatus having the same.

The invention provides an electrophotographic photoreceptor comprising:

a conductive substrate composed of a conductive material; and a photosensitive layer disposed on the conductive substrate and containing an enamine compound represented by the following general formula (1), and at least one of an antioxidant and a light stabilizer.

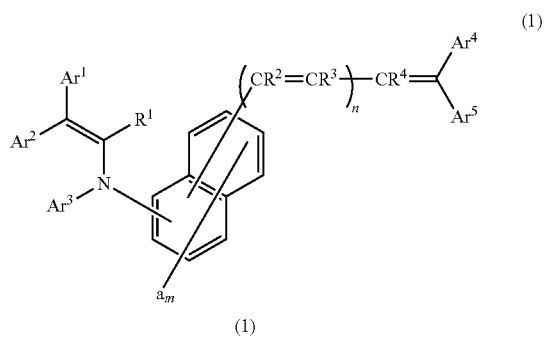

(1)

wherein $Ar^1$ and $Ar^2$ each represent an aryl group which may have a substituent or a heterocyclic group which may have a substituent; $Ar^3$ represents an aryl group which may have a substituent, a heterocyclic group which may have a substituent, an aralkyl group which may have a substituent, or an alkyl group which may have a substituent; $Ar^4$ and $Ar^5$ each represent a hydrogen atom, an aryl group which may have a substituent, a heterocyclic group which may have a substituent, an aralkyl group which may have a substituent, or an alkyl group which may have a substituent, but it is excluded that $Ar^4$ and $Ar^5$ are hydrogen atoms at the same time; $Ar^4$ and $Ar^5$ may bond to each other via an atom or an atomic group to form a cyclic structure; "a" represents an alkyl group which may have a substituent, an alkoxy group which may have a substituent, a dialkylamino group which may have a substituent, an aryl group which may have a substituent, a halogen atom, or a hydrogen atom; m indicates an integer of from 1 to 6; when m is 2 or more, then the "a"s may be the same or different and may bond to each other to form a cyclic structure; $R^1$ represents a hydrogen atom, a halogen atom, or an alkyl group which may have a substituent; $R^2$, $R^3$ and $R^4$ each represent a hydrogen atom, an alkyl group which may have a substituent, an aryl group which may have a substituent, a heterocyclic group which may have a substituent, or an aralkyl group which may have a substituent; n indicates an integer of from 0 to 3; when n is 2 or 3, then the $R^2$s may be the same or different and the $R^3$s may be the same or different, but when n is 0, $Ar^3$ is a heterocyclic group which may have a substituent.

In accordance with the invention, the electrophotographic photoreceptor has a conductive substrate and a photosensitive layer and the photosensitive layer contains an enamine compound represented by the general formula (1) and at least one of an antioxidant and a light stabilizer. The photosensitive layer may be any one of a photosensitive layer constituted with a single photoconductive layer containing a charge generating substance and a charge transporting substance, a photosensitive layer constituted with a photoconductive layer in which a charge generating layer containing a charge generating substance and a charge transporting layer containing a charge transporting substance are stacked, and a photosensitive layer in which a surface protective layer is further stacked on the photoconductive layer described above. Since the enamine compound represented by the general formula (1) has a high charge movability, by incorporating the enamine compound represented by the general formula (1) as the charge transporting substance in the photosensitive layer, it is possible to obtain an electrophotographic photoreceptor having high chargeability, sensitivity and light responsivity, and not suffering from lowering of such characteristics even when it is used under a low temperature circumstance or in a high speed electrophotographic process. Further, since a high charge transportability can be attained without incorporating polysilane in the photosensitive layer, the characteristics described above are not lowered even when the electrophotographic photoreceptor is exposed to light.

Further, since at least one of the antioxidant and the light stabilizer is incorporated in the photosensitive layer, the fatigue degradation upon repetitive use can be mitigated to improve the durability of the electrophotographic photoreceptor. This is considered to be attributable to that the antioxidant and the light stabilizer contained in the photosensitive layer react preferentially with free radicals generated in the photosensitive layer by an active gas such as ozone or NOx generated during charging by the corona discharge, as well as UV-rays and heat contained in light used for exposure and charge elimination, thereby preventing decomposition or degradation of the enamine compound represented by the general formula (1) contained as the charge transporting substance. In a case where at least one of the antioxidant and the light stabilizer is incorporated in the photosensitive layer, since at least one of the antioxidant and the light stabilizer is incorporated in the coating solution upon forming the photosensitive layer by coating, the stability of the coating solution can be improved. Accordingly, since an electrophotographic photoreceptor having substantially identical characteristics can be manufactured in a case of forming a photosensitive layer soon after the preparation of a coating solution or in a case of forming a photosensitive layer after lapse of a long time, it is possible to improve the stability for quality and the productivity of an electrophotographic photoreceptor.

In the electrophotographic photoreceptor according to the invention, since the enamine compound of high charge movability represented by the general formula (1) is contained as the charge transporting substance in the photosensitive layer, the sensitivity and the light responsivity are not lowered through the antioxidant and the light stabilizer are incorporated in the photosensitive layer.

Accordingly, by incorporating the enamine compound represented by the general formula (1) and at least one of the antioxidant and the light stability in combination into the photosensitive layer as described above, it is possible to obtain a highly reliable electrophotographic photoreceptor having high chargeability, sensitivity, and light responsivity, not suffering from lowering of the characteristics described above even when it is used under a low temperature circumstance or in a high speed electrophotographic process, or when it is exposed to light, stable against the active gas such as ozone or NOx, UV-rays and heat, and with less fatigue degradation upon repetitive use.

Further, the invention is characterized in that the enamine compound represented by the general formula (1) is an enamine compound represented by the following general formula (2).

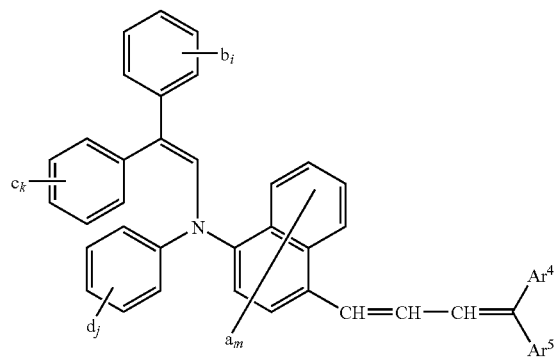

(2)

wherein "b", "c" and "d" each represent an alkyl group which may have a substituent, an alkoxy group which may have a substituent, a dialkylamino group which may have a substituentv, an aryl group which may have a substituent, a halogen atom, or a hydrogen atom; "i", "k" and "j" each indicate an integer of from 1 to 5; when "i" is 2 or more, then the "b"s may be the same or different and may bond to each other to form a cyclic structure; when "k" is 2 or more, then the "c"s may be the same or different and may bond to each other to form a cyclic structure; and when "j" is 2 or more, then the "d"s may be the same or different and may bond to each other to form a cyclic structure; $Ar^4$, $Ar^5$, "a" and "m" represent the same as those defined in formula (1).

In accordance with the invention, since the enamine compound represented by the general formula (2) having particularly high charge movability among the enamine compounds represented by the general formula (1) is contained in the photosensitive layer, it is possible to obtain an electrophotographic photoreceptor having higher sensitivity and light responsivity. Further, since the enamine compound represented by the general formula (2) can be synthesized relatively easily and shows high yield among the enamine compounds represented by the general formula (1), it can be manufactured at a reduced cost. Accordingly, the electrophotographic photoreceptor of the invention having the excellent characteristics as described above can be manufactured at a reduced manufacturing cost.

Further, the invention is characterized in that the enamine compound represented by the general formula (1) is an enamine compound represented by the following general formula (1a).

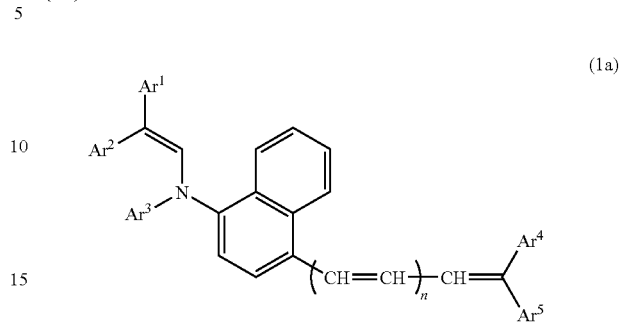

(1a)

wherein $Ar^1$ and $Ar^2$ each represents a phenyl group; $Ar^3$ represents a tolyl group, p-methoxyphenyl group, naphthyl group, or 5-methyl-2-thienyl group; $Ar^4$ represents a hydrogen atom, lower alkyl group or phenyl group; $Ar^5$ represents a phenyl group or p-methoxyphenyl group; and n represents an integer of 1 to 2.

The compound of the general formula (1a) not only has high charge movability but also can be manufactured at a reduced cost since the synthesis is easy and the yield is high. Accordingly, the electrophotographic photoreceptor containing the compound of the invention has high sensitivity, and is excellent in the responsivity and also excellent in view of the cost.

Further, the invention is characterized in that the antioxidant is a hindered phenol compound having a hindered phenol structural unit.

Further, the invention is characterized in that the hindered phenol compound is a compound represented by the following structural formula (I-a).

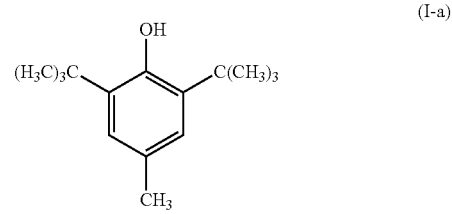

(I-a)

In accordance with the invention, the photosensitive layer contains, as an antioxidant, a hindered phenol compound having a hindered phenol structural unit, preferably, a hindered phenol compound represented by the structural formula (I-a). By the incorporation of the hindered phenol compound, particularly, the hindered phenol compound represented by the structural formula (I-a) in the photosensitive layer, decomposition or degradation of the enamine compound represented by the general formula (1) contained as the charge transporting substance in the photosensitive layer can be suppressed particularly to further mitigate the fatigue degradation upon repetitive use and the durability of the electrophotographic photoreceptor can be improved further. Further, the stability of the coating solution upon forming the photosensitive layer by coating can be improved further to further improve the stability for the quality and the productivity of the electrophotographic photoreceptor.

Further, the invention is characterized in that the antioxidant is a phosphoric antioxidant.

In accordance with the invention, the photosensitive layer contains the phosphoric antioxidant. By the incorporation of the phosphoric antioxidant in the photosensitive layer, decomposition or degradation of the enamine compound represented by the general formula (1) contained as the charge transporting substance in the photosensitive layer can be suppressed particularly to further mitigate the fatigue degradation upon repetitive use and further improve the durability of the electrophotographic photoreceptor. Further, the stability of the coating solution upon forming the photosensitive layer by coating can be improved further to further improve the stability for quality and the productivity of the electrophotographic photoreceptor.

Further the invention is characterized in that the antioxidant is an organic sulfuric antioxidant.

In accordance with the invention, the photosensitive layer contains the organic sulfuric antioxidant. By the incorporation of the organic sulfuric antioxidant in the photosensitive layer, decomposition or degradation of the enamine compound represented by the general formula (1) contained as the charge transporting substance in the photosensitive layer can be suppressed particularly to further mitigate the fatigue degradation upon repetitive use and further improve the durability of the electrophotographic photoreceptor. Further, the stability of the coating solution upon forming the photosensitive layer by coating can be improved further to further improve the stability of quality and the productivity of the electrophotographic photoreceptor.

Further, the invention is characterized in that the light stabilizer is a hindered amine compound having a hindered amine structural unit.

Further, the invention is characterized in that the hindered amine compound is a compound represented by the following structural formula (II-a).

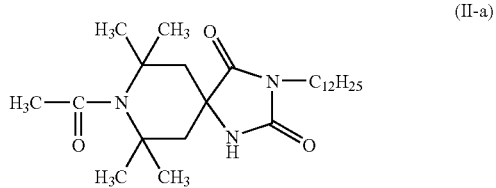

(II-a)

In accordance with the invention, the photosensitive layer contains, as a light stabilizer, a hindered amine compound having a hindered amine structural unit, preferably, a hindered amine compound represented by the structural formula (II-a). Decomposition or degradation of the enamine compound represented by the general formula (1) contained as the charge transporting substance in the photosensitive layer is suppressed particularly to further mitigate the fatigue degradation upon repetitive use and further improve the durability of the electrophotographic photoreceptor. Further, the stability of the coating solution upon forming the photosensitive layer by coating can be improved further to further improve the stability of quality and the productivity of the electrophotographic photoreceptor.

Further, the invention is characterized in that the light stabilizer is a benzotriazole derivative.

In accordance with the invention, the photosensitive layer contains a benzotriazole derivative as a light stabilizer. By the incorporation of the benzotriazole derivative in the photosensitive layer, decomposition or degradation of the enamine compound represented by the general formula (1) contained as the charge transporting substance in the photosensitive layer is suppressed particularly to further mitigate the fatigue degradation upon repetitive use and further improve the durability of the electrophotographic photoreceptor. Further, the stability of the coating solution upon forming the photosensitive layer by coating can be further improved to further improve the stability of quality and the productivity of the electrophotographic photoreceptor.

Further, the invention is characterized in that the photosensitive layer contains 0.1 to 15% by weight of the antioxidant.

In accordance with the invention, since the content of the antioxidant contained in the photosensitive layer is selected to a suitable range, an effect sufficient to the improvement of the durability of the electrophotographic photoreceptor and the improvement of the stability of the coating solution can be obtained, and lowering of the characteristics of the electrophotographic photoreceptor by the incorporation of the antioxidant can be minimized.

Further, the invention is characterized in that the photosensitive layer contains 0.1 to 10% by weight of the light stabilizer.

In accordance with the invention, since the content of the light stabilizer contained in the photosensitive layer is selected to a suitable range, an effect sufficient to the improvement of the durability of the electrophotographic photoreceptor and the improvement of the stability of the coating solution can be obtained, and lowering of the characteristics of the electrophotographic photoreceptor by the incorporation of the light stabilizer can be minimized.

Further, the invention provides an image forming apparatus comprising:

the electrophotographic photoreceptor of the invention;

charging means for charging the electrophotographic photoreceptor;

exposure means for applying exposure to the charged electrophotographic photoreceptor; and developing means for developing electrostatic latent images formed by exposure.

In accordance with the invention, the image forming apparatus has the electrophotographic photoreceptor of the invention, the charging means, the exposure means and the developing means. The electrophotographic photoreceptor of the invention has high chargeability, sensitivity and light responsivity, does not suffer from lowering of the characteristics described above even in a case when it is used under a low temperature circumstance or in a high speed electrophotographic process, is stable against an active gas such as ozone or NOx, UV-rays and heat, suffers from less fatigue degradation upon repetitive use and has high reliability. Accordingly, a highly reliable image forming apparatus capable of providing high quality image stably for a long time under various circumstances can be obtained. Further, since the electrophotographic photoreceptor of the invention does not suffer from lowering of the characteristics described above even in a case when it is exposed to light, it is possible to prevent lowering of image quality caused by exposure of the electrophotographic photoreceptor to light during maintenance or the like to improve the reliability of the image forming apparatus.

BRIEF DESCRIPTION OF DRAWINGS

Other and further objects, features, and advantages of the invention will be more explicit from the following detailed description taken with reference to the drawings wherein:

FIG. 1A is a perspective view schematically showing the constitution of an electrophotographic photoreceptor 1 according to a first embodiment of the invention, and FIG. 1B is a fragmentary cross sectional view schematically showing the constitution of the electrophotographic photoreceptor 1;

BEST MODE FOR CARRYING OUT THE INVENTION

Figure 2:
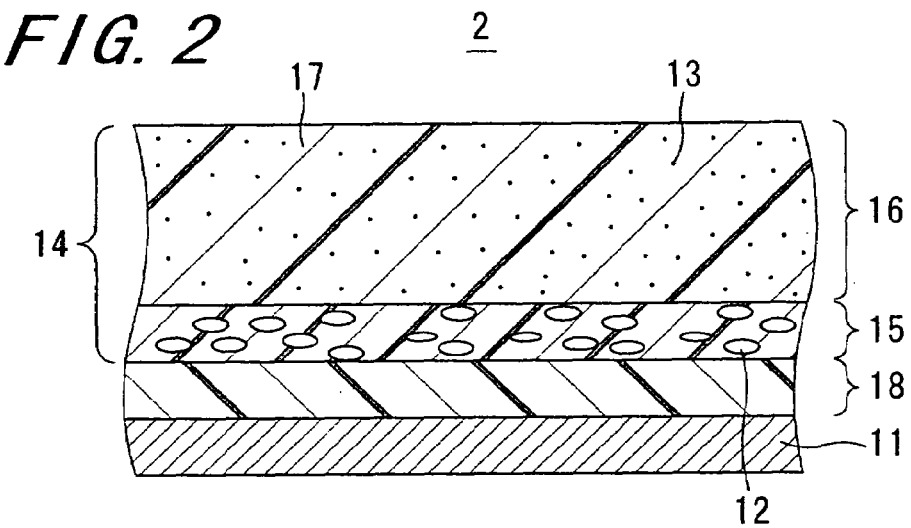
FIG. 2 is a cross sectional view schematically showing the constitution of an electrophotographic photoreceptor according to a second embodiment of the invention.

Now referring to the drawings, preferred embodiments of the invention are described below. However, the invention is not restricted to the embodiments.

FIG. 1A is a perspective view schematically showing the constitution of an electrophotographic photoreceptor 1 according to a first embodiment of the invention. FIG. 1B is a fragmentary cross sectional view schematically showing the constitution of the electrophotographic photoreceptor 1. The electrophotographic photoreceptor 1 (hereinafter also referred to simply as "photoreceptor") includes a cylindrical conductive substrate 11 composed of a conductive material, and a photosensitive layer 14 disposed on the circumferential surface of the conductive substrate 11. The photosensitive layer 14 is constituted with a photoconductive layer in which a charge generating layer 15 containing a charge generating substance 12 that generates charges by absorption of light and a charge transporting layer 16 containing a charge transporting substance 13 having a function of receiving charges generated by the charge generating substance 12 and transporting them are stacked in this order on an outer circumferential surface of the conductive substrate 11. That is, the electrophotographic photoreceptor 1 is a layered photoreceptor.

The photosensitive layer 14 contains at least one of an antioxidant and a light stabilizer. The antioxidant and the light stabilizer may be contained in either of the charge generating layer 15 and the charge transporting layer 16 constituting the photosensitive layer 14, or may be contained in both of the charge generating layer 15 and the charge transporting layer 16. It is preferred that the antioxidant and the light stabilizer are contained at least in the charge transporting layer 16.

For the charge transporting substance 13 contained in the charge transporting layer 16, an enamine compound represented by the following formula (1) is used.

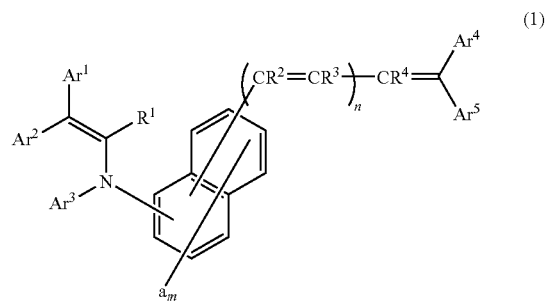

In the general formula (1), $Ar^1$ and $Ar^2$ each represent an aryl group which may have a substituent or a heterocyclic group which may have a substituent; $Ar^3$ represents an aryl group which may have a substituent, a heterocyclic group which may have a substituent, an aralkyl group which may have a substituent, or an alkyl group which may have a substituent; $Ar^4$ and $Ar^5$ each represent a hydrogen atom, an aryl group which may have a substituent, a heterocyclic group which may have a substituent, an aralkyl group which may have a substituent, or an alkyl group which may have a substituent, but it is excluded that $Ar^4$ and $Ar^5$ are hydrogen atoms at the same time; $Ar^4$ and $Ar^5$ may bond to each other via an atom or an atomic group to form a cyclic structure; "a" represents an alkyl group which may have a substituent, an alkoxy group which may have a substituent, a dialkylamino group which may have a substituent, an aryl group which may have a substituent, a halogen atom, or a hydrogen atom; m indicates an integer of from 1 to 6; when m is 2 or more, then the "a"s may be the same or different and may bond to each other to form a cyclic structure; $R^1$ represents a hydrogen atom, a halogen atom, or an alkyl group which may have a substituent; $R^2$, $R^3$ and $R^4$ each represent a hydrogen atom, an alkyl group which may have a substituent, an aryl group which may have a substituent, a heterocyclic group which may have a substituent, or an aralkyl group which may have a substituent; n indicates an integer of from 0 to 3; when n is 2 or 3, then the $R^2$s may be the same or different and the $R^3$s may be the same or different, but when n is 0, $Ar^3$ is a heterocyclic group which may have a substituent.

In the general formula (1), specific examples of the aryl group represented by $Ar^1$, $Ar^2$, $Ar^3$, $Ar^4$, $Ar^5$, "a", $R^2$, $R^3$ or $R^4$ can include, for example, phenyl, naphthyl, pyrenyl and anthonyl. A substituent which may be present on the aryl group include, for example, alkyl groups such as methyl, ethyl, propyl and trifluoromethyl, alkenyl groups such as 2-propenyl and styryl, alkoxy groups such as methoxy, ethoxy and propoxy, amino groups such as methylamino and dimethylamino, halogeno groups such as fluoro, chloro and bromo, aryl groups such as phenyl and naphthyl, aryloxy groups such as phenoxy, and arylthio groups such as thiophenoxy. Specific examples of the aryl group having such substituents can include tolyl, methoxyphenyl, biphenylyl, terphenyl, phenoxyphenyl, p-(phenylthio)phenyl and p-styrylphenyl.

In the general formula (1), specific examples of the heterocyclic group represented by $Ar^1$, $Ar^2$, $Ar^3$, $Ar^4$, $Ar^5$, $R^2$, $R^3$ or $R^4$ can include furyl, thienyl, thiazoryl, benzofuryl, benzothiophenyl, benzothiazoryl and benzooxazoryl. A substituent which may be present on the heterocyclic group described above can include, for example, substituents similar to those which may be present on the aryl group represented by $Ar^1$ and the like described above, and specific examples of the heterocyclic group having a substituent can include N-methyl indolyl and N-ethyl carbazolyl.

In the general formula (1), specific examples of the aralkyl group of $Ar^3$, $Ar^4$, $Ar^5$, $R^2$, $R^3$ or $R^4$ can include, for example, benzyl and 1-naphthylmethyl. A substituent which may be present on the aralkyl group described above can include, for example, substituents similar to those which may be present on the aryl group represented by $Ar^1$ and the like described above, and specific examples of the aralkyl group having a substituent can include p-methoxybenzyl.

In the general formula (1), as the alkyl group represented by $Ar^3$, $Ar^4$, $Ar^5$, "a", $R^1$, $R^2$, $R^3$ or $R^4$, those having from 1 to 6 carbon atoms are preferred, and specific examples thereof can include chained alkyl groups such as methyl, ethyl, n-propyl, isopropyl and t-butyl, and cycloalkyl groups such as cyclohexyl and cyclopentyl. A substituent which may be present on the alkyl groups described above can include substituents similar to those which may be present on the aryl group represented by $Ar^1$ described above, and specific examples of the alkyl group having a substituent can include halogenated alkyl groups such as trifluoromethyl and fluoromethyl, alkoxyalkyl groups such as 1-methoxyethyl, and alkyl groups substituted with a heterocyclic group such as 2-thienylmethyl.

In the general formula (1), as the alkoxy group represented by "a", those having from 1 to 4 carbon atoms are preferred, and specific examples can include methoxy, ethoxy, n-propoxy and isopropoxy. A substituent which may be present on the alkyl group described above can include substituents similar to those which may be present on the aryl group represented by $Ar^1$ described above.

In the general formula (1), as the dialkylamino group represented by "a", those having from 1 to 4 carbon atoms substituted with an alkyl group are preferred, and specific examples can include, dimethylamino, diethylamino and diisopropylamino. A substituent which may be present on the dialylamino group can include, for example, substituents similar to those which may be present on the aryl group represented by $Ar^1$.

In the general formula (1), specific examples of the halogen atom represented by "a" or $R^1$ can include a fluorine atom and a chlorine atom.

In the general formula (1), specific examples of the atoms for bonding $Ar^4$ and $Ar^5$ can include an oxygen atom, sulfur atom and nitrogen atom. The nitrogen atom, for example, as a bivalent group such as an imino group or N-alkylimino group, bonds $Ar^4$ and $Ar^5$. Specific examples of the atomic group for bonding $Ar^4$ and $Ar^5$ can include bivalent groups, for example, an alkylene group such as methylene, ethylene and methylmethylene, an alkenylene group such as vinylene and propenylene, an alkylene group containing a hetero atom such as oxymethylene (chemical formula: —O—$CH_2$—), and an alkenylene group containing a hetero atom such as thiovinylene (chemical formula: S—CH=CH—).

Since the enamine compound represented by the general formula (1) has a high charge movability, by the incorporation of the enamine compound represented by the general formula (1) as the charge transporting substance 13 in the photosensitive layer 14, it is possible to obtain an electrophotographic photoreceptor 1 having high chargeability, sensitivity and light responsivity and not suffering from lowering of the characteristics described above even in a case where it is used under a low temperature circumstance or in a high speed electrophotographic process. Further, since high charge movability can be attained without incorporating polysilane in the photosensitive layer 14, the characteristics described above are not lowered even in a case where the electrophotographic photoreceptor 1 is exposed to a light.

Further, since at least one of the antioxidant and the light stabilizer is contained in the photosensitive layer 14 as described above, fatigue degradation upon repetitive use can be mitigated to improve the durability of the electrophotographic photoreceptor 1. This is considered to be attributable to that the antioxidant and the light stabilizer contained in the photosensitive layer 14 react preferentially with free radicals generated in the photosensitive layer 14 by an active gas such as ozone or NOx generated during charging by the corona discharge, as well as UV-rays and heat contained in light used for exposure and charge elimination, thereby preventing decomposition or degradation of the enamine compound represented by the general formula (1) contained as the charge transporting substance 13. Further, in a case where at least one of the antioxidant and the light stabilizer is contained in the photosensitive layer 14, since at least one of the antioxidant and the light stabilizer is contained in the coating solution upon forming the photosensitive layer 14 by coating, the stability of the coating solution can be improved. Accordingly, even in a case of forming the photosensitive layer 14 just after preparation of the coating solution or in a case of forming the photosensitive layer 14 after lapse of long time, since an electrophotographic photoreceptor 1 having substantially identical characteristics can be manufactured, the stability of quality and the productivity of the electrophotographic photoreceptor 1 can be improved.

In a case of incorporating the antioxidant and the light stabilizer in the photosensitive layer 14, while the sensitivity and the light responsivity may be lowered sometimes, since the electrophotographic photoreceptor 1 of this embodiment contains the enamine compound of high charge movability represented by the general formula (1) as the charge transporting substance 13 in the photosensitive layer 14 as described above, the sensitivity and the light responsivity are not lowered even when the antioxidant and the light stabilizer is contained in the photosensitive layer 14.

Accordingly, by the incorporation of the enamine compound represented by the general formula (1) and at least one of antioxidant and the light stabilizer in combination in the light sensitive layer 14 as described above, it is possible to obtain highly reliable electrophotographic photoreceptor 1 having high chargeability, sensitivity and light responsivity, not suffering from lowering of the characteristics even in a case where it is used under a low temperature circumstance or in a high speed photographic process or when it is exposed to light, stable against an active gas such as ozone or NOx, UV-rays and heat, and with less fatigue deterioration upon repetitive use.

For the charge transporting substance 13, an enamine compound represented by the following general formula (2), among enamine compounds represented by the general formula (1), is preferably used.

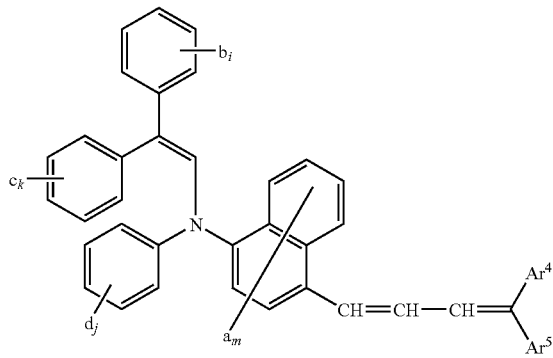

(2)

In the general formula (2), "b", "c" and "d" each represent an alkyl group which may have a substituent, an alkoxy group which may have a substituent, a dialkylamino group which may have a substituent, an aryl group which may have a substituent, a halogen atom, or a hydrogen atom; "i", "k" and "j" each indicate an integer of from 1 to 5; when "i" is 2 or more, then the "b"s may be the same or different and may bond to each other to form a cyclic structure; when "k" is 2 or more, then the "c"s may be the same or different and may bond to each other to form a cyclic structure; and when "j" is 2 or more, then the "d"s may be the same or different and may bond to each other to form a cyclic structure; $Ar^4$, $Ar^5$, "a" and "m" represent the same as those defined in formula (1).

In the general formula (2), the alkyl group represented by b, c or d is preferably those having from 1 to 6 carbon atoms, and specific examples thereof can include chained alkyl groups such as methyl, ethyl, n-propyl and isopropyl, and cycloalkyl groups such as cyclohexyl and cyclopentyl. A substituent which may be present on the alkyl group described above can include, for example, substituents similar to those which may be present on the aryl group represented by $Ar^1$ and the like described above, and the specific examples of the alkyl group having a substituent can include halogenated alkyl groups such as trifluoromethyl and fluoromethyl and alkoxyalkyl groups such as 1-methylethyl and alkyl groups substituted with a heterocyclic group such as 2-thienylmethyl.

In the general formula (2), the alkoxy group represented by b, c or d is preferably those having from 1 to 4 carbon atoms, and specific examples thereof can include, methoxy, ethoxy, n-propoxy and isopropoxy. A substituent which may be present on the alkyl groups can include, for example, substituents similar to those which may be present on the aryl group represented by $Ar^1$ and the like described above.

In the general formula (2), the dialkyl group represented by b, c or d is preferably those substituted with an alkyl group having from 1 to 4 carbon atoms, and specific examples thereof can include dimethylamino, diethylamino and diisopropylamino. A substituent which the dialkylamino groups can include, for example, substituents similar to those which may be present on the aryl group represented by $Ar^1$ and the like described above.

In the general formula (2), specific examples of the aryl group represented by b, c or d can include phenyl and naphthyl. A substituent which may be present on the aryl groups can include, for example, substituents similar to those which may be present on the aryl group represented by $Ar^1$ and the like described above, and specific examples of the aryl group having the substituent can include tolyl and methoxyphenyl.

In the general formula (2), specific examples of the halogen atom represented by b, c or d can include, a fluorine atom and a chlorine atom.

Since the enamine compound represented by the general formula (2) has particularly high charge movability among the enamine compounds represented by the general formula (1), an electrophotographic photoreceptor having higher sensitivity and light responsivity can be obtained by using the enamine compound represented by the general formula (2) as the charge transporting substance 13.

Further, since the enamine compound represented by the general formula (2) can be synthesized relatively easily and shows high yield among the enamine compounds represented by the general formula (1), it can be manufactured at a reduced cost. Accordingly, the electrophotographic photoreceptor 1 of this embodiment having the excellent characteristics as described above can be manufactured at a reduced manufacturing cost.

Among the enamine compounds represented by the general formula (1), compounds having especially excellent in view of the characteristics, cost and productivity can include, for example, those in which each of $Ar^1$ and $Ar^2$ represents a phenyl group, $Ar^3$ represents a phenyl group, tolyl group, p-methoxyphenyl group, biphenylyl group, naphthyl group or thienyl group, at least one of $Ar^4$ and $Ar^5$ represents a phenyl group, p-tolyl group, p-methoxyphenyl group, naphthyl group, thienyl group or thiazolyl group, and $R^1$, $R^2$, $R^3$ and $R^4$ each represents a hydrogen atom, and n represents 1.

Among the enamine compounds represented by the general formula (1), a more preferred compound is an enamine compound represented by the following general formula (1a).

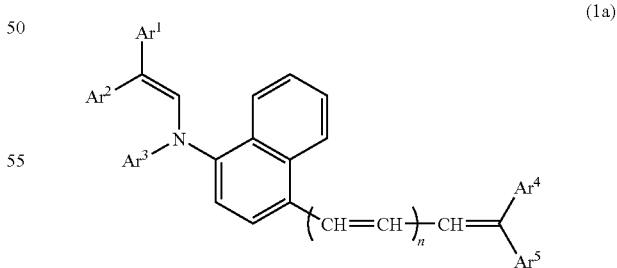

(1a)

(in the formula, $Ar^1$ and $Ar^2$ each represents a phenyl group. $Ar^3$ represents a tolyl group, p-methoxyphenyl group, naphthyl group, or 5-methyl-2-thienyl group, $Ar^4$ represents a hydrogen atom, lower alkyl group or phenyl group. $Ar^5$ represents a phenyl group or p-methoxyphenyl group. n represents an integer of 1 to 2).

Not only the compound of the general formula (1a) has high charge movability but also the starting material is easily available, the synthesis is easy, the yield is high, and it can be manufactured at a reduced cost. Accordingly, an electrophotographic photoreceptor of the invention having high sensitivity and excellent in the responsivity can be manufactured at a reduced cost by using the compounds.

Specific examples of enamine compounds represented by the general formula (1) can include, for example, Exemplified Compounds No. 1 to No. 220, in Tables 1 to 32 described below, but they are not limited to them. Further, in Tables 1 to 32, each of the exemplified compounds is represented by a group corresponding to each group of the general formula (1). For example, Exemplified Compound No. 1 shown in Table 1 is an enamine compound represented by the following structural formula (1-1). In Tables 1 to 32, in a case of exemplifying those in which $Ar^4$ and $Ar^5$ bond with each other by way of an atom or an atomic group to form a ring structure, carbon-carbon double bonds for bonding $Ar^4$ and $Ar^5$, and ring structures formed by $Ar^4$ and $Ar^5$ together with the carbon atom of the carbon-carbon double bonds are shown in the column for $Ar^4$ to the column for $Ar^5$.

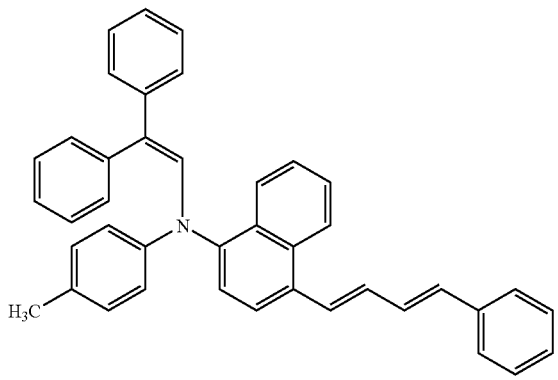

(1-1)

TABLE 1

| Compound No. | Ar¹ | Ar² | R¹ | Ar³ | ![structure] | n | $-(CR^2=CR^3)_n-$ | R⁴ | Ar⁴ | Ar⁵ |
|---|---|---|---|---|---|---|---|---|---|---|
| 1 | phenyl | phenyl | H | 4-methylphenyl | 1-methyl-4-N-naphthyl | 1 | CH=CH | H | H | phenyl |
| 2 | phenyl | phenyl | H | 4-methylphenyl | 1-methyl-4-N-naphthyl | 1 | CH=CH | H | H | 4-CH₃-phenyl |
| 3 | phenyl | phenyl | H | 4-methylphenyl | 1-methyl-4-N-naphthyl | 1 | CH=CH | H | —CH₃ | 4-OCH₃-phenyl |
| 4 | phenyl | phenyl | H | 4-methylphenyl | 1-methyl-4-N-naphthyl | 1 | CH=CH | H | H | 4-N(CH₃)₂-phenyl |

TABLE 1-continued

| Compound No. | Ar¹ | Ar² | R¹ | Ar³ | ![structure] | n | $-(CR^2=CR^3)_n-$ | R⁴ | Ar⁴ | Ar⁵ |
|---|---|---|---|---|---|---|---|---|---|---|
| 5 | phenyl | phenyl | H | p-tolyl | 4-methyl-1-naphthyl | 1 | CH=CH | H | H | 4-isopropylphenyl |
| 6 | phenyl | phenyl | H | p-tolyl | 4-methyl-1-naphthyl | 1 | CH=CH | H | H | 4-chlorophenyl |
| 7 | phenyl | phenyl | H | p-tolyl | 4-methyl-1-naphthyl | 1 | CH=CH | H | —CH₃ | m-tolyl |

TABLE 2

| Compound No. | Ar¹ | Ar² | R¹ | Ar³ | $\displaystyle -\!\!\left(\!\!\begin{array}{c}\\ \\ \\ \end{array}\!\!\right)_{\!\!a_m}$ | n | $-(CR^2=CR^3)_n-$ | R⁴ | Ar⁴ | Ar⁵ |
|---|---|---|---|---|---|---|---|---|---|---|
| 8 | 4-methylphenyl | phenyl | H | 4-methylphenyl | 4-methyl-1-naphthyl (N-attached) | 1 | CH=CH | H | H | 2-fluoro-methylphenyl |
| 9 | 4-methylphenyl | phenyl | H | 4-methylphenyl | 4-methyl-1-naphthyl (N-attached) | 1 | CH=CH | H | —CH₃ | 4-(CH₂CH₂F)-phenyl |
| 10 | 4-methylphenyl | phenyl | H | 4-methylphenyl | 4-methyl-1-naphthyl (N-attached) | 1 | CH=CH | H | —CH₃ | 3,5-dimethyl-4-methyl-(OCH₃)-phenyl |
| 11 | 4-methylphenyl | phenyl | H | 4-methylphenyl | 4-methyl-1-naphthyl (N-attached) | 1 | CH=CH | H | H | 5-methyl-1,2,3,4-tetrahydronaphthyl |

TABLE 2-continued

| Compound No. | Ar¹ | R¹ | Ar³ | ⟨a⟩ₘ | n | ⟨CR²=CR³⟩ₙ | R⁴ | Ar⁴ | Ar⁵ |
|---|---|---|---|---|---|---|---|---|---|
| 12 | Ar² (4-methylphenyl, phenyl) | H | 4-methylphenyl | 4-methyl-1-naphthyl | 1 | CH=CH | H | H | chroman-6-yl |
| 13 | Ar² (4-methylphenyl, phenyl) | H | 4-methylphenyl | 4-methyl-1-naphthyl | 1 | CH=CH | H | H | 4-biphenyl |
| 14 | Ar² (4-methylphenyl, phenyl) | H | 4-methylphenyl | 4-methyl-1-naphthyl | 1 | CH=CH | H | H | 4-(phenylthio)phenyl |

TABLE 3

| Compound No. | Ar¹ | Ar² | R¹ | Ar³ | [core] | n | −(CR²=CR³)ₙ− | R⁴ | Ar⁴ | Ar⁵ |
|---|---|---|---|---|---|---|---|---|---|---|
| 15 | 4-methylphenyl | phenyl | H | 4-methylphenyl | 4-methylnaphthyl | 1 | CH=CH | H | H | 4-(4-methylphenoxy)phenyl |
| 16 | 4-methylphenyl | phenyl | H | 4-methylphenyl | 4-methylnaphthyl | 1 | CH=CH | H | −CH₃ | 4-biphenyl |
| 17 | 4-methylphenyl | phenyl | H | 4-methylphenyl | 4-methylnaphthyl | 1 | CH=CH | H | H | 4-methylstilbenyl |
| 18 | 4-methylphenyl | phenyl | H | 4-methylphenyl | 4-methylnaphthyl | 1 | CH=CH | H | −CH₃ | 1-naphthyl |

TABLE 3-continued

| Compound No. | Ar¹ | R¹ | Ar³ | (structure with N, a_m) | n | $(CR^2=CR^3)_n$ | R⁴ | Ar⁴ | Ar⁵ |
|---|---|---|---|---|---|---|---|---|---|
| 19 | 4-methylphenyl | H | 4-methylphenyl | 4-methyl-1-naphthyl | 1 | CH=CH | H | H | 4-methyl-1-methoxynaphthyl |
| 20 | 4-methylphenyl | H | 4-methylphenyl | 4-methyl-1-naphthyl | 1 | CH=CH | H | H | 6-methoxy-2-methylnaphthyl |
| 21 | 4-methylphenyl | H | 4-methylphenyl | 4-methyl-1-naphthyl | 1 | CH=CH | H | H | 9-methylanthryl |

TABLE 4
| Compound No. | Ar¹ | Ar² | R¹ | Ar³ | $\underset{a_m}{\text{(structure)}}$ | n | $-(CR^2=CR^3)_n-$ | R⁴ | Ar⁴ | Ar⁵ |
|---|---|---|---|---|---|---|---|---|---|---|
| 22 |  |  | H | 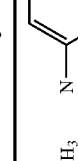 | 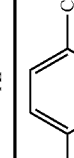 | 1 | CH=CH | H | H | 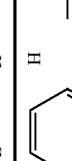 |
| 23 | (phenyl) | (phenyl) | H | (p-tolyl) | (N-methylnaphthyl) | 1 | CH=CH | H | —CH₃ | 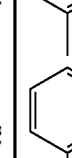 |
| 24 | (phenyl) | (phenyl) | H | (p-tolyl) | (N-methylnaphthyl) | 1 | CH=CH | H | —CH₃ |  |
| 25 | (phenyl) | (phenyl) | H | (p-tolyl) | (N-methylnaphthyl) | 1 | CH=CH | H | H |  |

TABLE 4-continued

| Compound No. | Ar¹ | Ar² | R¹ | Ar³ | [structure with N]ₐₘ | n | ─(CR²=CR³)ₙ─ | R⁴ | Ar⁴ | Ar⁵ |
|---|---|---|---|---|---|---|---|---|---|---|
| 26 | phenyl | phenyl | H | p-tolyl | 4-methylnaphthalen-1-yl (N-substituted) | 1 | CH=CH | H | H | 2-methylbenzothiazolyl |
| 27 | phenyl | phenyl | H | p-tolyl | 4-methylnaphthalen-1-yl (N-substituted) | 1 | CH=CH | H | H | 9-ethyl-3-carbazolyl |
| 28 | phenyl | phenyl | H | p-tolyl | 4-methylnaphthalen-1-yl (N-substituted) | 1 | CH=CH | H | phenyl | phenyl |

TABLE 5

| Compound No. | Ar¹ | Ar² | R¹ | Ar³ | [structure with N, a_m] | n | —(CR²=CR³)_n— | R⁴ | Ar⁴ | Ar⁵ |
|---|---|---|---|---|---|---|---|---|---|---|
| 29 | phenyl | phenyl | H | 4-methylphenyl | 4-methyl-naphthyl (N-linked) | 1 | CH=CH | H | 4-methylphenyl | 4-methylphenyl |
| 30 | phenyl | phenyl | H | 4-methylphenyl | 4-methyl-naphthyl (N-linked) | 1 | CH=CH | H | 4-methoxyphenyl | 4-methoxyphenyl |
| 31 | phenyl | phenyl | H | 4-methylphenyl | 4-methyl-naphthyl (N-linked) | 1 | CH=CH | H | 4-N(CH₃)₂-phenyl | 4-N(CH₃)₂-phenyl |
| 32 | phenyl | phenyl | H | 4-methylphenyl | 4-methyl-naphthyl (N-linked) | 1 | CH=CH | H | phenyl | phenyl |

TABLE 5-continued

| Compound No. | Ar¹ | R¹ | Ar² | (image) | n | $-(CR^2=CR^3)_n-$ | R⁴ | Ar⁴ | Ar⁵ |
|---|---|---|---|---|---|---|---|---|---|
| 33 | 4-methylphenyl | H | 4-biphenyl | 1-methyl-4-aminonaphthyl (N-tolyl) | 1 | CH=CH | H | phenyl | 2-thienylmethylene |
| 34 | 4-methylphenyl | H | 4-biphenyl | 1-methyl-4-aminonaphthyl (N-tolyl) | 1 | CH=CH | H |  | 1-methylene-1,2,3,4-tetrahydronaphthyl |
| 35 | 4-methylphenyl | H | 4-biphenyl | 1-methyl-4-aminonaphthyl (N-tolyl) | 1 | CH=CH | H |  | 10-methylene-9,10-dihydroanthryl |

TABLE 6

| Compound No. | Ar¹ | Ar² | R¹ | Ar³ | ⟨N...⟩aₘ | n | —(CR²=CR³)ₙ— | R⁴ | Ar⁴ | Ar⁵ |
|---|---|---|---|---|---|---|---|---|---|---|
| 36 | phenyl | phenyl | H | p-tolyl | 4-methyl-1-naphthyl-N | 1 | CH=CH | H | dibenzo[a,d]cycloheptenylidene | |
| 37 | phenyl | phenyl | H | p-tolyl | 4-methyl-1-naphthyl-N | 1 | CH=CH | H | thioxanthenylidene | |
| 38 | phenyl | phenyl | H | p-tolyl | 4-methyl-1-naphthyl-N | 1 | CH=CH | H | N-methyl-acridanylidene | |
| 39 | phenyl | phenyl | H | p-tolyl | 4-methyl-1-naphthyl-N | 1 | CH=CH | —CH₃ | H | phenyl |

TABLE 6-continued

| Compound No. | Ar¹ | Ar² | R¹ | Ar³ | a_m | n | $-(CR^2=CR^3)_n-$ | R⁴ | Ar⁴ | Ar⁵ |
|---|---|---|---|---|---|---|---|---|---|---|
| 40 | phenyl | phenyl | H | p-tolyl | 1-methyl-4-amino-naphthalene | 1 | CH=CH | tolyl | H | tolyl |
| 41 | phenyl | phenyl | H | p-tolyl | 1-methyl-4-amino-naphthalene | 1 | HC=C(CH₂F) | H | H | tolyl |
| 42 | phenyl | phenyl | H | p-tolyl | 1-methyl-4-amino-naphthalene | 1 | HC=C(2-thienyl) | H | H | tolyl |

TABLE 7

| Compound No. | Ar¹ | Ar² | R¹ | Ar³ | a_m | n | −(CR²=CR³)ₙ− | R⁴ | Ar⁴ | Ar⁵ |
|---|---|---|---|---|---|---|---|---|---|---|
| 43 | phenyl | phenyl | H | p-tolyl | 4-methylnaphthalen-1-yl (N-substituted) | 1 | HC=C(CH₂Ph) | H | H | phenyl |
| 44 | phenyl | phenyl | H | p-tolyl | 4-methylnaphthalen-1-yl (N-substituted) | 1 | CH₃−C=CH | H | H | phenyl |
| 45 | phenyl | phenyl | H | p-tolyl | 4-methylnaphthalen-1-yl (N-substituted) | 1 | HC=C(CH₃) | phenyl | H | phenyl |
| 46 | phenyl | phenyl | H | p-tolyl | 4-methylnaphthalen-1-yl (N-substituted) | 2 | CH=CH−CH=CH | H | H | phenyl |

TABLE 7-continued

| Compound No. | Ar¹ | R¹ | Ar³ | [structure]$_m$ | n | $-(CR^2=CR^3)_n-$ | R⁴ | Ar⁴ | Ar⁵ |
|---|---|---|---|---|---|---|---|---|---|
| 47 | phenyl | H | p-tolyl | 1-methylnaphthalen-4-yl (N-linked) | 2 | CH=CH—CH=CH | H | H | 4-methoxyphenyl |
| 48 | phenyl | H | p-tolyl | 1-methylnaphthalen-4-yl (N-linked) | 2 | CH=CH—CH=CH | H | —CH₃ | 4-methoxyphenyl |
| 49 | phenyl | H | p-tolyl | 1-methylnaphthalen-4-yl (N-linked) | 2 | CH=CH—CH=CH | H | —CH₃ | 2-furyl |

TABLE 8

| Compound No. | Ar¹ | Ar² | R¹ | Ar³ | aₘ (core) | n | —(CR²=CR³)ₙ— | R⁴ | Ar⁴ | Ar⁵ |
|---|---|---|---|---|---|---|---|---|---|---|
| 50 | 4-methylphenyl | phenyl | H | 4-methylphenyl | 1-methylnaphthalen-4-yl (N-attached) | 2 | CH=CH—CH=CH | H | —CH₃ | 4-styrylphenyl (stilbene) |
| 51 | 4-methylphenyl | phenyl | H | 4-methylphenyl | 1-methylnaphthalen-4-yl (N-attached) | 2 | CH=CH—CH=CH | H | —CH₃ | 4-(phenylthio)phenyl |
| 52 | 4-methylphenyl | phenyl | H | 4-methylphenyl | 1-methylnaphthalen-4-yl (N-attached) | 2 | $\mathrm{HC{=}C(CH_3){-}CH{=}CH}$ | H | H | phenyl |
| 53 | 4-methylphenyl | phenyl | H | 4-methylphenyl | 1-methylnaphthalen-4-yl (N-attached) | 2 | $\mathrm{HC{=}C(CH_3){-}C(CH_2OCH_3){=}CH}$ | H | H | phenyl |

TABLE 8-continued

| Compound No. | Ar¹ | R¹ | Ar³ | (core structure with n, a_m) | n | —(CR²=CR³)_n— | R⁴ | Ar⁴ | Ar⁵ |
|---|---|---|---|---|---|---|---|---|---|
| 54 | phenyl | H | p-tolyl | 4-methylnaphthyl (N-substituted) | 3 | —(HC=CH)₃— | H | H | phenyl |
| 55 | phenyl | H | p-tolyl | 2-methyl-4-methylnaphthyl (N-substituted, H₃C) | 1 | CH=CH | H | H | phenyl |
| 56 | phenyl | H | p-tolyl | 3-fluoro-4-methylnaphthyl (N-substituted, F) | 1 | CH=CH | H | H | phenyl |

TABLE 9

| Compound No. | Ar¹ | Ar² | R¹ | Ar³ | ─(CR²=CR³)ₙ─ [structure with n, a_m] | n | CR²=CR³ | R⁴ | Ar⁴ | Ar⁵ |
|---|---|---|---|---|---|---|---|---|---|---|
| 57 | phenyl | phenyl | H | 4-methylphenyl | 1-methyl-4-amino-8-methoxynaphthyl | 1 | CH=CH | H | H | phenyl |
| 58 | phenyl | phenyl | H | 4-methylphenyl | 9-methyl-10-amino-1,2,3,4-tetrahydroanthryl | 1 | CH=CH | H | H | phenyl |
| 59 | phenyl | phenyl | H | 4-methylphenyl | 6-methyl-2-aminonaphthyl | 1 | CH=CH | H | H | phenyl |
| 60 | phenyl | phenyl | H | 3-methylphenyl | 6-methyl-2-aminonaphthyl | 1 | CH=CH | H | H | phenyl |

TABLE 9-continued
| Compound No. | Ar¹ | Ar² | R¹ | Ar³ | 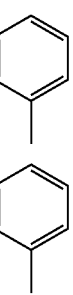 | n | $-(CR^2=CR^3)_n-$ | R⁴ | Ar⁴ | Ar⁵ |
|---|---|---|---|---|---|---|---|---|---|---|
| 61 |  |  | H |  |  | 1 | CH=CH | H | H | 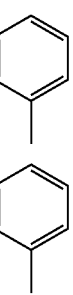 |
| 62 |  |  | H |  |  | 1 | CH=CH | H | H | 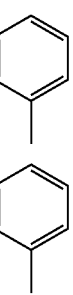 |
| 63 |  |  | H |  |  | 1 | CH=CH | H | —CH₃ | (OCH₃-substituted phenyl) |

TABLE 10

| Compound No. | Ar¹ | Ar² | R¹ | Ar³ | ⟨structure⟩ₐ,ₘ | n | ─(CR²=CR³)ₙ─ | R⁴ | Ar⁴ | Ar⁵ |
|---|---|---|---|---|---|---|---|---|---|---|
| 64 | 4-methylphenyl | 3-methylphenyl | H | 4-methoxyphenyl | 4-methyl-1-naphthyl (N-attached) | 1 | CH=CH | H | H | 4-(N(CH₃)₂)-phenyl with methyl |
| 65 | 4-methylphenyl | 3-methylphenyl | H | 4-methoxyphenyl | 4-methyl-1-naphthyl (N-attached) | 1 | CH=CH | H | H | 4-(CH(CH₃)₂)-phenyl with methyl |
| 66 | 4-methylphenyl | 3-methylphenyl | H | 4-methoxyphenyl | 4-methyl-1-naphthyl (N-attached) | 1 | CH=CH | H | ─CH₃ | 2,4-dimethylphenyl |
| 67 | 4-methylphenyl | 3-methylphenyl | H | 4-methoxyphenyl | 4-methyl-1-naphthyl (N-attached) | 1 | CH=CH | H | H | 3-methylphenyl with CH₃ |

TABLE 10-continued
| Compound No. | Ar¹ | Ar² | R¹ | Ar³ | 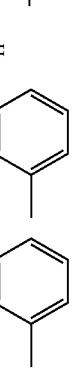 | n | $-(CR^2=CR^3)_n-$ | R⁴ | Ar⁴ | Ar⁵ |
|---|---|---|---|---|---|---|---|---|---|---|
| 68 | 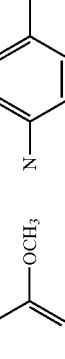 |  | H | 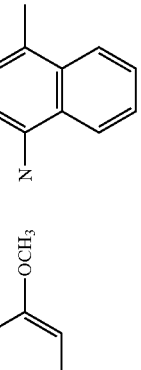 |  | 1 | CH=CH | H | H | 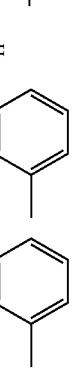 |
| 69 | 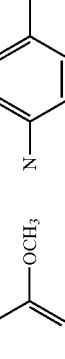 |  | H | 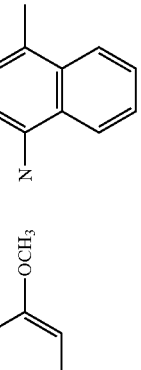 |  | 1 | CH=CH | H | H | 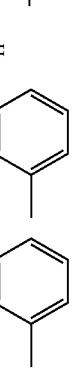 |
| 70 | 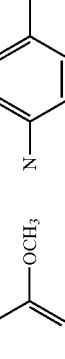 |  | H | 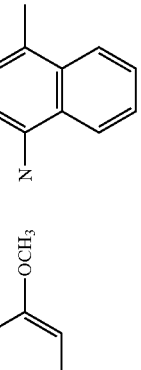 |  | 1 | CH=CH | H | H | |

TABLE 11

| Compound No. | Ar¹ | Ar² | R¹ | Ar³ | $\overset{a_m}{\underset{N}{\bigcirc}}$ | n | $-(CR^2=CR^3)_n-$ | R⁴ | Ar⁴ | Ar⁵ |
|---|---|---|---|---|---|---|---|---|---|---|
| 71 | phenyl(p-methyl) | phenyl | H | phenyl(p-OCH₃) | 4-methylnaphthalen-1-yl | 1 | CH=CH | H | H | 4-methylindanyl |
| 72 | phenyl(p-methyl) | phenyl | H | phenyl(p-OCH₃) | 4-methylnaphthalen-1-yl | 1 | CH=CH | H | H | 6-methylchroman-yl |
| 73 | phenyl(p-methyl) | phenyl | H | phenyl(p-OCH₃) | 4-methylnaphthalen-1-yl | 1 | CH=CH | H | H | 4'-methylbiphenyl |
| 74 | phenyl(p-methyl) | phenyl | H | phenyl(p-OCH₃) | 4-methylnaphthalen-1-yl | 1 | CH=CH | H | H | 4-methylphenyl phenyl sulfide |

TABLE 11-continued

| Compound No. | Ar¹ | R¹ | Ar³ | $\underset{a_m}{\text{[structure]}}$ | n | $-(CR^2=CR^3)_n-$ | R⁴ | Ar⁴ | Ar⁵ |
|---|---|---|---|---|---|---|---|---|---|
| 75 | 4-methylphenyl | H | 4-methoxyphenyl | 4-methylnaphthalen-1-yl | 1 | CH=CH | H | H | 4-(4-methylphenoxy)phenyl |
| 76 | 4-methylphenyl | H | 4-methoxyphenyl | 4-methylnaphthalen-1-yl | 1 | CH=CH | H | H | 4'-phenyl-biphenyl-4-yl |
| 77 | 4-methylphenyl | H | 4-methoxyphenyl | 4-methylnaphthalen-1-yl | 1 | CH=CH | H | H | 4-(2-phenylethenyl)phenyl |

TABLE 12

| Compound No. | Ar¹ | Ar² | R¹ | Ar³ | ⟨structure⟩ₐ,ₙ | n | —(CR²=CR³)ₙ— | R⁴ | Ar⁴ | Ar⁵ |
|---|---|---|---|---|---|---|---|---|---|---|
| 78 | phenyl | tolyl | H | 4-methoxyphenyl | 4-methyl-1-naphthyl (N-linked) | 1 | CH=CH | H | H | 1,4-dimethylnaphthyl |
| 79 | phenyl | tolyl | H | 4-methoxyphenyl | 4-methyl-1-naphthyl (N-linked) | 1 | CH=CH | H | H | 1-methyl-4-methylnaphthyl |
| 80 | phenyl | tolyl | H | 4-methoxyphenyl | 4-methyl-1-naphthyl (N-linked) | 1 | CH=CH | H | H | 6-methoxy-2-methylnaphthyl |
| 81 | phenyl | tolyl | H | 4-methoxyphenyl | 4-methyl-1-naphthyl (N-linked) | 1 | CH=CH | H | H | 10-methylanthryl |

TABLE 12-continued
| Compound No. | Ar¹ | Ar² | R¹ | Ar³ | 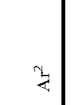 | n | $-(CR^2=CR^3)_n-$ | R⁴ | Ar⁵ |
|---|---|---|---|---|---|---|---|---|---|
| 82 | 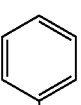 | 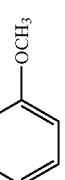 | H |  | 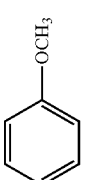 | 1 | CH=CH | H |  |
| 83 | 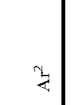 | 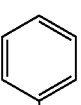 | H | 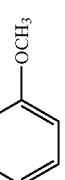 |  | 1 | CH=CH | H | 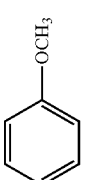 |
| 84 |  | 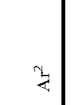 | H | 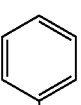 | 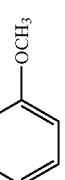 | 1 | CH=CH | H |  |

TABLE 13

| Compound No. | Ar¹ | Ar² | R¹ | Ar³ | (CR²=CR³)ₙ structure | n | CR²=CR³ | R⁴ | Ar⁴ | Ar⁵ |
|---|---|---|---|---|---|---|---|---|---|---|
| 85 | 4-methylphenyl | phenyl | H | 4-methoxyphenyl | 1-methyl-4-amino-naphthyl | 1 | CH=CH | H | —CH₃ | 5-methyl-2-thienyl |
| 86 | 4-methylphenyl | phenyl | H | 4-methoxyphenyl | 1-methyl-4-amino-naphthyl | 1 | CH=CH | H | —CH₃ | 2-benzothiazolyl |
| 87 | 4-methylphenyl | phenyl | H | 4-methoxyphenyl | 1-methyl-4-amino-naphthyl | 1 | CH=CH | H | —CH₃ | 9-ethyl-3-carbazolyl |
| 88 | 4-methylphenyl | phenyl | H | 4-methoxyphenyl | 1-methyl-4-amino-naphthyl | 1 | CH=CH | H | phenyl | phenyl |

TABLE 13-continued

| Compound No. | Ar¹ | Ar² | R¹ | Ar³ | ![structure] | n | $(CR^2=CR^3)_n$ | R⁴ | Ar⁴ | Ar⁵ |
|---|---|---|---|---|---|---|---|---|---|---|
| 89 | 4-methylphenyl | phenyl | H | 4-methoxyphenyl | 1-methyl-4-N-naphthyl | 1 | CH=CH | H | 4-methylphenyl | 4-methylphenyl |
| 90 | 4-methylphenyl | phenyl | H | 4-methoxyphenyl | 1-methyl-4-N-naphthyl | 1 | CH=CH | H | 4-methoxyphenyl | 4-methoxyphenyl |
| 91 | 4-methylphenyl | phenyl | H | 4-methoxyphenyl | 1-methyl-4-N-naphthyl | 1 | CH=CH | H | 4-(N(CH₃)₂)phenyl | 4-(N(CH₃)₂)phenyl |

TABLE 14

| Compound No. | Ar¹ | Ar² | R¹ | Ar³ | ⟨structure⟩ₐₘ | n | —(CR²=CR³)ₙ— | R⁴ | Ar⁴ | Ar⁵ |
|---|---|---|---|---|---|---|---|---|---|---|
| 92 | phenyl | phenyl | H | 4-methoxyphenyl | 4-methylnaphthalen-1-yl | 1 | CH=CH | H | phenyl | benzyl |
| 93 | phenyl | phenyl | H | 4-methoxyphenyl | 4-methylnaphthalen-1-yl | 1 | CH=CH | H | phenyl | 2-thienylmethyl |
| 94 | phenyl | phenyl | H | 4-methoxyphenyl | 4-methylnaphthalen-1-yl | 1 | CH=CH | H | phenyl | 3,4-dihydronaphthalen-1(2H)-ylidenemethyl |
| 95 | phenyl | phenyl | H | 4-methoxyphenyl | 4-methylnaphthalen-1-yl | 1 | CH=CH | H | phenyl | anthracen-9(10H)-ylidenemethyl |

TABLE 14-continued

| Compound No. | Ar¹ | Ar² | R¹ | Ar³ | ⟨N-aₘ⟩ | n | -(CR²=CR³)ₙ- | R⁴ | Ar⁴ | Ar⁵ |
|---|---|---|---|---|---|---|---|---|---|---|
| 96 | phenyl | phenyl | H | 4-methoxyphenyl | 4-methyl-1-naphthyl | 1 | CH=CH | H | | dibenzosuberylidene |
| 97 | phenyl | phenyl | H | 4-methoxyphenyl | 4-methyl-1-naphthyl | 1 | CH=CH | H | | xanthylidene |
| 98 | phenyl | phenyl | H | 4-methoxyphenyl | 4-methyl-1-naphthyl | 1 | CH=CH | H | | N-methylacridylidene |

TABLE 15

| Compound No. | Ar¹ | Ar² | R¹ | Ar³ | a_m | n | —(CR²=CR³)_n— | R⁴ | Ar⁴ | Ar⁵ |
|---|---|---|---|---|---|---|---|---|---|---|
| 99 | phenyl | phenyl | H | 4-methoxyphenyl | 4-methylnaphth-1-yl | 1 | CH=CH | —CH₃ | H | phenyl |
| 100 | phenyl | phenyl | H | 4-methoxyphenyl | 4-methylnaphth-1-yl | 1 | CH=CH | phenyl | H | phenyl |
| 101 | phenyl | phenyl | H | 4-methoxyphenyl | 4-methylnaphth-1-yl | 1 | HC=C(CH₂F) | H | H | phenyl |
| 102 | phenyl | phenyl | H | 4-methoxyphenyl | 4-methylnaphth-1-yl | 1 | HC=C(2-thienyl) | H | H | phenyl |

TABLE 15-continued

| Compound No. | Ar¹ | Ar² | R¹ | Ar³ | (structure)ₐₘ | n | ─(CR²=CR³)ₙ─ | R⁴ | Ar⁴ | Ar⁵ |
|---|---|---|---|---|---|---|---|---|---|---|
| 103 | phenyl | phenyl | H | 4-methoxyphenyl | 4-methyl-1-naphthyl (N-attached) | 1 | HC=C-CH₂-phenyl | H | H | phenyl |
| 104 | phenyl | phenyl | H | 4-methoxyphenyl | 4-methyl-1-naphthyl (N-attached) | 1 | CH₃-C=CH | H | H | phenyl |
| 105 | phenyl | phenyl | H | 4-methoxyphenyl | 4-methyl-1-naphthyl (N-attached) | 1 | CH₃-C=CH | phenyl | H | phenyl |

TABLE 16

| Compound No. | Ar¹ | Ar² | R¹ | Ar³ | ![structure] | n | $-(CR^2=CR^3)_n-$ | R⁴ | Ar⁴ | Ar⁵ |
|---|---|---|---|---|---|---|---|---|---|---|
| 106 | phenyl | phenyl | H | 4-methoxyphenyl | 4-methylnaphthalen-1-yl (N) | 2 | CH=CH—CH=CH | H | H | 4-methylphenyl |
| 107 | phenyl | phenyl | H | 4-methoxyphenyl | 4-methylnaphthalen-1-yl (N) | 2 | CH=CH—CH=CH | H | H | 4-methoxyphenyl |
| 108 | phenyl | phenyl | H | 4-methoxyphenyl | 4-methylnaphthalen-1-yl (N) | 2 | CH=CH—CH=CH | H | —CH₃ | 4-methoxyphenyl |
| 109 | phenyl | phenyl | H | 4-methoxyphenyl | 4-methylnaphthalen-1-yl (N) | 2 | CH=CH—CH=CH | H | —CH₃ | 4-biphenylyl |

TABLE 16-continued
| Compound No. | Ar¹ | Ar² | R¹ | Ar³ | 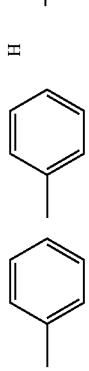 | n | $-(CR^2=CR^3)_n-$ | $R^4$ | $Ar^4$ | $Ar^5$ |
|---|---|---|---|---|---|---|---|---|---|---|
| 110 | 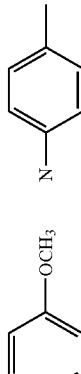 | 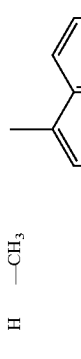 | H |  | 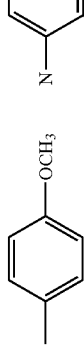 | 2 | CH=CH—CH=CH | H | —CH₃ | 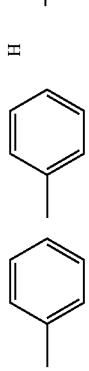 |
| 111 | 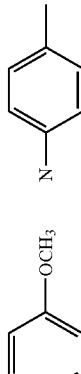 | 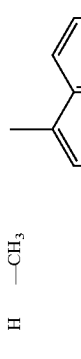 | H |  | 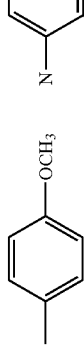 | 2 | CH=CH—CH=CH | H | —CH₃ | 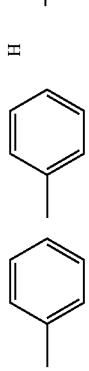 |
| 112 | 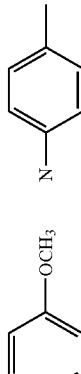 | 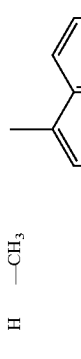 | H |  | 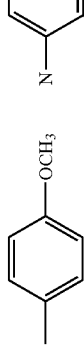 | 2 | CH=CH—CH=CH | H | H | |

TABLE 17

| Compound No. | Ar¹ | Ar² | R¹ | Ar³ | | n | -(CR²=CR³)ₙ- | R⁴ | Ar⁴ | Ar⁵ |
|---|---|---|---|---|---|---|---|---|---|---|
| 113 | phenyl | phenyl | H | 4-OCH₃-phenyl | (cyclophane with N) | | | | | phenyl |
| 114 | phenyl | phenyl | H | 4-OCH₃-phenyl | 4-methyl-1-naphthyl(N) | 2 | CH₃-C(=CH-CH=CH)- with HC= | H | H | phenyl |
| 115 | phenyl | phenyl | H | 4-OCH₃-phenyl | 4-methyl-1-naphthyl(N) | 2 | CH₃-C(=CH-CH=CH)-CH₂OCH₃ with HC= | H | H | phenyl |
| 116 | phenyl | phenyl | H | 4-OCH₃-phenyl | 4-methyl-1-naphthyl(N) | 3 | -(HC=CH)₃- | H | H | phenyl |
| | phenyl | phenyl | H | 4-OCH₃-phenyl | 4-methyl-3-methyl-1-naphthyl(N) | 1 | CH=CH | H | H | phenyl |

TABLE 17-continued

| Compound No. | Ar¹ | Ar² | R¹ | Ar³ | (structure) | n | $-(CR^2=CR^3)_n-$ | R⁴ | Ar⁴ | Ar⁵ |
|---|---|---|---|---|---|---|---|---|---|---|
| 117 | phenyl | phenyl | H | 4-methoxyphenyl | 2-fluoro-1-methyl-4-amino-naphthalene | 1 | CH=CH | H | H | phenyl |
| 118 | phenyl | phenyl | H | 4-methoxyphenyl | 1-methoxy-4-methyl-5-amino-naphthalene (OCH₃) | 1 | CH=CH | H | H | phenyl |
| 119 | phenyl | phenyl | H | 4-methoxyphenyl | 9-methyl-10-amino-1,2,3,4-tetrahydroanthracene | 1 | CH=CH | H | H | phenyl |

TABLE 18

TABLE 18-continued

| Compound No. | Ar¹ | Ar² | R¹ | Ar³ | (structure) | n | $(CR^2=CR^3)_n$ | R⁴ | Ar⁴ | Ar⁵ |
|---|---|---|---|---|---|---|---|---|---|---|
| 124 | phenyl | phenyl | H | phenyl | 1-methylnaphthalen-4-yl (N-linked) | 1 | CH=CH | H | phenyl | phenyl |
| 125 | phenyl | phenyl | H | 4-N(CH₃)₂-phenyl | 1-methylnaphthalen-4-yl (N-linked) | 1 | CH=CH | H | H | phenyl |
| 126 | phenyl | phenyl | H | 4-CF₃-phenyl | 1-methylnaphthalen-4-yl (N-linked) | 1 | CH=CH | H | H | 4-OCH₃-phenyl |

TABLE 19

| Compound No. | Ar¹ | Ar² | R¹ | Ar³ | (structure) | n | —(CR²=CR³)ₙ— | R⁴ | Ar⁴ | Ar⁵ |
|---|---|---|---|---|---|---|---|---|---|---|
| 127 | phenyl | phenyl | H | 4-isopropylphenyl | 4-methyl-1-naphthyl (N) | 1 | CH=CH | H | phenyl | phenyl |
| 128 | phenyl | phenyl | H | 2-methylphenyl | 4-methyl-1-naphthyl (N) | 1 | CH=CH | H | H | phenyl |
| 129 | phenyl | phenyl | H | 3-methylphenyl | 4-methyl-1-naphthyl (N) | 1 | CH=CH | H | H | 4-methoxyphenyl |
| 130 | phenyl | phenyl | H | 2-fluorophenyl | 4-methyl-1-naphthyl (N) | 1 | CH=CH | H | phenyl | phenyl |

TABLE 19-continued

| Compound No. | Ar¹ | R¹ | Ar³ | [structure] | n | $-(CR^2=CR^3)_n-$ | R⁴ | Ar⁴ | Ar⁵ |
|---|---|---|---|---|---|---|---|---|---|
| 131 | [phenyl with CH₃] | H | [dimethylphenyl] | [naphthyl-N] | 1 | CH=CH | H | H | [phenyl with CH₃] |
| 132 | [phenyl with CH₃] | H | [dimethoxyphenyl] | [naphthyl-N] | 1 | CH=CH | H | —CH₃ | [phenyl with OCH₃ and CH₃] |
| 133 | [phenyl with CH₃] | H | [dimethoxyphenyl] | [naphthyl-N] | 1 | CH=CH | H | [phenyl] | [phenyl with CH₃] |

TABLE 20
| Compound No. | Ar¹ | Ar² | R¹ | Ar³ |  | n | —(CR²=CR³)ₙ— | R⁴ | Ar⁴ | Ar⁵ |
|---|---|---|---|---|---|---|---|---|---|---|
| 134 | 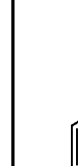 | 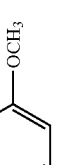 | H |  | 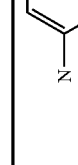 | 1 | CH=CH | H | H | 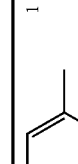 |
| 135 |  | 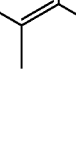 | H | 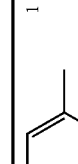 |  | 1 | CH=CH | H | H |  |
| 136 |  |  | H |  |  | 1 | CH=CH | H |  | |
| 137 |  |  | H |  |  | 1 | CH=CH | H | H |  |

TABLE 20-continued

| Compound No. | Ar¹ | Ar² | R¹ | Ar³ | [structure] | n | $-(CR^2=CR^3)_n-$ | R⁴ | Ar⁴ | Ar⁵ |
|---|---|---|---|---|---|---|---|---|---|---|
| 138 | phenyl | phenyl | H | biphenyl | 1-methyl-4-N naphthyl | 1 | CH=CH | H | —CH₃ | 4-methoxyphenyl |
| 139 | phenyl | phenyl | H | biphenyl | 1-methyl-4-N naphthyl | 1 | CH=CH | H | phenyl | phenyl |
| 140 | phenyl | phenyl | H | 4-methylphenyl-O-phenyl | 1-methyl-4-N naphthyl | 1 | CH=CH | H | H | phenyl |

TABLE 21

| Compound No. | Ar¹ | Ar² | R¹ | Ar³ | ⟨CR²=CR³⟩ₙ structure | n | (CR²=CR³) | R⁴ | Ar⁴ | Ar⁵ |
|---|---|---|---|---|---|---|---|---|---|---|
| 141 | phenyl | phenyl | H | 4-(4-methylphenoxy)phenyl | 1-methyl-4-aminonaphthyl | 1 | CH=CH | H | H | 4-methoxyphenyl |
| 142 | phenyl | phenyl | H | 4-(4-methylphenoxy)phenyl | 1-methyl-4-aminonaphthyl | 1 | CH=CH | H | —CH₃ | 2-methylthienyl |
| 143 | phenyl | phenyl | H | 4-(phenylthio)-4'-methylphenyl | 1-methyl-4-aminonaphthyl | 1 | CH=CH | H | H | phenyl |
| 144 | phenyl | phenyl | H | 3,5-dimethyl-4-methyl-(phenylthio)phenyl | 1-methyl-4-aminonaphthyl | 1 | CH=CH | H | —CH₃ | 4-methoxyphenyl |

TABLE 21-continued

| Compound No. | Ar¹ | R¹ | Ar² | Ar³ | (CR²=CR³)ₙ structure | n | CR²=CR³ | R⁴ | Ar⁴ | Ar⁵ |
|---|---|---|---|---|---|---|---|---|---|---|
| 145 | 4-methylphenyl | H | phenyl | 4'-methyl-biphenyl-4-yl | 4-methyl-1-naphthyl (N-linked) | 1 | CH=CH | H | —CH₃ | 2-furyl |
| 146 | 4-methylphenyl | H | phenyl | 1-methylnaphthyl | 4-methyl-1-naphthyl (N-linked) | 1 | CH=CH | H | H | phenyl |
| 147 | 4-methylphenyl | H | phenyl | 1-methylnaphthyl | 4-methyl-1-naphthyl (N-linked) | 1 | CH=CH | H | —CH₃ | 4-methoxyphenyl |

TABLE 22

| Compound No. | Ar¹ | Ar² | R¹ | Ar³ | | n | ─(CR²=CR³)ₙ─ | R⁴ | Ar⁴ | Ar⁵ |
|---|---|---|---|---|---|---|---|---|---|---|
| 148 | phenyl | phenyl | H | 1-methylnaphthyl | 4-methyl-1-aminonaphthyl | 1 | CH=CH | H | H | 4-methylphenyl |
| 149 | phenyl | phenyl | H | 1-methylnaphthyl | 4-methyl-1-aminonaphthyl | 1 | CH=CH | H | —CH₃ | 4-isopropylphenyl |
| 150 | phenyl | phenyl | H | 1-methylnaphthyl | 4-methyl-1-aminonaphthyl | 1 | CH=CH | H | H | 2-fluoro-methylphenyl |
| 151 | phenyl | phenyl | H | 1-methylnaphthyl | 4-methyl-1-aminonaphthyl | 1 | CH=CH | H | —CH₃ | methylchromanyl |

TABLE 22-continued
| Compound No. | Ar¹ | Ar² | R¹ | Ar³ | 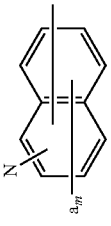 | n | $-(CR^2=CR^3)_n-$ | R⁴ | Ar⁴ | Ar⁵ |
|---|---|---|---|---|---|---|---|---|---|---|
| 152 | 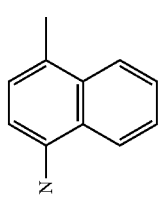 | 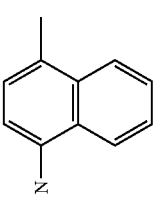 | H | 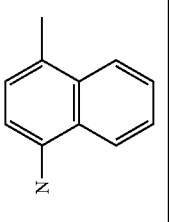 | | 1 | CH=CH | H | —CH₃ |  |
| 153 | 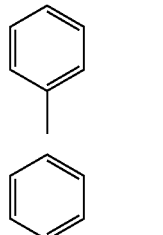 | 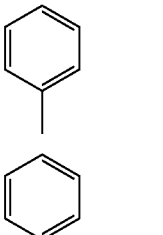 | H | 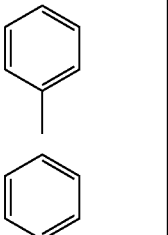 | | 1 | CH=CH | H | —CH₃ | 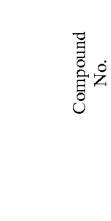 |
| 154 |  | 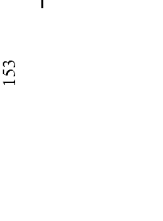 | H |  | | 1 | CH=CH | H | H |  |

TABLE 23

| Compound No. | Ar¹ | Ar² | R¹ | Ar³ | (structure) n | —(CR²=CR³)ₙ— | R⁴ | Ar⁴ | Ar⁵ |
|---|---|---|---|---|---|---|---|---|---|
| 155 | p-tolyl | phenyl | H | 1-methylnaphthyl | 4-methyl-1-aminonaphthyl | 1 | CH=CH | H | —CH₃ | 1-naphthyl |
| 156 | p-tolyl | phenyl | H | 1-methylnaphthyl | 4-methyl-1-aminonaphthyl | 1 | CH=CH | H | —CH₃ | pyrenyl |
| 157 | p-tolyl | phenyl | H | 1-methylnaphthyl | 4-methyl-1-aminonaphthyl | 1 | CH=CH | H | —CH₃ | 2-thienyl |
| 158 | p-tolyl | phenyl | H | 1-methylnaphthyl | 4-methyl-1-aminonaphthyl | 1 | CH=CH | H | H | 2-furyl |

TABLE 23-continued

| Compound No. | Ar¹ | Ar² | R¹ | Ar³ | [structure with N, a_m] | n | $-(CR^2=CR^3)_n-$ | R⁴ | Ar⁴ | Ar⁵ |
|---|---|---|---|---|---|---|---|---|---|---|
| 159 | 4-methylphenyl | phenyl | H | 1-methylnaphthyl | 4-methyl-1-naphthyl-N | 1 | CH=CH | H | phenyl | phenyl |
| 160 | 4-methylphenyl | phenyl | H | 1-methylnaphthyl | 4-methyl-1-naphthyl-N | 1 | CH=CH | H | 4-methylphenyl | 4-methylphenyl |
| 161 | 4-methylphenyl | phenyl | H | 1-methylnaphthyl | 4-methyl-1-naphthyl-N | 1 | CH=CH | H | 2-thienylethyl | phenyl |

TABLE 24

| Compound No. | Ar¹ | Ar² | R¹ | Ar³ | (structure) | n | ‒(CR²=CR³)ₙ‒ | R⁴ | Ar⁴ | Ar⁵ |
|---|---|---|---|---|---|---|---|---|---|---|
| 162 | phenyl | phenyl | H | methylnaphthyl | methylnaphthyl-N | 1 | CH=CH | H | H | dihydronaphthylidene |
| 163 | phenyl | phenyl | H | methylnaphthyl | methylnaphthyl-N | 1 | CH=CH | H | H | dibenzocycloheptenylidene |
| 164 | phenyl | phenyl | H | methylnaphthyl | methylnaphthyl-N | 1 | CH=CH | H | H | N-methyl acridinylidene |
| 165 | phenyl | phenyl | H | methylnaphthyl | methylnaphthyl-N | 2 | CH=CH−CH=CH | H | H | phenyl |

TABLE 24-continued

| Compound No. | Ar¹ | Ar² | R¹ | Ar³ | [structure] | n | $-(CR^2=CR^3)_n-$ | R⁴ | Ar⁴ | Ar⁵ |
|---|---|---|---|---|---|---|---|---|---|---|
| 166 | phenyl | phenyl | H | methylnaphthyl | methylnaphthyl-N | 2 | CH=CH—CH=CH | H | —CH₃ | 4-methoxyphenyl |
| 167 | phenyl | furyl | H | methylnaphthyl | methylnaphthyl-N | 2 | CH=CH—CH=CH | H | —CH₃ | 2-methylfuryl |
| 168 | phenyl | phenyl | H | methylnaphthyl | methylnaphthyl-N | 3 | —(HC=CH)₃— | H | H | phenyl |

TABLE 25

| Compound No. | Ar¹ | Ar² | R¹ | Ar³ | [structure] | n | $-(CR^2=CR^3)_n-$ | R⁴ | Ar⁴ | Ar⁵ |
|---|---|---|---|---|---|---|---|---|---|---|
| 169 | phenyl | phenyl | H | 1-methylnaphthyl | 1-methylnaphthyl-N | 1 | CH=CH | H | H | phenyl |
| 170 | phenyl | phenyl | H | 1,4-dimethylnaphthyl | 1-methylnaphthyl-N | 1 | CH=CH | H | H | phenyl |
| 171 | phenyl | phenyl | H | 1,2-dimethylnaphthyl | 1-methylnaphthyl-N | 1 | CH=CH | H | H | phenyl |
| 172 | phenyl | phenyl | H | 1,4-dimethylnaphthyl | 1-methylnaphthyl-N | 1 | CH=CH | H | H | phenyl |

TABLE 25-continued

| Compound No. | Ar¹ | Ar² | R¹ | Ar³ | ![ring] | n | $-(CR^2=CR^3)_n-$ | R⁴ | Ar⁴ | Ar⁵ |
|---|---|---|---|---|---|---|---|---|---|---|
| 173 | phenyl | phenyl | H | 4-methoxy-1-naphthyl (with methyl) | 4-methyl-1-naphthyl(N) | 1 | CH=CH | H | H | phenyl |
| 174 | phenyl | phenyl | H | 1-methoxy-4-methyl-naphthyl (with CH₃) | 4-methyl-1-naphthyl(N) | 1 | CH=CH | H | H | phenyl |
| 175 | phenyl | phenyl | H | 6-methyl-2-naphthyl | 4-methyl-1-naphthyl(N) | 1 | CH=CH | H | H | phenyl |

TABLE 26

| Compound No. | Ar¹ | Ar² | R¹ | Ar³ | ⟨a_m⟩ (N-containing ring) | n | —(CR²=CR³)_n— | R⁴ | Ar⁴ | Ar⁵ |
|---|---|---|---|---|---|---|---|---|---|---|
| 176 | 3-methylphenyl | phenyl | H | 2-methyl-5-thienyl | 4-methylnaphthalen-1-yl (N-attached) | 1 | CH=CH | H | H | phenyl |
| 177 | 3-methylphenyl | phenyl | H | 2-methyl-5-thienyl | 4-methylnaphthalen-1-yl (N-attached) | 1 | CH=CH | H | H | 4-methoxyphenyl |
| 178 | 3-methylphenyl | phenyl | H | 2-methyl-5-thienyl | 4-methylnaphthalen-1-yl (N-attached) | 1 | CH=CH | H | phenyl | phenyl |
| 179 | 3-methylphenyl | phenyl | H | 2-methyl-5-furyl | 4-methylnaphthalen-1-yl (N-attached) | 1 | CH=CH | H | H | phenyl |

TABLE 26-continued

| Compound No. | Ar¹ | Ar² | R¹ | Ar³ | a_m structure | n | $-(CR^2=CR^3)_n-$ | R⁴ | Ar⁴ | Ar⁵ |
|---|---|---|---|---|---|---|---|---|---|---|
| 180 | 4-methylphenyl | phenyl | H | 2,5-dimethylfuran | N-methylnaphthyl | 1 | CH=CH | H | —CH₃ | 4-methoxyphenyl |
| 181 | 4-methylphenyl | phenyl | H | 2,5-dimethylfuran | N-methylnaphthyl | 1 | CH=CH | H | phenyl | phenyl |
| 182 | 4-methylphenyl | phenyl | H | 3-methylbenzothiophene | N-methylnaphthyl | 1 | CH=CH | H | H | phenyl |

TABLE 27
| Compound No. | Ar¹ | Ar² | R¹ | Ar³ | (CR²=CR³)ₙ structure | n | CR²=CR³ | R⁴ | Ar⁴ | Ar⁵ |
|---|---|---|---|---|---|---|---|---|---|---|
| 183 | 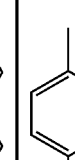 | 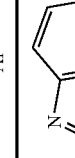 | H | 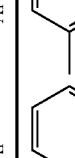 2-methyl-6-methylbenzothiazole |  1-methyl-4-N naphthalene | 1 | CH=CH | H | —CH₃ |  p-OCH₃ phenyl |
| 184 | 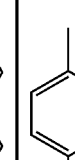 | 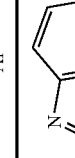 | H | 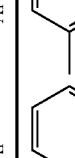 3,6-dimethyl-9-ethylcarbazole |  1-methyl-4-N naphthalene | 1 | CH=CH | H |  phenyl | 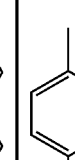 phenyl |
| 185 | 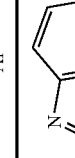 | 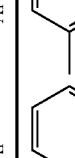 | H |  6-methyl-tetrahydronaphthalene |  1-methyl-4-N naphthalene | 1 | CH=CH | H | H | 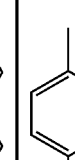 phenyl |
| 186 | 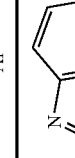 | 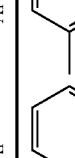 | H |  4-methoxy-ethylphenyl |  1-methyl-4-N naphthalene | 1 | CH=CH | H | H | p-OCH₃ phenyl |

TABLE 27-continued

| Compound No. | Ar¹ | Ar² | R¹ | Ar³ | [structure with N, a_m] | n | —(CR²=CR³)_n— | R⁴ | Ar⁴ | Ar⁵ |
|---|---|---|---|---|---|---|---|---|---|---|
| 187 | phenyl | phenyl | H | cyclohexyl | 1-methyl-4-amino-naphthyl | 1 | CH=CH | H | tolyl | phenyl |
| 188 | phenyl | phenyl | H | 2,5-dimethylthiophene | 1-methyl-4-amino-naphthyl | 0 | — | H | H | phenyl |
| 189 | phenyl | phenyl | H | 2,5-dimethylthiophene | 1-methyl-4-amino-naphthyl | 0 | — | H | H | 4-methylphenyl |

TABLE 28

| Compound No. | Ar¹ | Ar² | R¹ | Ar³ | (structure) | n | $-(CR^2=CR^3)_n-$ | R⁴ | Ar⁴ | Ar⁵ |
|---|---|---|---|---|---|---|---|---|---|---|
| 190 | 4-methylphenyl | phenyl | H | 2,5-dimethylthiophene | 1-methyl-4-amino-naphthalene | 0 | — | H | H | 4-methoxyphenyl |
| 191 | 4-methylphenyl | phenyl | H | 2,5-dimethylthiophene | 1-methyl-4-amino-naphthalene | 0 | — | H | H | 1-methoxy-4-methylnaphthalene |
| 192 | 4-methylphenyl | phenyl | H | 2,5-dimethylthiophene | 1-methyl-4-amino-naphthalene | 0 | — | H | H | 2-thienyl |
| 193 | 4-methylphenyl | phenyl | H | 2,5-dimethylthiophene | 1-methyl-4-amino-naphthalene | 0 | — | H | H | (E)-4-methylstilbenyl |

TABLE 28-continued

| Compound No. | Ar¹ | R¹ | Ar³ | [structure] n —(CR²=CR³)ₙ— R⁴ | Ar⁴ | Ar⁵ |
|---|---|---|---|---|---|---|---|---|
| 194 | biphenyl | H | 2,5-dimethylthiophene | 4-methylnaphthyl-N | 0 | — | H | phenyl | phenyl |
| 195 | biphenyl | H | 2-methylfuran | 4-methylnaphthyl-N | 0 | — | H | H | phenyl |
| 196 | biphenyl | H | 2-methylfuran | 4-methylnaphthyl-N | 0 | — | H | H | 4-methylphenyl |

TABLE 29

| Compound No. | Ar¹ | Ar² | R¹ | Ar³ | $\begin{array}{c}\text{structure}\\\text{with }a_m\end{array}$ | n | $-(CR^2=CR^3)_n-$ | R⁴ | Ar⁴ | Ar⁵ |
|---|---|---|---|---|---|---|---|---|---|---|
| 197 | 4-methylphenyl | phenyl | H | 2-methylfuryl | 1-methyl-4-N-naphthyl | 0 | — | H | H | 4-methoxyphenyl (with p-CH₃) |
| 198 | 4-methylphenyl | phenyl | H | 2-methylfuryl | 1-methyl-4-N-naphthyl | 0 | — | H | H | 4-N(CH₃)₂-phenyl (with p-CH₃) |
| 199 | 4-methylphenyl | phenyl | H | 2-methylfuryl | 1-methyl-4-N-naphthyl | 0 | — | H | H | 4-methylbiphenyl |
| 200 | 4-methylphenyl | phenyl | H | 2-methylfuryl | 1-methyl-4-N-naphthyl | 0 | — | H | H | 1-methylnaphthyl |

TABLE 29-continued
| Compound No. | Ar¹ | Ar² | R¹ | Ar³ | (structure with a_m, N) | n | -(CR²=CR³)- | R⁴ | Ar⁴ | Ar⁵ |
|---|---|---|---|---|---|---|---|---|---|---|
| 201 | 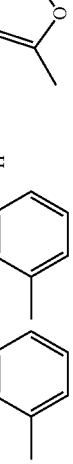 |  | H | 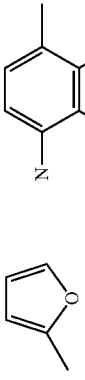 |  | 0 | — | H | 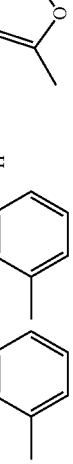 |  |
| 202 | 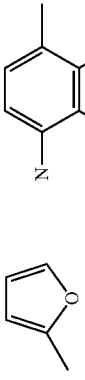 |  | H | 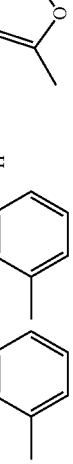 |  | 0 | — | H | 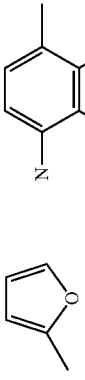 |  |
| 203 | | | H | | | 0 | — | H | H | |

TABLE 30
| Compound No. | Ar¹ | R¹ | Ar³ | 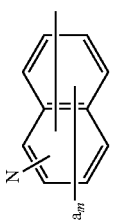 | n | -(CR²=CR³)ₙ- | R⁴ | Ar⁴ | Ar⁵ |
|---|---|---|---|---|---|---|---|---|---|
| 204 | 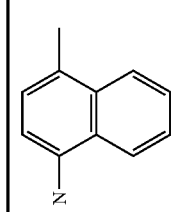 | H | 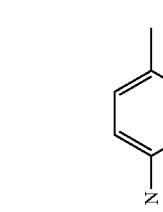 | 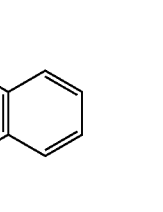 | 0 | — | H | H | 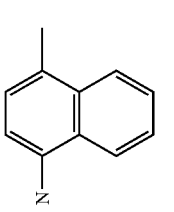 |
| 205 | 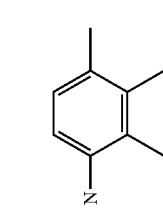 | H |  | 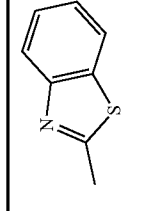 | 0 | — | H | 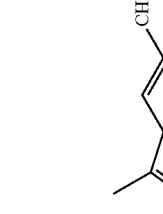 | 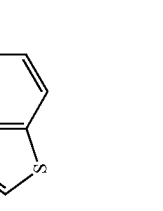 |
| 206 | 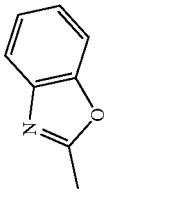 | H | 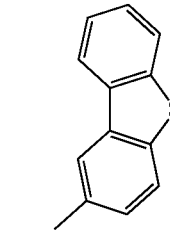 |  | 0 | — | H | H | 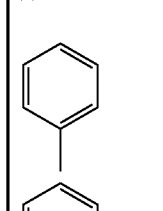 |
| 207 | 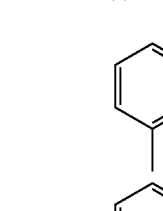 | H | 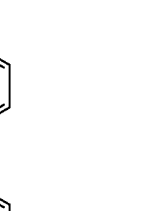 | 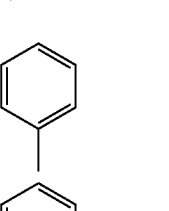 | 0 | — | H | H | 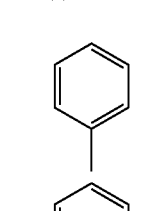 |

TABLE 30-continued

| Compound No. | Ar¹ | R¹ | Ar³ | (structure) aₘ | n | —(CR²=CR³)ₙ— | R⁴ | Ar⁴ | Ar⁵ |
|---|---|---|---|---|---|---|---|---|---|
| 208 | (4-methylphenyl) | H | (2-methyldibenzofuran) | (1-amino-4-methylnaphthyl) | 0 | — | H | (methylphenyl) | (phenyl) |
| 209 | (4-methylphenyl) | CH₃ | (4-methoxyphenyl-methyl) | (1-amino-4-methylnaphthyl) | 1 | CH=CH | H | H | (phenyl) |
| 210 | (4-methylphenyl) | CH₂CF₃ | (4-methoxyphenyl-methyl) | (1-amino-4-methylnaphthyl) | 1 | CH=CH | H | H | (phenyl) |

TABLE 31

| Compound No. | Ar¹ | Ar² | R¹ | Ar³ | $-\!\!\left(CR^2\!\!=\!\!CR^3\right)_{\!n}\!\!-$ | | R⁴ | Ar⁵ |
|---|---|---|---|---|---|---|---|---|
| | | | | | n | CR²=CR³ | | |
| 211 | phenyl | phenyl | CH(CH₃)₂ | 4-OCH₃-phenyl | 4-methyl-naphthyl | 1 | CH=CH | H | phenyl |
| 212 | phenyl | phenyl | F | 4-OCH₃-phenyl | 4-methyl-naphthyl | 1 | CH=CH | H | phenyl |
| 213 | 4-CH₃-phenyl | 4-CH₃-phenyl | H | 4-OCH₃-phenyl | 4-methyl-naphthyl | 1 | CH=CH | H | phenyl |
| 214 | 4-OCH₃-phenyl | 4-OCH₃-phenyl | H | 4-OCH₃-phenyl | 4-methyl-naphthyl | 1 | CH=CH | H | phenyl |

TABLE 31-continued
| Compound No. | Ar¹ | Ar² | R¹ | Ar³ | 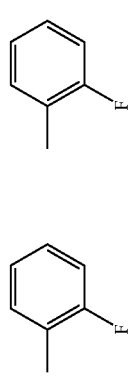 | n | —(CR²=CR³)ₙ— | R⁴ | Ar⁴ | Ar⁵ |
|---|---|---|---|---|---|---|---|---|---|---|
| 215 |  | 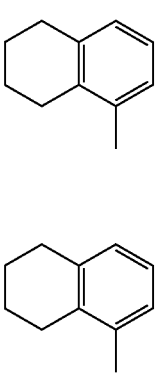 | H |  |  | 1 | CH=CH | H | H | 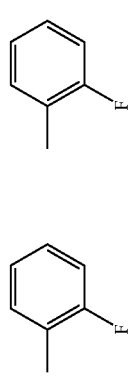 |
| 216 |  | 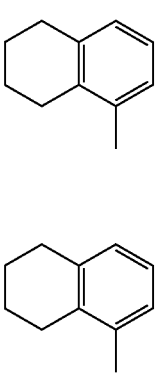 | H |  |  | 1 | CH=CH | H | H | 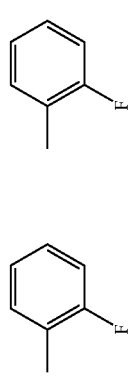 |
| 217 |  | 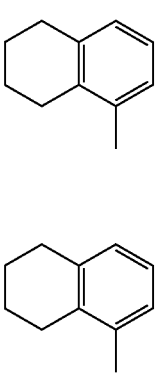 | H |  |  | 1 | CH=CH | H | H | 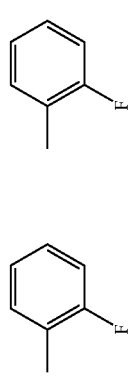 |

TABLE 32

| Compound No. | Ar¹ | Ar² | R¹ | Ar³ | $\underset{a_m}{\underset{}{N}}$ (naphthyl-N group) |
|---|---|---|---|---|---|
| 218 | 1-methylnaphthyl | 1-methylnaphthyl | H | 4-methoxyphenyl | N-(4-methylnaphthyl) |
| 219 | 2-methylbenzothiazolyl | 2-methylbenzothiazolyl | H | 4-methoxyphenyl | N-(4-methylnaphthyl) |
| 220 | 2-methylthienyl | phenyl | H | 4-methoxyphenyl | N-(4-methylnaphthyl) |

| Compound No. | n | $-(CR^2=CR^3)_n-$ | $R^4$ | $Ar^4$ | $Ar^5$ |
|---|---|---|---|---|---|
| 218 | 1 | CH=CH | H | H | phenyl |
| 219 | 1 | CH=CH | H | H | phenyl |
| 220 | 1 | CH=CH | H | H | phenyl |

The enamine compound represented by formula (1) may be produced, for example, as follows:

First, an aldehyde compound or a ketone compound represented by formula (3) is reacted with a secondary amine compound represented by formula (4) through dehydrating condensation to give an enamine intermediate represented by formula (5):

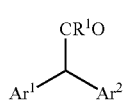

(3)

wherein Ar¹, Ar² and R¹ represent the same meanings as those defined in formula (1).

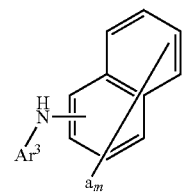

(4)

wherein Ar³, a and m represent the same as those defined in formula (1).

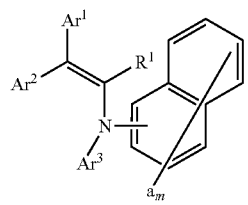

(5)

wherein Ar¹, Ar², Ar³, R¹, a and m represent the same as those defined in formula (1).

The dehydrating condensation is effected, for example, as follows: an aldehyde or ketone compound represented by formula (3) and a secondary amine compound represented by formula (4) are, approximately in a ratio of 1/1 by mol, dissolved in a solvent of, for example, aromatic solvents, alcohols or ethers to prepare a solution. Specific examples of the usable solvent are toluene, xylene, chlorobenzene, butanol and diethylene glycol dimethyl ether. To the thus-prepared solution, added is a catalyst, for example, an acid catalyst such as p-toluenesulfonic acid, camphorsulfonic acid or pyridinium-p-toluenesulfonate acid, and reacted under heat. The amount of the catalyst to be added is preferably in a ratio by molar equivalent of from 1/10 to 1/1000 to the amount of the aldehyde or ketone compound represented by formula (3), more preferably from 1/25 to 1/500, most preferably from 1/50 to 1/200. During the reaction, water is formed and it interferes with the reaction. Therefore, the water formed is removed out of the system through azeotropic evaporation with the solvent used. As a result, the enamine intermediate represented by formula (5) is produced at high yield.

The enamine intermediate represented by formula (5) is formylated through Vilsmeier reaction or is acylated through Friedel-Crafts reaction to give an enamine-carbonyl intermediate of the following general formula (6). The formylation through Vilsmeier reaction gives an enamine-aldehyde intermediate, a type of enamine-carbonyl intermediate represented by formula (6) where $R^5$ is a hydrogen atom; and the acylation through Friedel-Crafts reaction gives an enamine-keto intermediate, a type of enamine-carbonyl intermediate represented by formula (6) where $R^5$ is a group except hydrogen atom.

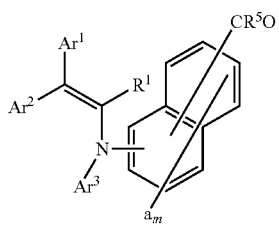

(6)

wherein $R^5$ is $R^4$ when n in formula (1) is 0, but is $R^2$ when n is 1, 2 or 3; and $Ar^1$, $Ar^2$, $Ar^3$, $R^1$, $R^2$, $R^4$ a, m and n are the same as defined in formula (1).

The Vilsmeier reaction is effected, for example, as follows: Phosphorus oxychloride and N,N-dimethylformamide (DMF), or phosphorus oxychloride and N-methyl-N-phenyl-formamide, or phosphorus oxychloride and N,N-diphenyl-formamide are added to a solvent such as N,N-dimethylformamide or 1,2-dichloroethane to prepare a Vilsmeier reagent. 1.0 equivalent of an enamine intermediate represented by formula (5) is added to from 1.0 to 1.3 equivalents of the thus-prepared Vilsmeier reagent, and stirred for 2 to 8 hours under heat at 60 to 110° C. Next, this is hydrolyzed with an aqueous alkaline solution such as 1 to 8 N aqueous sodium hydroxide or potassium hydroxide solution. This gives an enamine-aldehyde intermediate, a type of enamine-carbonyl intermediate represented by formula (6) where $R^5$ is a hydrogen atom, at high yield.

The Friedel-Crafts reaction is effected, for example, as follows: From 1.0 to 1.3 equivalents of a reagent prepared from aluminum chloride and an acid chloride, and 1.0 equivalent of an enamine intermediate represented by formula (5) are added to a solvent such as 1,2-dichloroethane, and stirred for 2 to 8 hours at −40 to 80° C. As the case may be, the reaction system is heated. Next, this is hydrolyzed with an aqueous alkaline solution such as 1 to 8 N aqueous sodium hydroxide or potassium hydroxide solution. This gives an enamine-keto intermediate, a type of enamine-carbonyl intermediate represented by formula (6) where $R^5$ is a group except hydrogen atom, at high yield.

Finally, the enamine-carbonyl intermediate represented by formula (6) is processed with a Wittig reagent of the following general formula (7-1) or (7-2) through Wittig-Horner reaction under basic condition to obtain an enamine compound represented by formula (1). In this step, when a Wittig reagent represented by formula (7-1) is used, it gives an enamine compound represented by formula (1) where n is 0; and when a Wittig reagent represented by formula (7-2) is used, it gives an enamine compound represented by formula (1) where n is 1, 2 or 3.

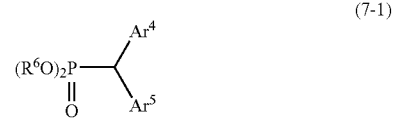

(7-1)

wherein $R^6$ represents an alkyl group which may have a substituent or an aryl group which may have a substituent; and $Ar^4$ and $Ar^5$ have the same meanings as those defined in formula (1).

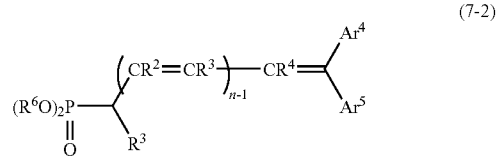

(7-2)

wherein $R^6$ represents an alkyl group which may have a substituent or an aryl group which may have a substituent; n indicates an integer of from 1 to 3; and $Ar^4$, $Ar^5$, $R^2$, $R^3$ and $R^4$ have the same meanings as those defined in formula (1).

The Wittig-Horner reaction is effected, for example, as follows: 1.0 equivalent of an enamine-carbonyl intermediate represented by formula (6), from 1.0 to 1.20 equivalents of a Wittig reagent represented by formula (7-1) or (7-2), and from 1.0 to 1.5 equivalents of a metal alkoxide base such as potassium t-butoxide, sodium ethoxide or sodium methoxide are added to a solvent such as toluene, xylene, diethyl ether, tetrahydrofuran (THF), ethylene glycol dimethyl ether, N,N-dimethylformamide or dimethylsulfoxide, and stirred for 2 to 8 hours at room temperature or under heat at 30 to 60° C. This gives an enamine compound represented by formula (1) at high yield.

As the enamine compound represented by the general formula (1), for example, one or more of materials selected from the group consisting of the exemplified compounds shown in Table 1 to Table 32 is used alone or as a mixture.

The enamine compound represented by the general formula (1) may also be used with other charge transporting substance as a mixture. Other charge transporting substance to be used in admixture with the enamine compound represented by the general formula (1) can include, for example, carbazole derivatives, oxazole derivatives, oxadiazole derivatives, thiazole derivatives, thiadiazole derivatives, triazole derivatives, imidazole derivatives, imidazolone compound, imidazolidine derivatives, bisimidazolidine derivatives, styryl derivatives, hydrazone compound, polycyclic aromatic compound, indole derivatives, pyrazoline derivatives, oxazolone derivatives, benzimidazole derivatives, quinazoline derivatives, benzofuran derivatives, acrydine derivatives, phenadine derivatives, aminostylbene derivatives, triarylamine derivatives, triarylmethane derivatives, phenylene diamine derivatives, stylbene derivatives and benzidine derivatives. In addition, a polymer having a group generated from those compounds in a main chain or a side chain, for example, poly-N-vinyl carbazole, poly-1-vinylpyrene and poly-9-vinylanthracene and the like are included.

However, in order to attain particularly high charge transportability, it is preferred that the total amount of the charge transporting substance 13 is the enamine compound represented by the general formula (1).

As the antioxidant to be contained in the photosensitive layer 14, antioxidants usually utilized being added to resins, etc can be used as they are, and for example, hindered phenol compounds, phosphoric antioxidants, organic sulfuric antioxidants, hydroquinone derivatives, paraphenylene diamine derivatives, or tocopherol compounds are used.

Among the antioxidants described above, hindered phenol compounds, phosphoric antioxidants and organic sulfuric antioxidants are preferably used. When such antioxidants are used, decomposition and deterioration of the enamine compound represented by the general formula (1) contained in the photosensitive layer 14 as the charge transporting substance 13 can be suppressed particularly to further mitigate the fatigue degradation upon repetitive use to further improve the durability of the electrophotographic photoreceptor 1. In addition, stability of the coating liquid upon forming the photosensitive layer 14 by coating can be improved further, thereby enabling to further improve the stability of quality and the productivity of the electrophotographic photoreceptor 1.

In this specification, the hindered phenol compound is a compound having a hindered phenol structural unit, and the hindered phenol structural unit is a structure unit derived from a phenol compound having a bulky atomic group in the vicinity of a phenolic hydroxyl group. The bulky atomic group includes, for example, branched alkyl groups, alicyclic hydrocarbon groups, aryl groups and heterocyclic groups.

The hindered phenol structural unit is preferably represented by the following general formula (I):

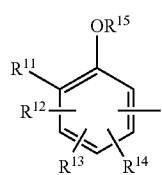

(I)

In the general formula (I), $R^{11}$ represents a branched alkyl group, linear alkyl group of 8 or more carbon atoms, unsaturated aliphatic hydrocarbon group, cycloaliphatic hydrocarbon group, aryl group, heterocyclic group, multi-substituted silyl group, monovalent group including a cyclic group or monovalent group including an alkyl group of 4 or more carbon atoms. $R^{12}$, $R^{13}$ and $R^{14}$ each represents a hydrogen atom, halogen atom or monovalent organic residue, at least two of $R^{12}$, $R^{13}$ and $R^{14}$ may bond with each other to form a ring structure. $R^{15}$ represents a hydrogen atom or monovalent organic residue.

In the general formula (I), as the branched alkyl group represented by $R^{11}$, those of 3 to 18 carbon atoms are preferred, and specific examples thereof can include, for example, t-alkyl groups such as t-butyl, t-pentyl, and t-octyl, and s-alkyl groups such as s-butyl, s-octyl, and s-octadecyl.

As the linear alkyl group of 8 or more carbon atoms represented by $R^{11}$, those of 12 to 18 carbon atoms are preferred.

As the unsaturated aliphatic hydrocarbon group represented by $R^{11}$, those of 2 to 12 carbon atoms are preferred, and specific examples thereof can include, for example, alkenyl groups such as 2-propenyl, 1,3-butadienyl, 2-pentenyl and 1,4-hexadienyl, alkynyl groups such as ethynyl and 2-hexynyl, and aliphatic hydrocarbon groups having carbon-carbon double bond and triple bond such as 2-pentene-4-inyl and 1-heptene-5-inyl.

As the cycloaliphatic hydrocarbon group represented by $R^{11}$, those of 5 to 8 carbon atoms are preferred, and specific examples thereof can include, for example, cycloalkyl groups such as cyclopentyl, cyclohexyl, cycloheptyl and 1-methylcyclohexyl, cycloalkenyl groups such as 2-cyclopenten-1-yl and 1-cyclohexenyl, cycloalkinyl groups such as 2-cyclohexin-1-yl, and cycloaliphatic hydrocarbon group having carbon-carbon double bond and triple bond such as 2-cyclodecen-5-in-1-yl.

Specific examples of the aryl group represented by $R^{11}$ can include, for example, phenyl, naphthyl, anthryl and biphenylyl.

Specific examples of the heterocyclic group represented by $R^{11}$ can include, for example, thienyl, furyl, benzofuryl, benzothiophenyl and benzothiazolyl.

Specific examples of the multiply-substituted silyl group represented by $R^{11}$ can include, for example, tri-substituted silyl group such as trimethylsilyl and triisopropylsilyl, and di-substituted silyl group such as dimethylsilyl and diphenylsilyl.

The monovalent group containing a cyclic group represented by $R^{11}$ preferably contains, as the cyclic group, the cycloaliphatic hydrocarbon group, aryl group or cycloaliphatic group described above. Specific examples of the monovalent group containing the cyclic group represented by $R^{11}$ can include, for example, aralkyl groups such as benzyl, phenetyl, 1-naphthylmethyl, and 1-methylbenzyl, phosphino group substituted with an aryl group, such as phenylphosphino, diphenylphosphino, and ethylphenyl phosphino, cycloalkyl alkyl groups such as cyclohexylmethyl and 1-cyclohexyl-1-methylethyl, aryloxy groups such as phenoxy, arylthio groups such as thiophenoxy and alkyl groups substituted with a heterocyclic group such as furfuryl, pipelidio methyl, and thienylmethyl.

The monovalent group containing an alkyl group of 4 or more carbon atoms represented by $R^{11}$, preferably contains alkyl groups of 4 to 18 carbon atoms as the alkyl group of 4 or more carbon atoms. Specific examples of the monovalent group containing an alkyl group of 4 or more carbon atoms represented by $R^{11}$ can include, for example, alkyl carbonyl amino groups such as heptylcarbonyl amino and N-methyloxyl carbonyl amino, alkylthioalkyl groups such as octylthiomethyl, decylthioethyl, and pentyl thioethyl, and alkoxy alkyl groups such as heptyloxymethyl, 2-dodecylaoxyethy, and hexyloxyethyl.

In the general formula (I), the halogen atom represented by $R^{12}$, $R^{13}$ or $R^{14}$ can include, for example, a fluorine atom or chlorine atom.

The monovalent organic residue represented by $R^{12}$, $R^{13}$ or $R^{14}$ can include, for example, alkyl groups such as methyl, ethyl, t-butyl, t-pentyl, hexyl, and octyl, aryl groups such as phenyl, naphtyl, anthryl, and biphenylyl, aralkyl groups such as benzyl, phenetyl, 1-naphthylmethyl, and 1-methylbenzyl, heterocyclic ring groups such as pyridyl, thienyl, furyl, benzofuryl, benzothiophenyl, benzothiazolyl, and N-indolyl, and amino groups such as diethyl amino, dimethyl amino, and diisopropyl amino. Further, hydroxyl group, alkoxy group, carboxylic acid group, acyl group, ester group, amido group, siloxane group, and silyl group, etc. can also be included. The alkyl group represented by $R^{12}$, $R^{13}$ or $R^{14}$ preferably has from 1 to 40 carbon atoms.

The monovalent organic residue represented by $R^{12}$, $R^{13}$ or $R^{14}$ may have a substituent, and the substituent can include, for example, an ester group, carboxylic acid group, phospholic acid group, and thioether group.

In the general formula (I), the monovalent organic residue represented by $R^{15}$ can include, for example, alkyl groups such as methyl, ethyl, propyl, hexyl and octyl, aryl groups such as phenyl, naphthyl, and anthlyl, aralkyl groups such as benzyl, phenetyl, and 1-naphthylmethyl, heterocyclic groups such as piridyl, thienyl, furyl, benzofuryl, and benzothiophenyl, and acyl groups such as acryloyl and acetyl. The alkyl group represented by $R^{15}$ preferably has 1 to 40 carbon atoms, more preferably, from 1 to 18 carbon atoms.

The hindered phenol compound may have two or more hindered phenol structural units represented by the general formula (I) described above. In this case, the plurality of hindered phenol structural units may be identical or different.

In a case where the hindered phenol compound contains a plurality of hindered phenol structural units in this manner, the plurality of hindered phenol structural units may be bonded directly or may be bonded by way of an atom or atomic group.

Specific examples of the atom for bonding the plurality of hindered phenol structural units can include, for example, an oxygen atom, sulfur atom and carbon atom.

The atomic group for bonding the plurality of hindered phenol structural units can include, for example, polyvalent groups such as bivalent and trivalent groups derived from saturated aliphatic hydrocarbons, unsaturated aliphatic hydrocarbons, aromatic hydrocarbons or heterocyclic compounds. Specific examples of the polyvalent group derived from the saturated aliphatic hydrocarbons can include bivalent groups, for example, alkylene groups such as methylene, ethylene, and propylene, and alkylidene groups such as ethylidene, propylidene and butylidene, and trivalent groups, for example, alkanylidene groups such as 1-propanyl-3-ilydene and alkanetriyl groups such as 1,3,6-hexane triyl. Specific examples of the polyvalent group derived from unsaturated aliphatic hydrocarbon can include bivalent groups, for example, alkenylene groups such as vinylene and propenylene, alkadienylene groups such as 1,3-butadienylene, and 1,4-hexadiethylene and alkinylene groups such as 3-pentynylene and 2-hexynylene, and trivalent groups, for example, alkenylidene groups such as 2-pentenyl-5-ylidene. Specific examples of the polyvalent groups derived from aromatic hydrocarbon can include, trivalent groups, for example, arylene groups such as phenylene, naphthylene, biphenylene and 2,7-phenanetholylene and 1,3,5-benzenetriyl, and tetravalent groups such as 1,4,5,8-anthracenetetrayl. Specific examples of the polyvalent groups derived from the heterocyclic compound can include, for example, bivalent groups such as 3,5-pyridinediyl and 2,6-quinolinediyl, trivalent groups such as 1,3,5-triadine-2,4,6-triyl and 1,3,5-triadine-2,4,6-trion-1,3,5-triyl, and tetravalent groups such as 1,4,5,8-acridine tetrayl.

While specific examples of the hindered phenol compound can, for example, include Exemplified Compounds HP-1 to HP-80 shown in Tables 33 to 39, the hindered phenol compounds are not limited to them. In the following description, t-Bu represents t-butyl group ($-C(CH_3)_3$, $t$-$C_5H_{11}$ represents t-pentyl group ($-C(CH_3)_2C_2H_5$) and $t$-$C_8H_{17}$ represents t-octyl group ($-C(CH_3)_2C_5H_{11}$).

TABLE 33

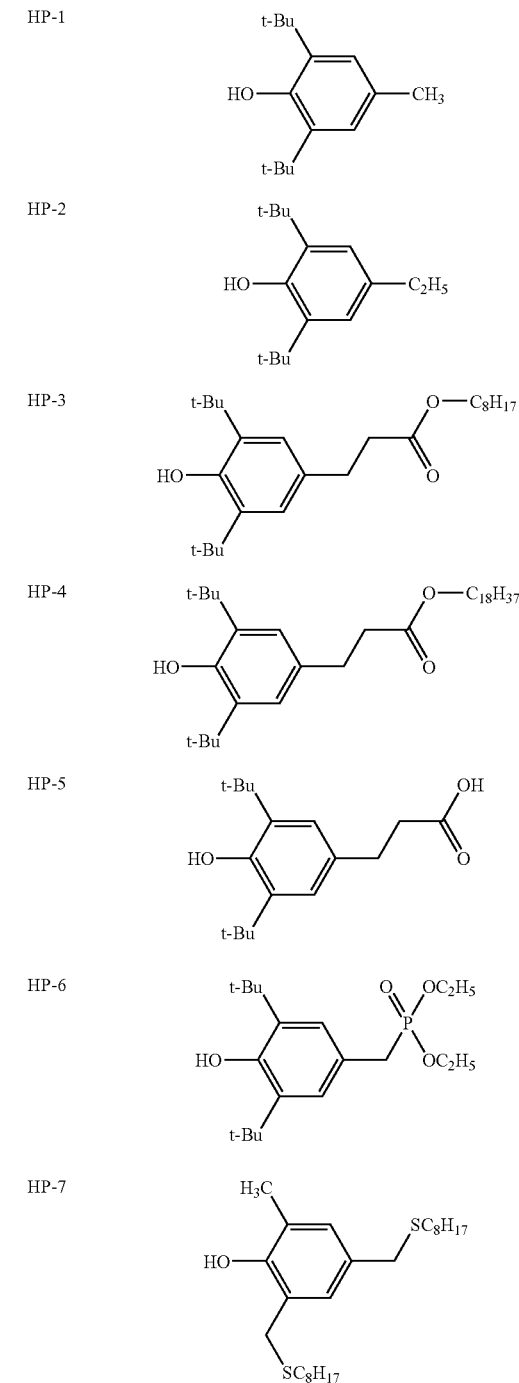

TABLE 33-continued
HP-8 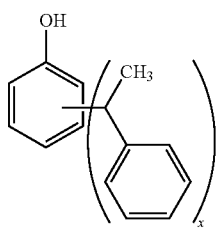
(x represents an integer of 1 to 5)
HP-9 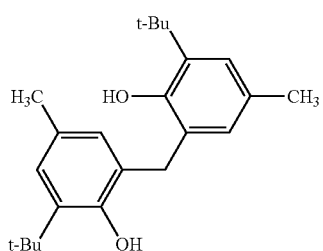
HP-10 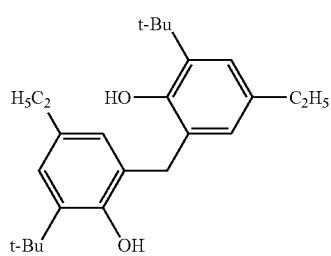
HP-11 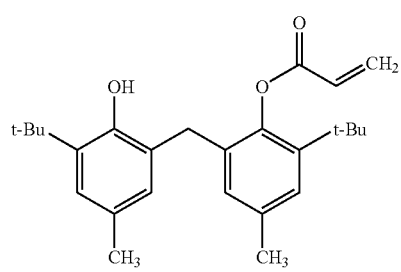
HP-12 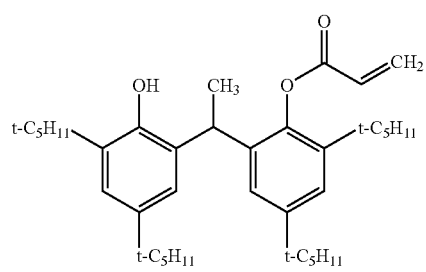
HP-13 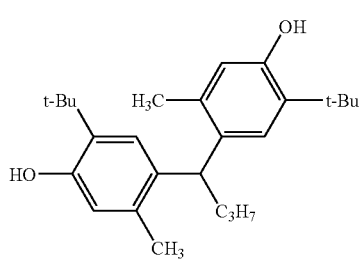
TABLE 33-continued
HP-14 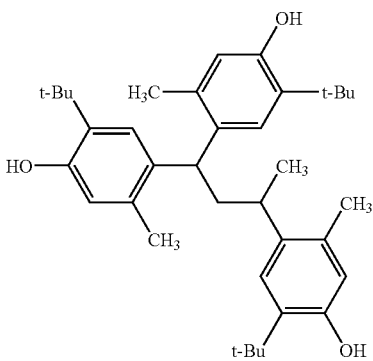
TABLE 34
HP-15 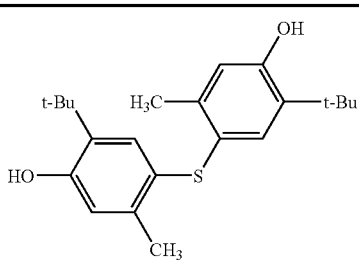
HP-16 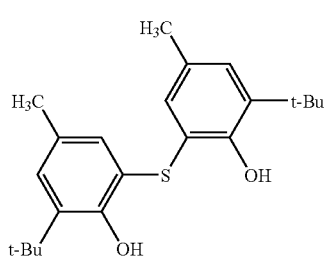
HP-17 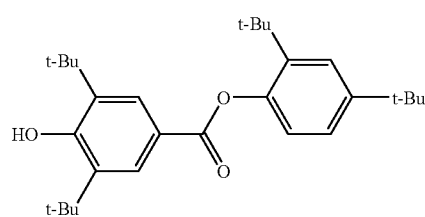
HP-18 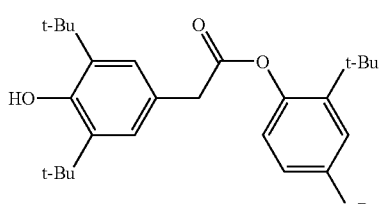
HP-19 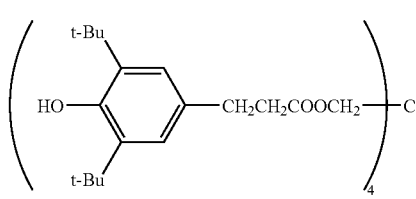

TABLE 34-continued
HP-20 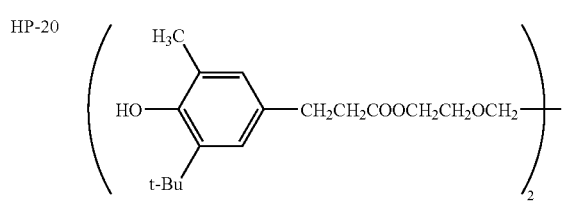
HP-21 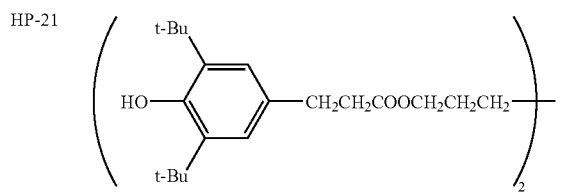
TABLE 35
HP-22 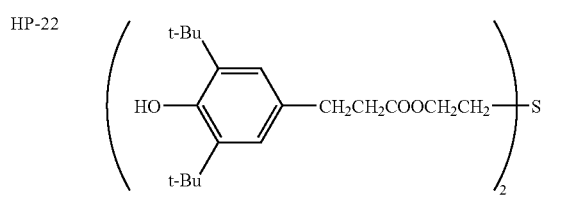
HP-23 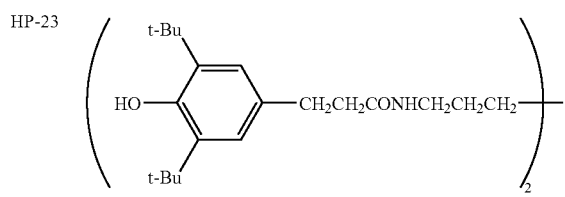
HP-24 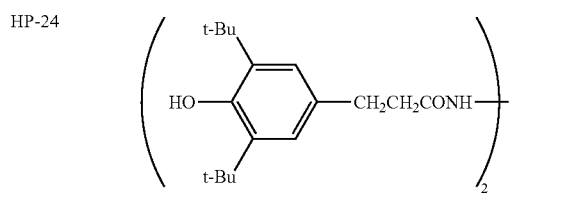
HP-25 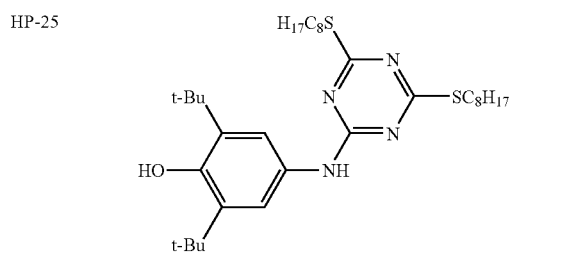
TABLE 35-continued
HP-26 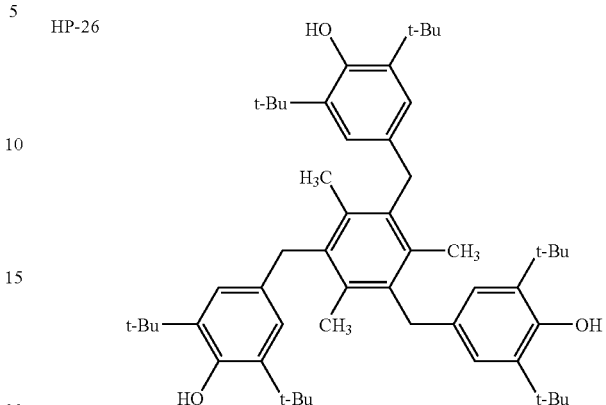
HP-27 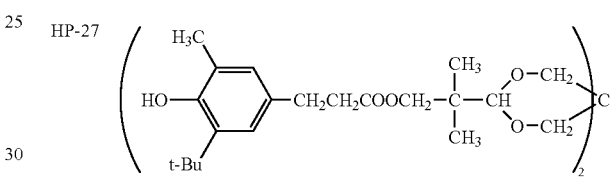
TABLE 36
HP-28 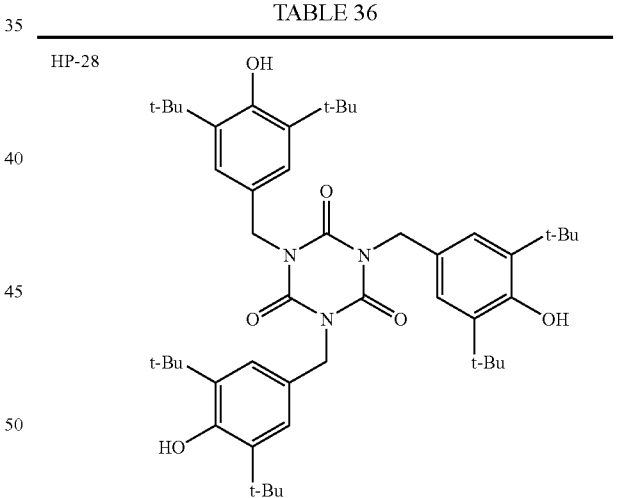
HP-29 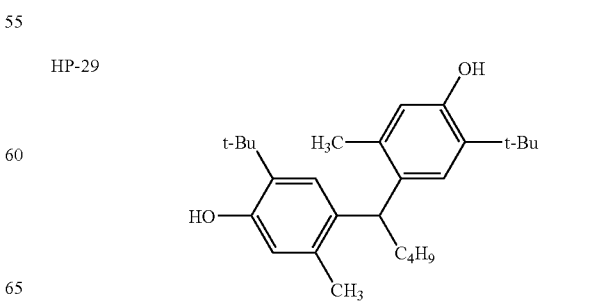

TABLE 36-continued
HP-30 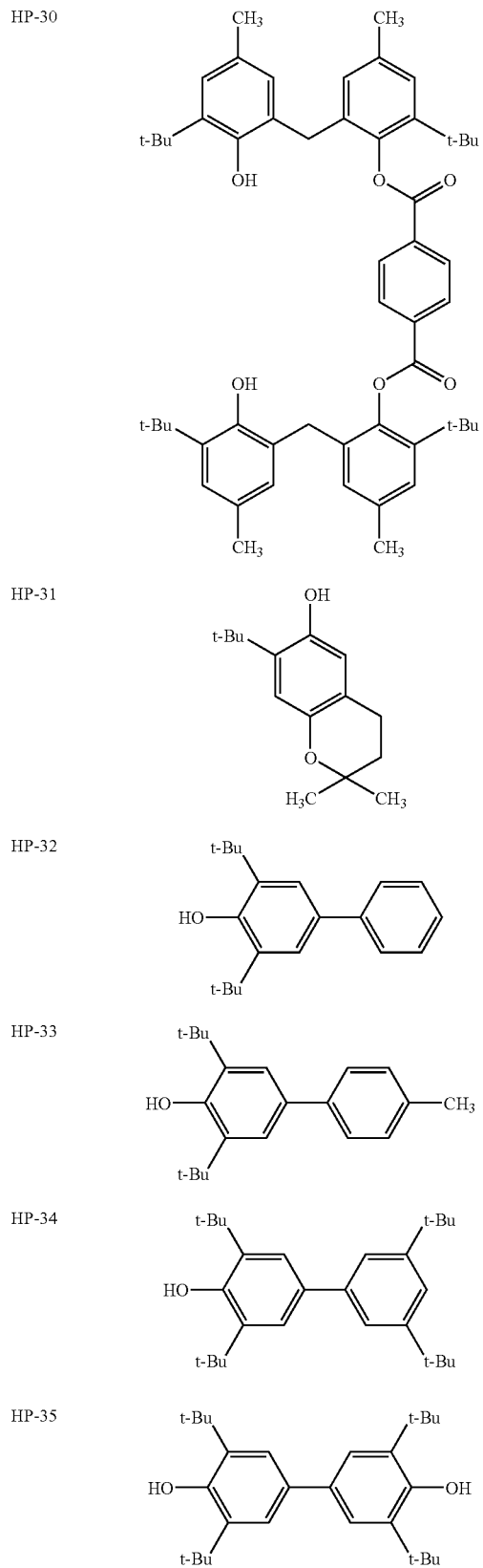
HP-31
HP-32
HP-33
HP-34
HP-35
TABLE 36-continued
HP-36 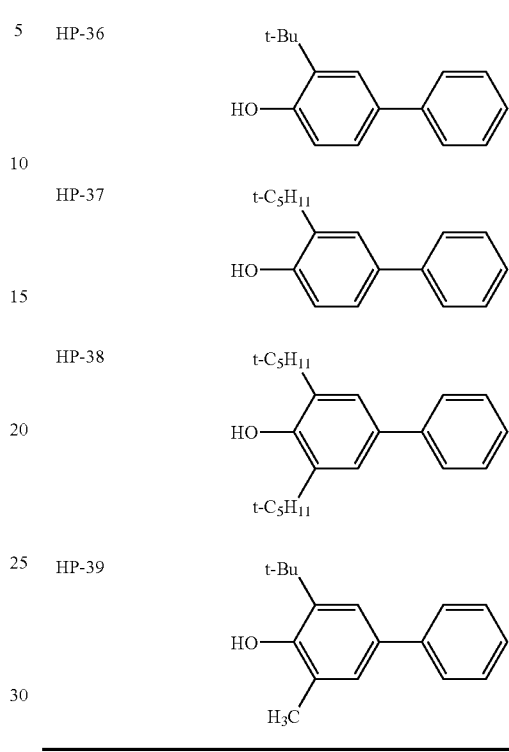
HP-37
HP-38
HP-39
TABLE 37
HP-40 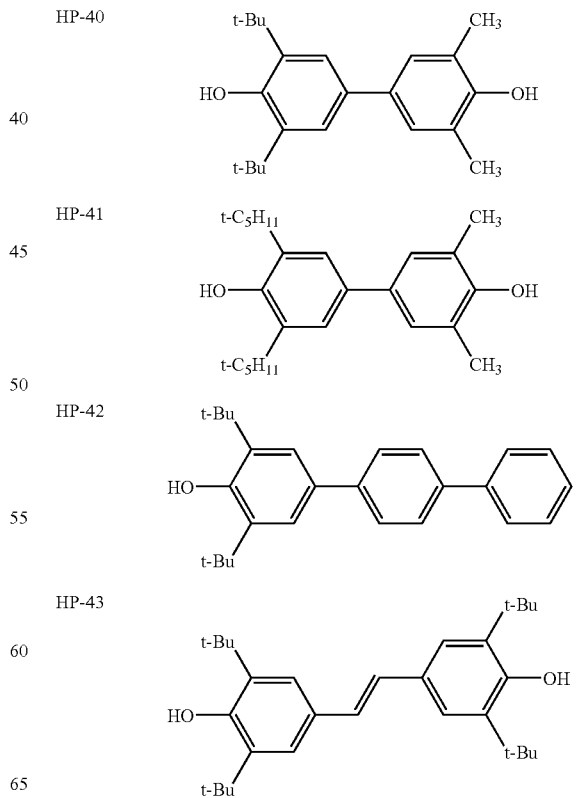
HP-41
HP-42
HP-43

TABLE 37-continued
HP-44 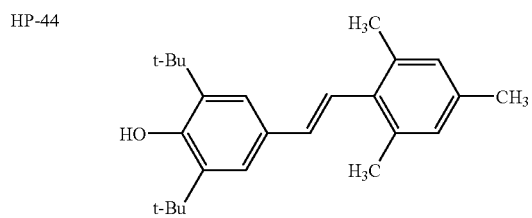
HP-45 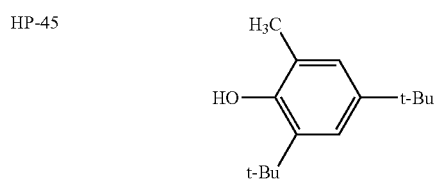
HP-46 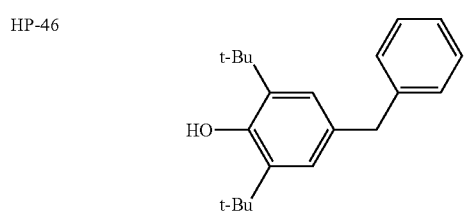
HP-47 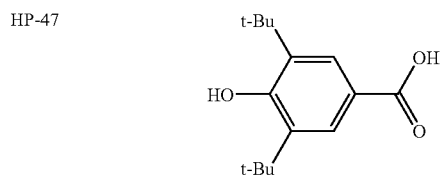
HP-48 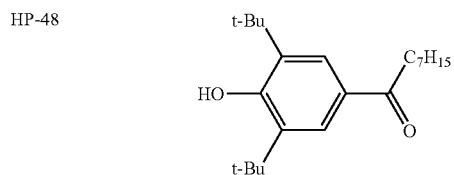
HP-49 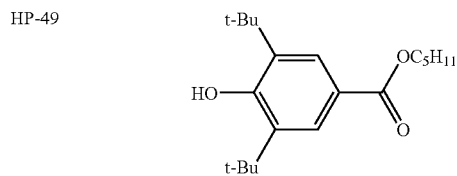
HP-50 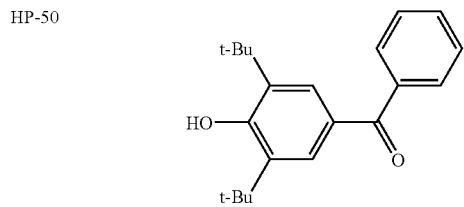
TABLE 37-continued
HP-51 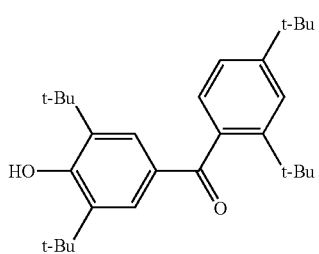
HP-52 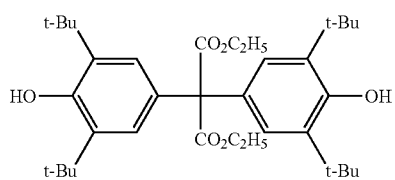
HP-53 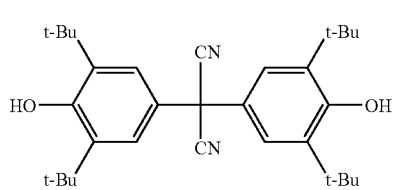
TABLE 38
HP-54 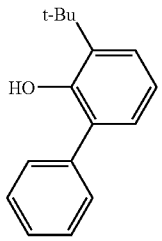
HP-55 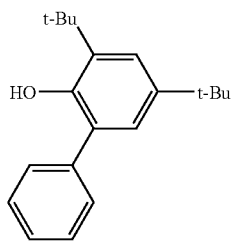
HP-56 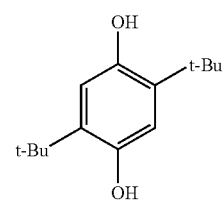

TABLE 38-continued
HP-57 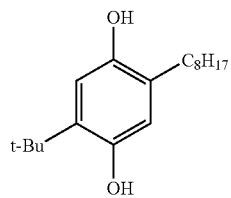
HP-58 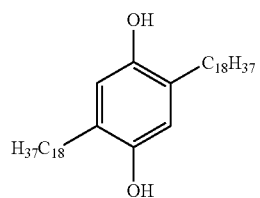
HP-59 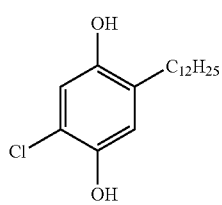
HP-60 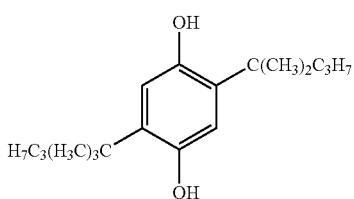
HP-61 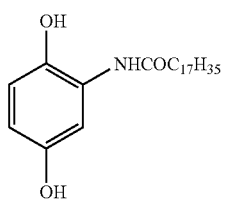
HP-62 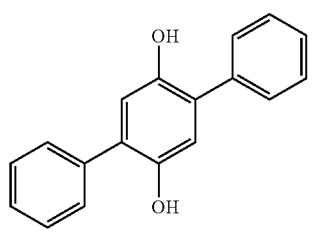
HP-63 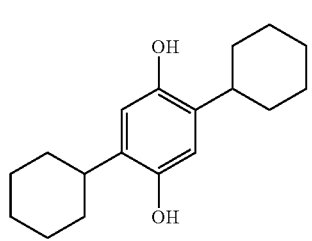
TABLE 38-continued
HP-64 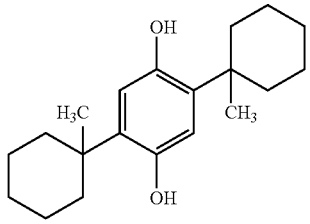
HP-65 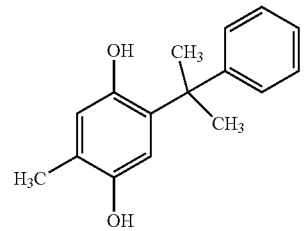
HP-66 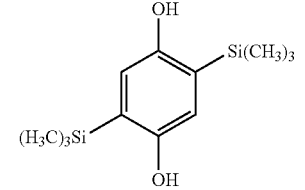
HP-67 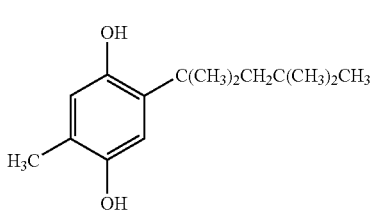
TABLE 39
HP-68 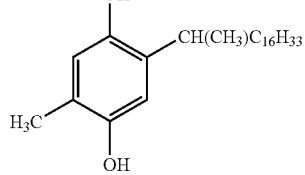
HP-69 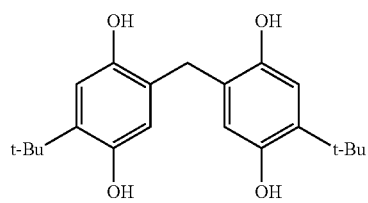
HP-70 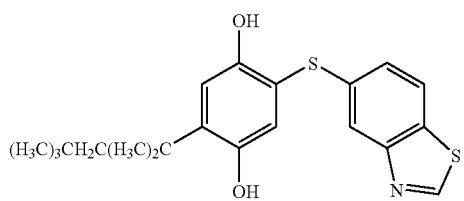

TABLE 39-continued

HP-71
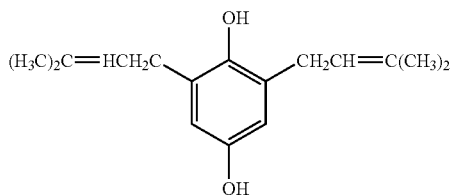

HP-72
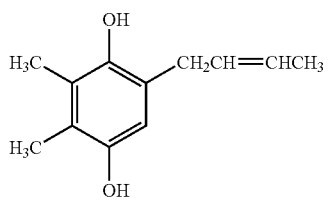

HP-73
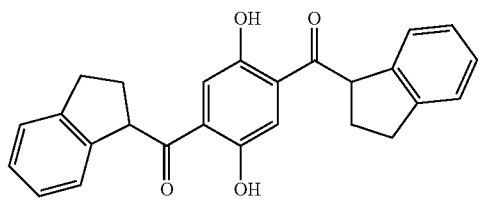

HP-74
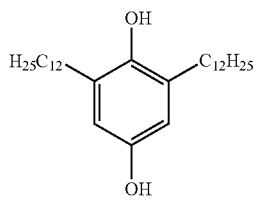

HP-75
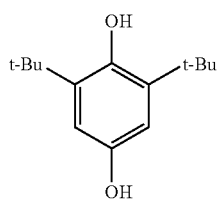

HP-76
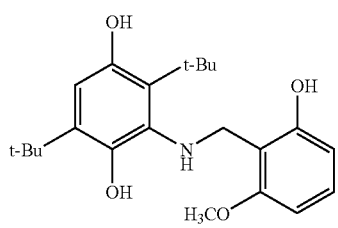

HP-77
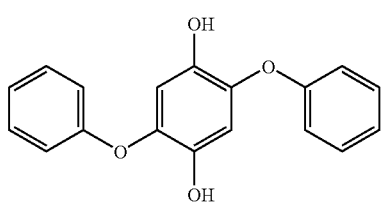

TABLE 39-continued

HP-78
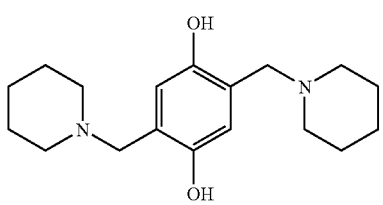

HP-79
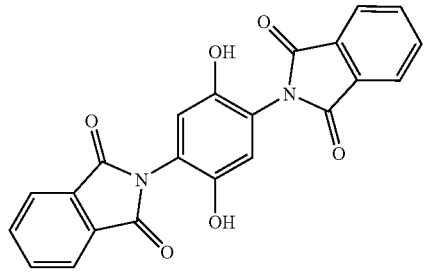

HP-80
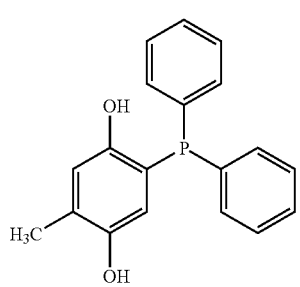

Among the hindered phenol compounds shown in Table 33 to Table 39, Exemplified Compound HP-1 shown in Table 33, namely, the hindered phenol compound represented by the following structural formula (I-a) is preferably used.

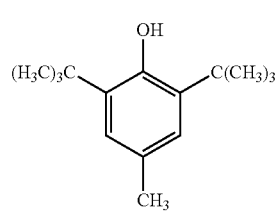

(I-a)

As a phosphoric antioxidant, while known compounds can be used, and specific examples thereof can include, for example, Exemplified Compounds P-1 to P-47 shown in Tables 40 to 44, the phosphoric antioxidants are not limited to them.

TABLE 40

| | |
|---|---|
| P-1 | $P(OCH_3)_3$ |
| P-2 | $P(OC_2H_5)_3$ |
| P-3 | $P(OC_4H_9)_3$ |
| P-4 | $P(OC_{10}H_{21})_3$ |
| P-5 | $P(OC_{12}H_{25})_3$ |
| P-6 | $P(OC_{13}H_{27})_3$ |
| P-7 | $P(OC_{18}H_{37})_3$ |
| P-8 | $(H_{25}C_{12}O)_2P(O)H$ |
| P-9 | $(H_{37}C_{18}O)_2P(O)H$ |
| P-10 | $P(SC_{10}H_{21})_3$ |
| P-11 | $P(SC_{12}H_{25})_3$ |

TABLE 40-continued
P-12    P(SC₁₈H₃₇)₃
P-13    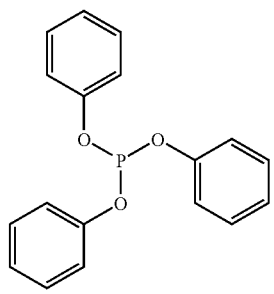
P-14    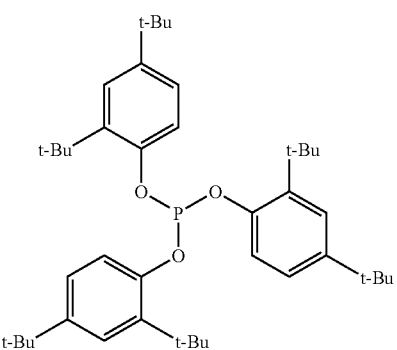
P-15    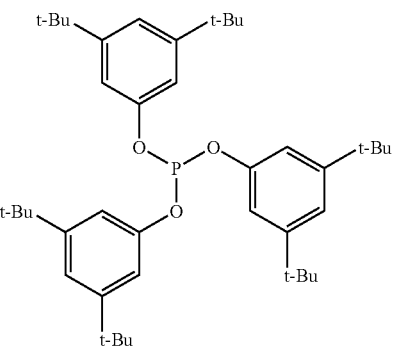
P-16    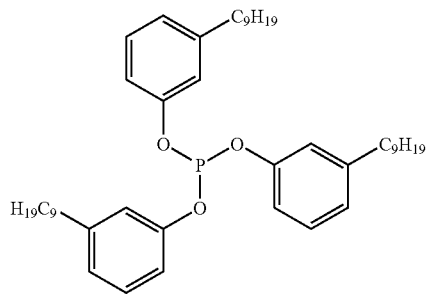
TABLE 40-continued
P-17    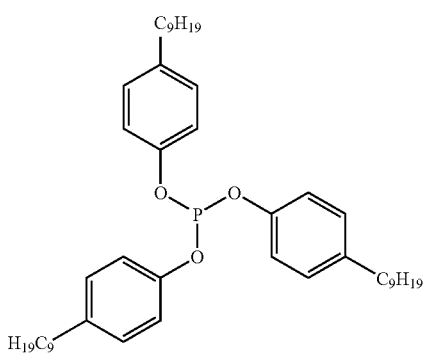
P-18    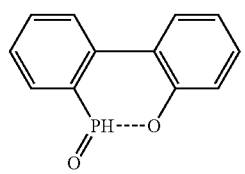
TABLE 41
P-19    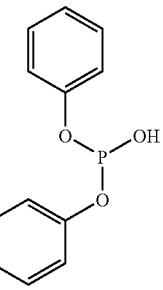
P-20    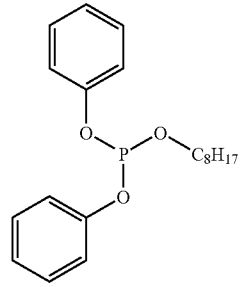
P-21    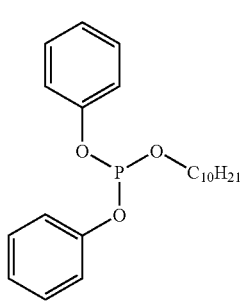

TABLE 41-continued
P-22 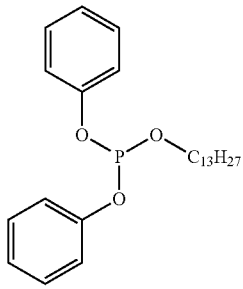
P-23 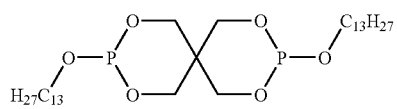
P-24 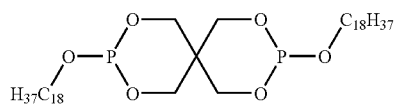
P-25 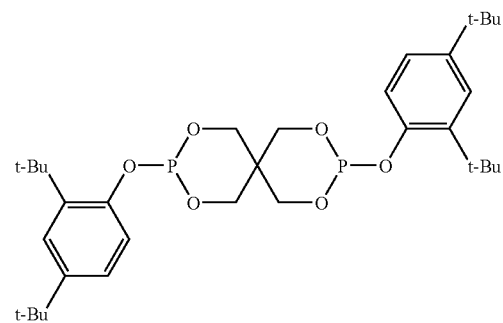
P-26 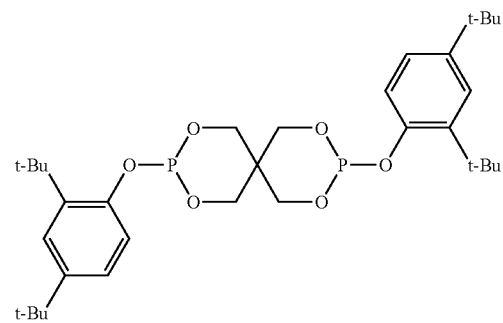
P-27 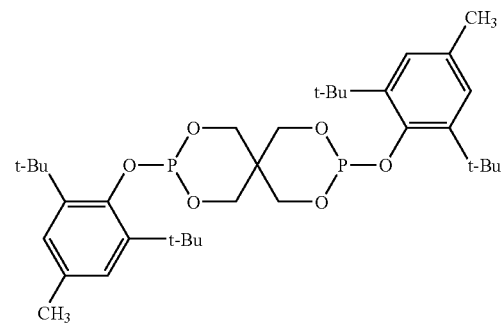
TABLE 41-continued
P-28 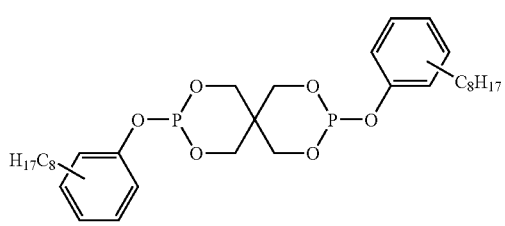
P-29 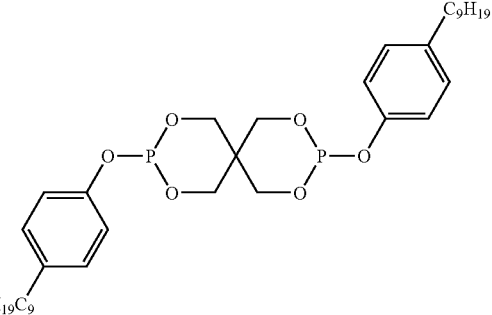
P-30 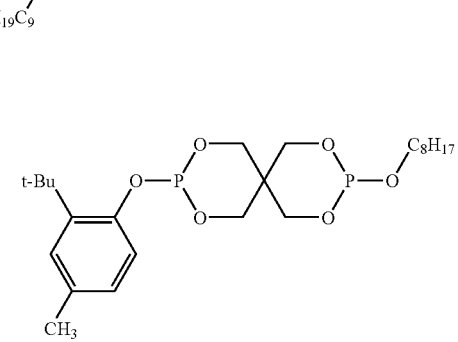
TABLE 42
P-31 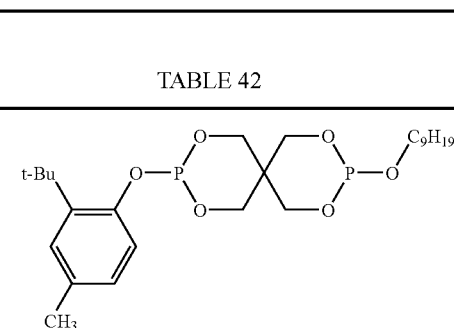
P-32 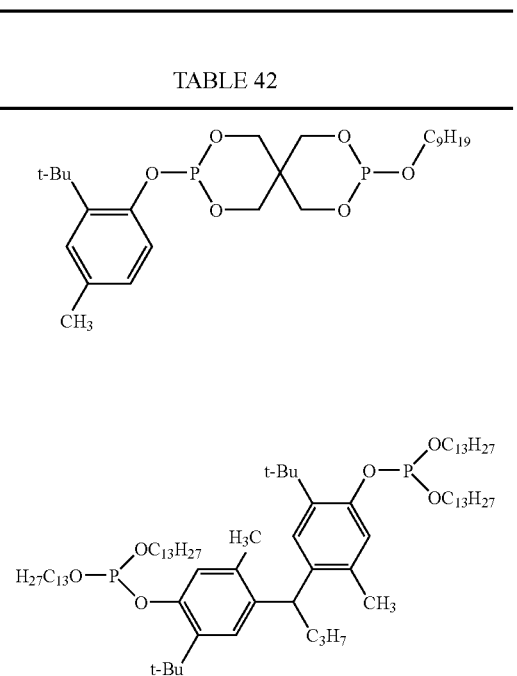

TABLE 42-continued
P-33 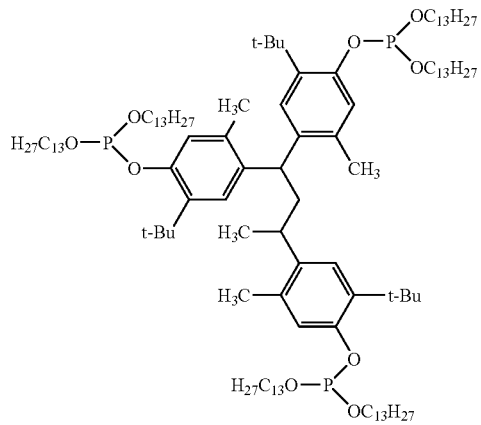
P-34 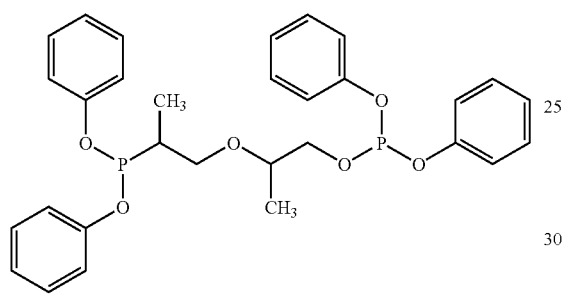
P-35 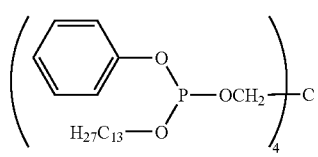
P-36 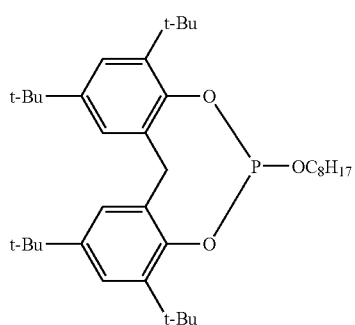
TABLE 43
P-37 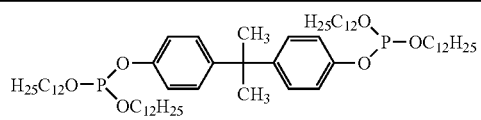
P-38 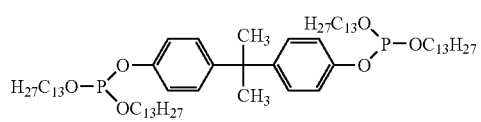
TABLE 43-continued
P-39 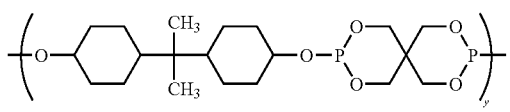
(weight-average molecular weight: about 2000 to 20000)
P-40 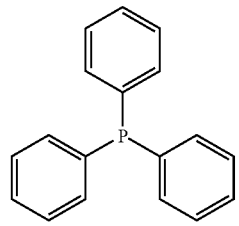
P-41 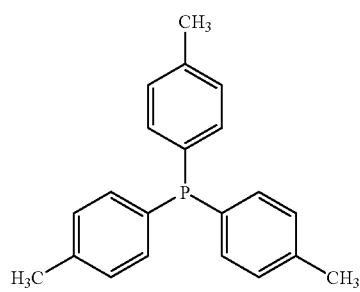
P-42 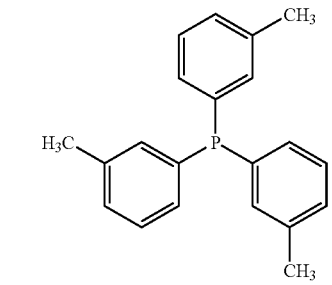
TABLE 44
P-43 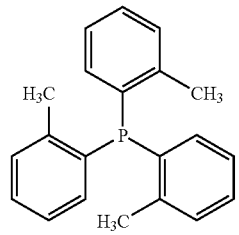
P-44 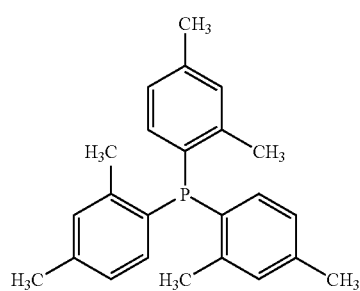

TABLE 44-continued

P-45
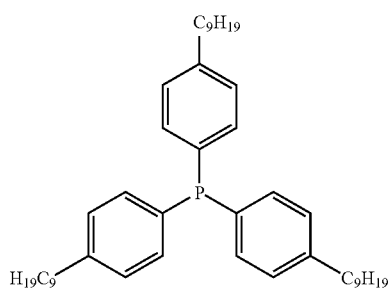

P-46
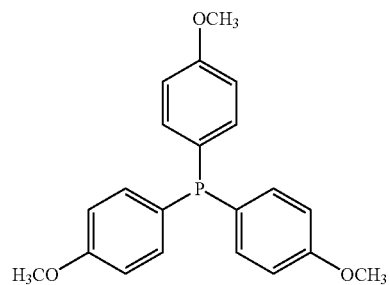

P-47
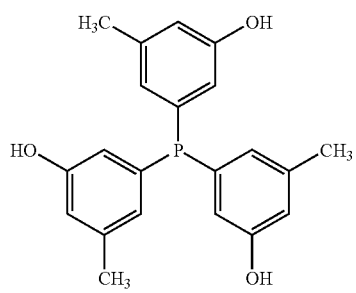

Exemplified Compound P-39 shown in Table 43 is commercially available, for example, as JPH-3800 (trade name of product, manufactured by Johoku Chemical Co., Ltd.).

As the organic sulfuric antioxidant, while known compounds can be used, and specific examples thereof can include, for example, Exemplified Compounds S-1 to S-14 shown in Tables 45 and 46 described below, the organic sulfuric antioxidants are not limited to them.

TABLE 45

| S-1 | $S(C_8H_{17})_2$ |
| S-2 | $S(C_{12}H_{25})_2$ |
| S-3 | $S(C_{16}H_{32})_2$ |
| S-4 | 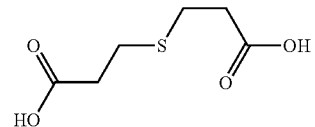 |
| S-5 | 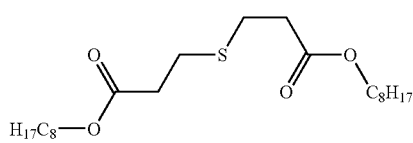 |

TABLE 45-continued

| S-6 | 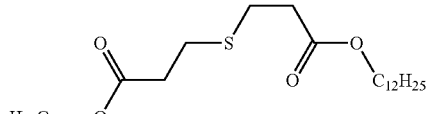 |
| S-7 | 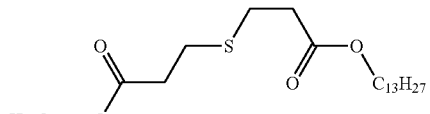 |
| S-8 | 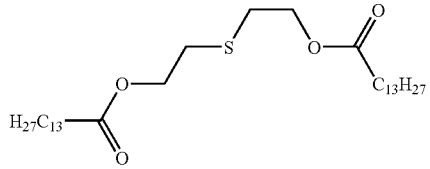 |

TABLE 46

| S-9 | 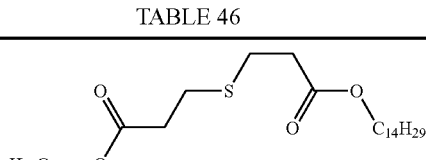 |
| S-10 | 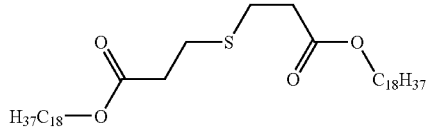 |
| S-11 | $C\!-\!(CH_2OCOCH_2CH_2SC_{12}H_{25})_4$ |
| S-12 | 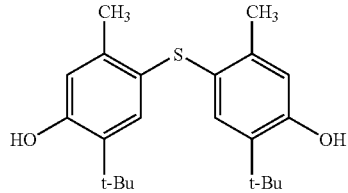 |
| S-13 | 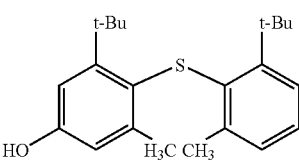 |
| S-14 | 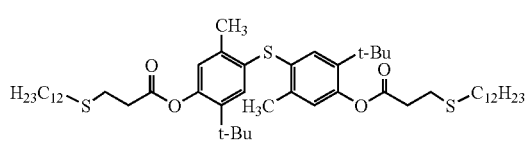 |

Further, as the light stabilizer, light stabilizers usually utilized by being added to resins can be generally used as they are. For example, hindered amine compounds, benzotriazole derivatives and benzophenone derivatives are used.

Among the light stabilizers described above, hindered amine compounds, benzotriazole derivatives, or benzophenone derivatives are preferably used. When such light stabilizers are used, decomposition and deterioration of the enamine compound represented by the general formula (I) contained in the photosensitive layer 14 as the charge transporting substance 13 are suppressed particularly to further mitigate fatigue degradation upon repetitive use, and durability of the electrophotographic photoreceptor 1 can be further improved. In addition, the stability of the coating liquid upon forming the photosensitive layer 14 by coating is further improved, thereby enabling to further improve the stability of quality and the productivity of the electrophotographic photoreceptor 1.

In this specification, "hindered amine compound" is a compound having a hindered amine structural unit, and the hindered amine structural unit is a structural unit derived from an amine compound having a bulky atomic group in the vicinity of an amino nitrogen atom. The bulky atomic group can include, for example, a branched alkyl group, cycloaliphatic hydrocarbon group, aryl group, and heterocyclic group. The hindered amine structural unit may be either an aromatic amine type or aliphatic amine type, the aliphatic amine type being preferred.

The hindered amine structural unit is preferably represented by the following general formula (II):

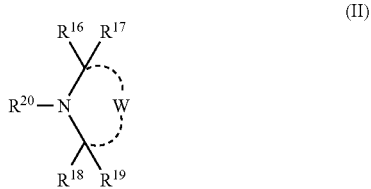

(II)

In the general formula (II), $R^{16}$, $R^{17}$, $R^{18}$ and $R^{19}$ each represents a hydrogen atom, alkyl group, aryl group, heterocyclic group or aralkyl group. $R^{20}$ represents a hydrogen atom or a monovalent organic residue. W represents an atomic group necessary for forming a ring structure containing an amino nitrogen atom. However, all of $R^{16}$, $R^{17}$, $R^{18}$ and $R^{19}$ do not simultaneously represent a hydrogen atom.

In the general formula (II), as the alkyl group represented by $R^{16}$, $R^{17}$, $R^{18}$ and $R^{19}$, those of 1 to 18 carbon atoms are preferred. The alkyl group represented by $R^{16}$, $R^{17}$, $R^{16}$ and $R^{19}$ may have a substituent, and the substituent can include, for example, an aryl group, alkoxyl group, carboxylic acid group, amide group, halogen group and thioether group.

Specific examples of the aryl group represented by $R^{16}$, $R^{17}$, $R^{18}$ and $R^{19}$ include, for example, phenyl, naphthyl, anthlyl and p-tolyl.

Specific examples of the heterocyclic group represented by $R^{16}$, $R^{17}$, $R^{18}$ and $R^{19}$ can include, for example, thienyl, furyl, benzofuryl, and benzothiophenyl.

Specific examples of the aralkyl group represented by $R^{16}$, $R^{17}$, $R^{18}$ and $R^{19}$ can include, for example, benzyl, phenetyl, 1-naphthylmethyl, and 1-methylbenzyl.

The monovalent organic residue represented by $R^{20}$ can includes, for example, alkyl groups such as methyl, ethyl, t-pentyl, hexyl, and octyl, acyl groups such as acetyl, propionyl and butyryl, aryl groups such as phenyl and naphthyl, aralkyl groups such as benzyl, phenetyl and 1-naphtylmethyl, and heterocyclic groups such as pyridyl, thienyl, furyl, benzofuryl, and benzothiophenyl. The alkyl group represented by $R^{20}$ preferably has 1 to 18 carbon atoms.

In the general formula (II), the ring structure containing the amino nitrogen atom formed by W is preferably a five- or six-membered ring, and specific examples thereof can include, for example, each of the rings of piperidine, piperazine, morpholine, pyrrolidine, imidazolidine, oxazolidine, thiazolidine, selenazolidine, pyroline, imidazoline, isoindoline, tetrahydroisoquinoline, tetrahydropyridine, dihydropyridine, dihydroisoquinoline, oxazoline, thiazoline, selenazoline, pyrrol, etc. Among them, while each of the rings of piperidine, piperazine and pyrolidine is particularly preferred. W has one bonding chain in the general formula (II), it is not limitative, but may also have two or more bonding chains.

The ring containing an amino nitrogen atom formed by W may have a substituent, and the substituent can includes, for example, alkyl groups such as methyl, ethyl, and octyl, aryl groups such as phenyl and naphthyl, aralkyl groups such as benzyl and phenetyl, heterocyclic groups such as pyridyl, thienyl, furyl, benzofuryl, and benzothiophenyl, and amino groups such as methylamino, dimethylamino, and diphenylamino. In addition, ester groups, hydroxyl groups and silyl groups may also be included.

The hindered amine compound may have two or more hindered amine structural units represented by the general formula (II) described above. In this case, the plurality of hindered amine structural units may be identical or different with each other.

In a case where the hindered amine compound contains a plurality of hindered amine structural units as described above, the plurality of the hindered amine structural units may be bonded directly or may be bonded by way of an atomic group.

Specific examples of the atom for bonding the plurality of hindered amine structural units can include an oxygen atom, sulfur atom and carbon atom.

Specific examples of the atomic group for bonding the plurality of hindered amine structural units can include polyvalent groups, for example, bivalent and trivalent polyvalent groups derived from saturated aliphatic hydrocarbon, unsaturated aliphatic hydrocarbon, aromatic hydrocarbon or heterocyclic compound. Specific examples of the polyvalent group derived from the saturated aliphatic hydrocarbon can include bivalent groups, for example, alkylene groups such as methylene, ethylene, and propylene, and alkylidene groups such as ethylidene, propylidene and butylidene, and trivalent groups, for example, alkanylidene groups such as 1-propanyl-3-ilydene and alkanetriyl groups such as 1,3,6-hexane triyl. Specific examples of the polyvalent group derived from unsaturated aliphatic hydrocarbons include bivalent groups, for example, alkenylene groups such as vinylene and propenylene, alkadienylene groups such as 1,3-butadienylene and 1,4-hexadiethylene and alkinylene groups such as 3-pentynilene and 2-hexynylene, and trivalent groups, for example, alkenylidene groups such as 2-pentenyl-5-ylidene. Specific examples of the polyvalent groups derived from aromatic hydrocarbon include trivalent groups, for example, arylene groups such as phenylene, naphthylene, biphenylene and 2,7-phenanetholylene and 1,3,5-benzene triyl, and tetravalent groups such as 1,4,5,8-anthracenetetrayl. Specific examples of the polyvalent groups derived from heterocyclic compounds can include, for example, bivalent groups such as 3,5-pyridinediyl and 2,6-quinoline-diyl, trivalent groups such as 1,3,5-triadine-2,4,6-triyl, and tetravalent groups such as 1,4,5,8-acridine-tetrayl.

The hindered amine compound may have the hindered phenol structural units described above in addition to the hindered amine structural units.

While specific examples of the hindered amine compound can include, for example, Exemplified Compounds HA-1 to HA-15 shown in Tables 47 to 49 described above, the hindered amine compounds are not limited to them.
TABLE 47
HA-1 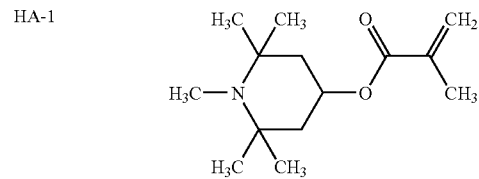
HA-2 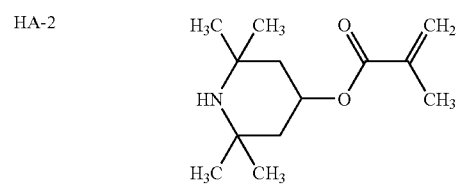
HA-3 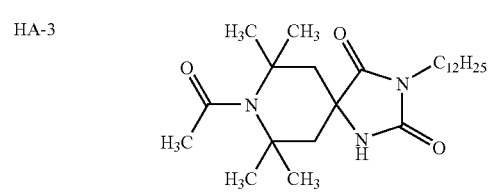
HA-4 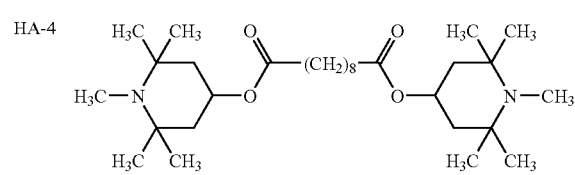
HA-5 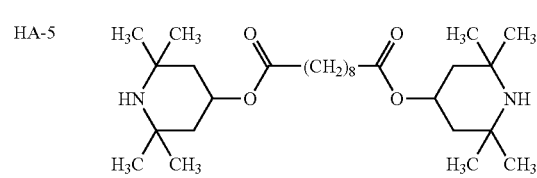
HA-6 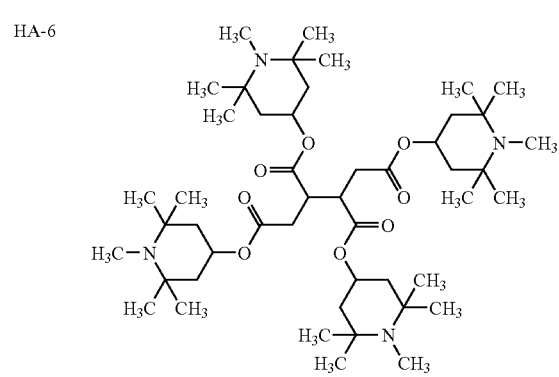
TABLE 48
HA-7 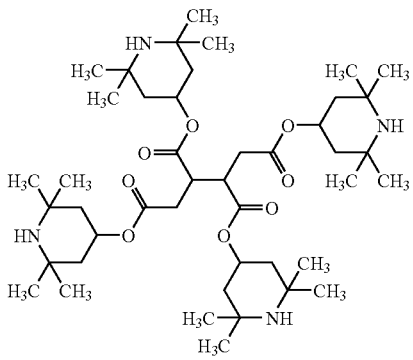
HA-8 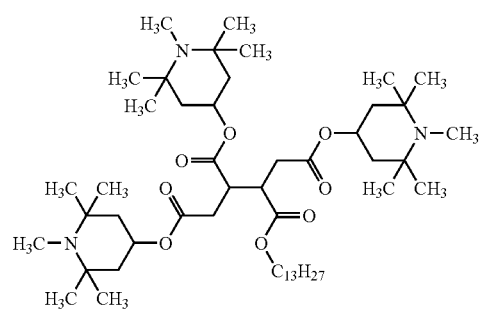
HA-9 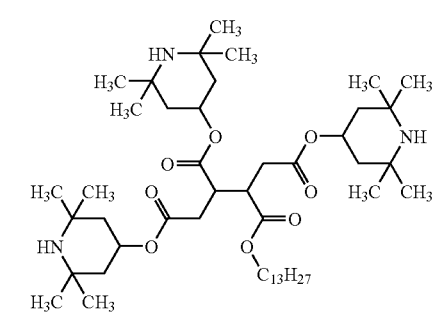
HA-10 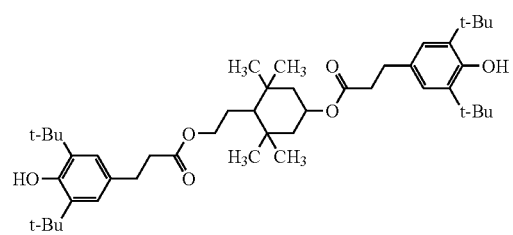

TABLE 49

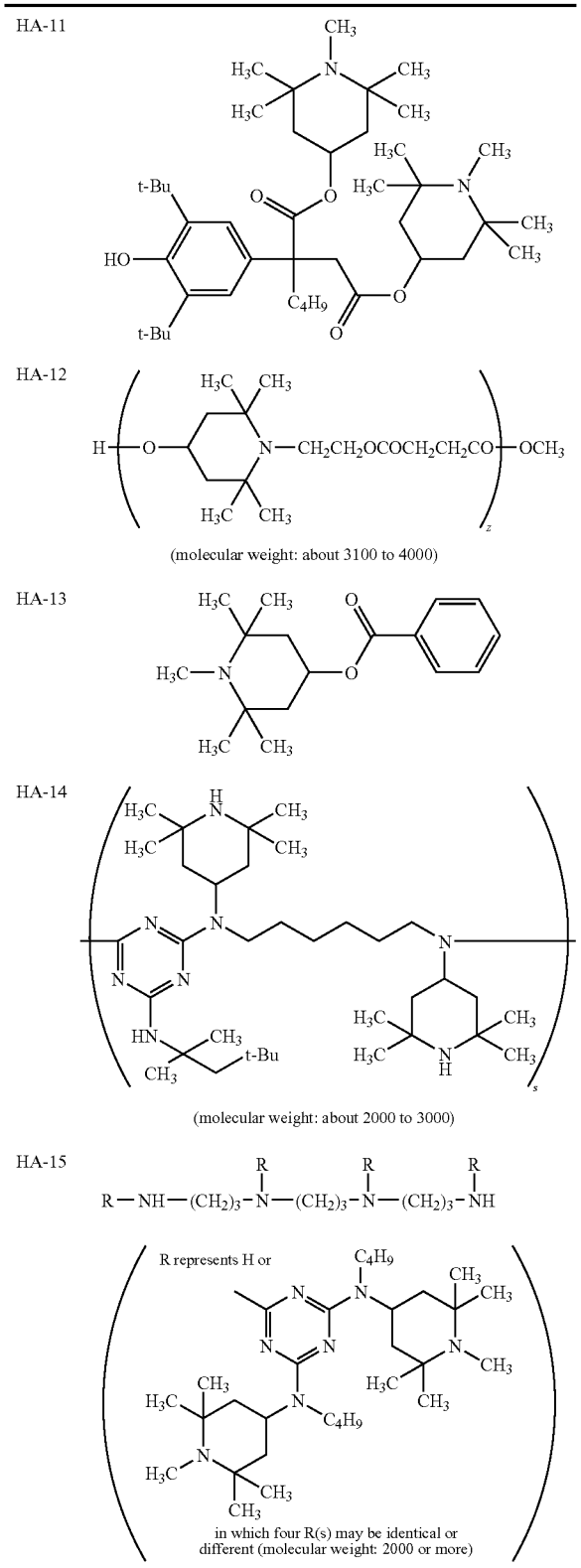

Exemplified Compound HA-12 shown in Table 49 is commercially available as TINUVIN 622 (trade name of product, manufactured by Ciba Geigy Co., Ltd.). Exemplified Compound HA-14 is commercially available, for example, as CHIMASSORB 944 (trade name of product, manufactured by Nippon Ciba Geigy Co., Ltd.). Exemplified Compounds HA-15 is commercially available, for example, as CHIMASSORB 119 (trade name of products, manufactured by Nippon Ciba Geigy Co., Ltd.).

Among the hindered amine compounds shown in Tables 47 to 49, Exemplified Compound HA-3 shown in Table 47, namely, a hindered amine compound represented by the following structural formula (II-a) is preferably used.

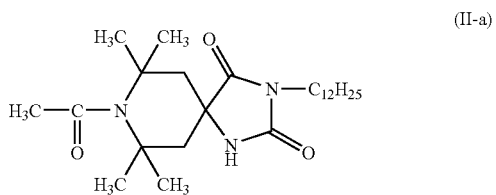

(II-a)

While specific examples of the benzotriazole derivative can include, for example, Exemplified Compounds TZ-1 to TZ-28 shown in the following Tables 50 to 52, the benzotriazole derivatives are not limited to them.

TABLE 50

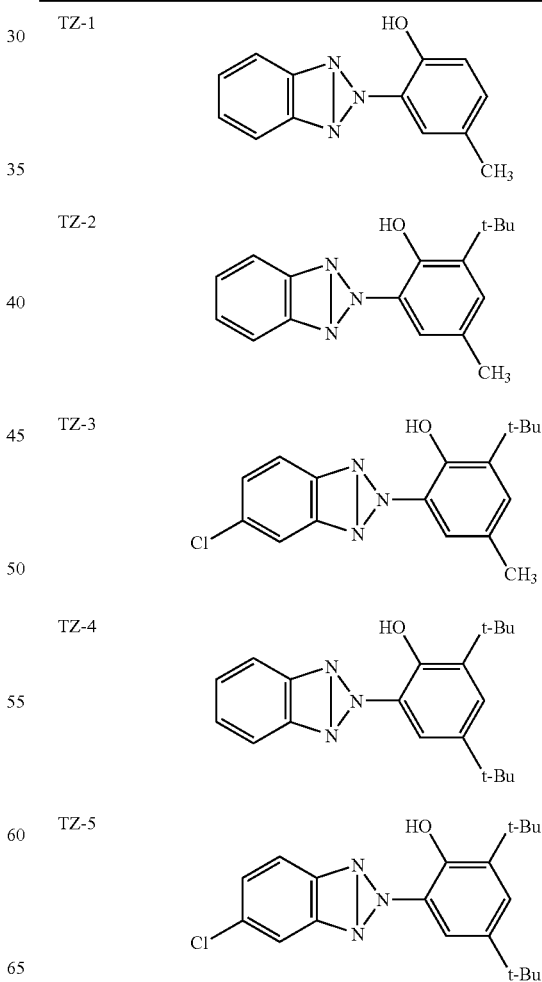

TABLE 50-continued
TZ-6 
TZ-7 
TZ-8 
TZ-9 
TZ-10 
TZ-11 
TZ-12 
TABLE 50-continued
TZ-13 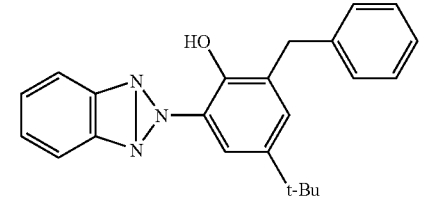
TZ-14 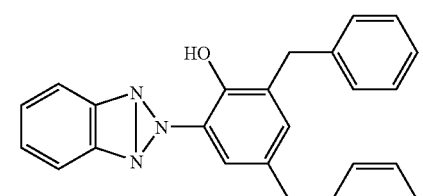
TZ-15 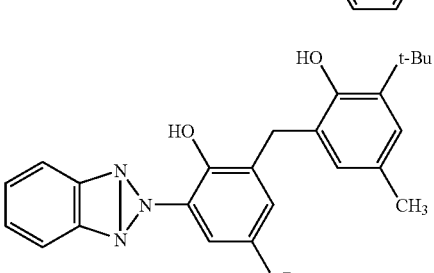
TABLE 51
TZ-16 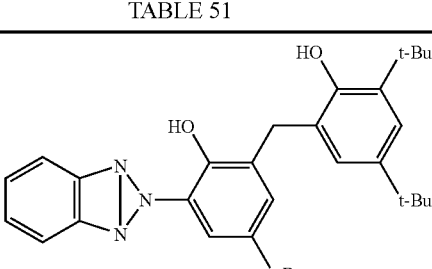
TZ-17 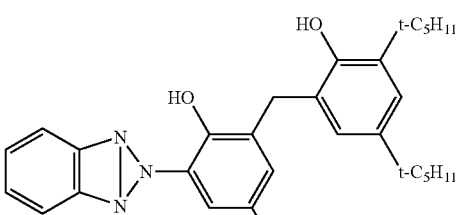
TZ-18 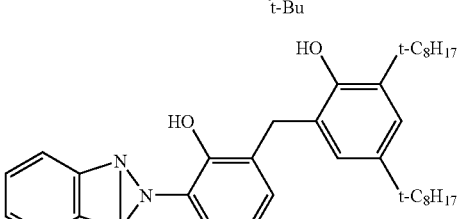

TABLE 51-continued

TZ-19 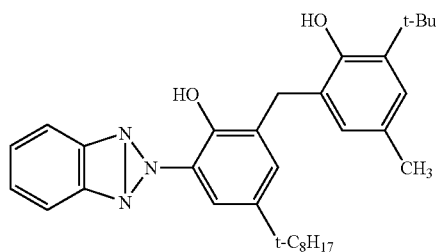

TZ-20 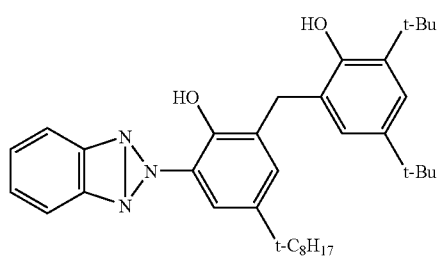

TZ-21 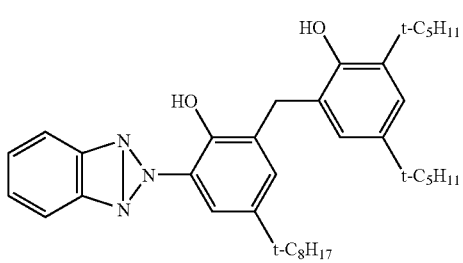

TZ-22 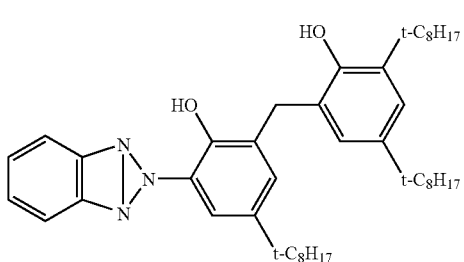

TZ-23 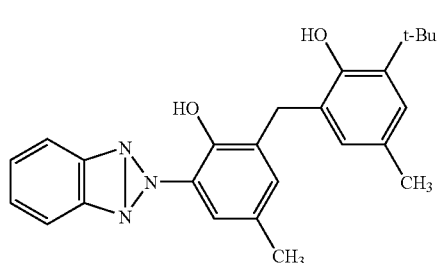

TZ-24 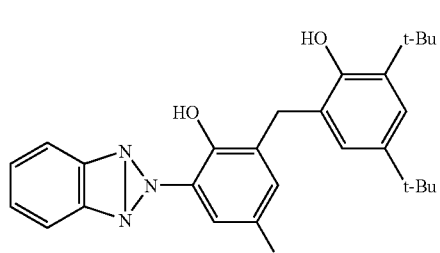

TABLE 51-continued

TZ-25 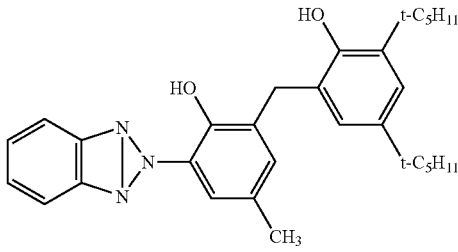

TZ-26 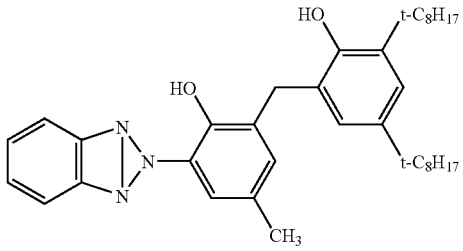

TABLE 52

TZ-27 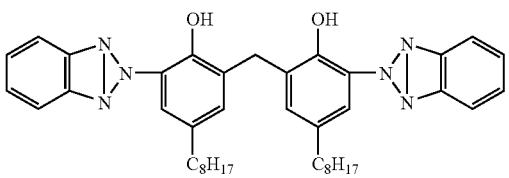

TZ-28 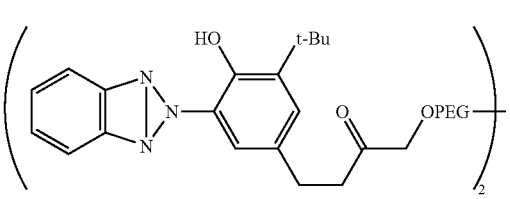

(PEG is polyethylene glycol residue (molecular weight: about 300))

In addition to the antioxidants shown in Table 33 to Table 46 and the light stabilizers shown in Table 47 to Table 52, the compound that can be used as the antioxidant or the light stabilizer include, for example, Exemplified Compounds X-1 to X-20 shown in the following Tables 53 to Table 55.

TABLE 53

X-1 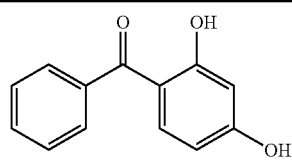

X-2 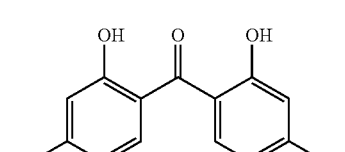

TABLE 53-continued
X-3 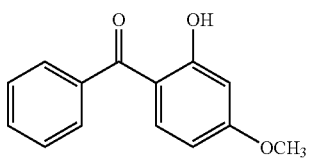
X-4 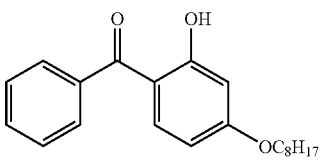
X-5 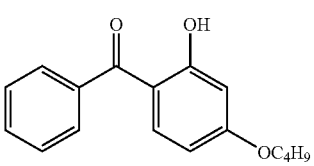
X-6 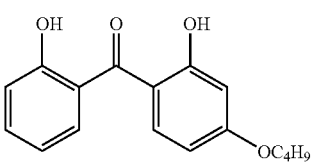
X-7 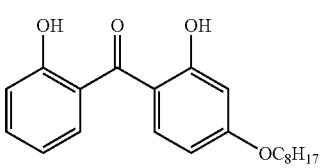
X-8 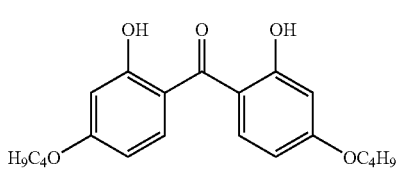
TABLE 54
X-9 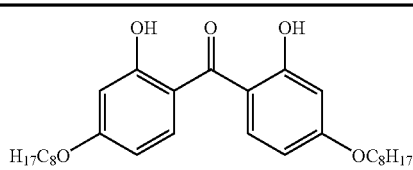
X-10 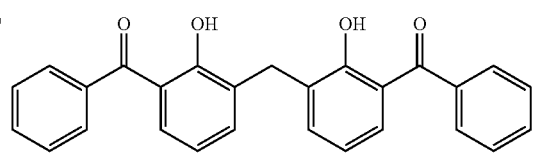
X-11 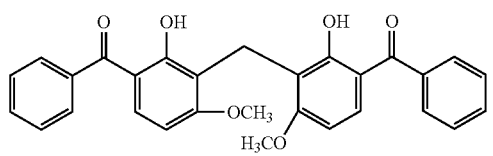
TABLE 54-continued
X-12 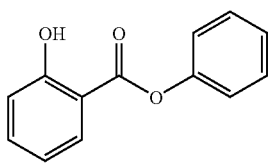
X-13 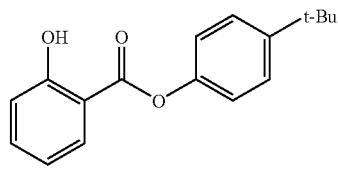
X-14 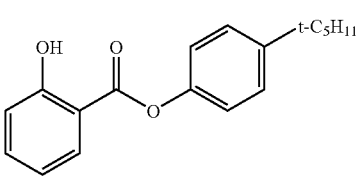
X-15 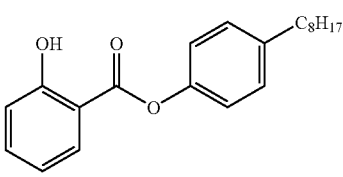
X-16 
TABLE 55
X-17 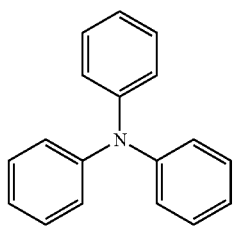
X-18 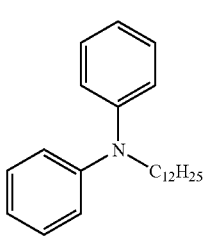

TABLE 55-continued

X-19
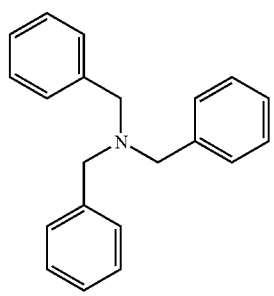

X-20
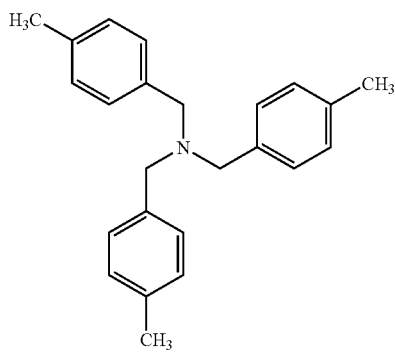

The antioxidants and the light stabilizers shown in Table 33 to Table 55 can be synthesized by various methods and are also available as commercial products.

As the antioxidant and the light stabilizer, those selected from the group consisting of the exemplified compounds shown in Table 33 to Table 55 are used each alone or two or more of them in admixture.

The antioxidant is contained in the light sensitive layer 14 preferably within a range of 0.1% by weight or more and 15% by weight or less, or, more preferably, within a range of 0.1% by weight or more and 5% by weight or less.

Further, the light stabilizer is contained in the light sensitive layer 14 preferably within a range of 0.1% by weight or more and 10% by weight or less, or, more preferably, within a range of 0.1% by weight or more and 5% by weight or less.

Further in a case where both of the antioxidant and the light stabilizer are contained in the photosensitive layer 14, the total content for the antioxidant and the light stabilizer in the photosensitive layer 14 is, preferably, 0.1% by weight or more and 20% by weight or less and, more preferably, 0.1% by weight or more and 10% by weight or less.

A sufficient effect can be obtained for the improvement of the durability of the electrophotographic photoreceptor 1 and the improvement for the stability of the coating solution by selecting the content for the antioxidant, the content for the light stabilizer, or the total content for the antioxidant and the light stabilizer in the photosensitive layer 14. Further, lowering of the characteristics of the electrophotographic photoreceptor 1 by the incorporation of the antioxidant and the light stabilizer can be minimized.

In a case where the content of the antioxidant, the content of the light stabilizer and the total content of the antioxidant and the light stabilizer in the photosensitive layer 14 is less than 0.1% by weight, no sufficient effect can be obtained for the improvement of the durability of the photoreceptor 1 and the improvement for the stability of the coating solution. Further, in a case where the content of the antioxidant exceeds 15% by weight, the content of the light stabilizer exceeds 10% by weight or the total content of the antioxidant and the light stabilizer exceeds 20% by weight in the photosensitive layer 14, this gives an undesired effect on the characteristics of the photoreceptor. Accordingly, they are defined within the ranges described above.

The charge transporting layer 16 is formed in a state where the charge transporting substance 13 containing the enamine compound represented by the general formula (1) is bond to the binder resin 17. As the binder resin 17 for the charge transporting layer 16, those of excellent compatibility with the charge transporting substance 13 are selected. Specific examples of the resin used for the binder resin 17 can include, for example, polymethyl methacrylate resin, polystyrene resin, vinyl polymer resin such as polyvinyl chloride and copolymer resin containing two or more of repetitive units constituting them, as well as polycarbonate resin, polyester resin, polyester carbonate resin, polysulfone resin, phenoxy resin, epoxy resin, silicone resin, polyallylate resin, polyamide resin, polyether resin, polyurethane resin, polyacryl amide resin, and phenol resin. Thermosetting resins formed by partially crosslinking the resins described above may also be included. One of the resins may be used alone or two or more of them may be used in admixture. Among the resins, since the polystyrene resins, polycarbonate resins, polyallylate resins, or polyphenylene oxides have a volume resistivity of $10^{13}$ Ω·cm or more and excellent in electrical insulative property and also excellent in film property and potential property, they are used particularly preferably for the binder resin 17.

The ratio A/B for the weight A of the charge transporting substance 13 and the weight B for the binder resin 17 in the charge transporting layer 16 is preferably from 10/12 to 10/30. In a case of using the known charge transporting substance, since the light responsivity may sometimes be lowered in a case where the ratio A/B is 10/12 or less by increasing the ratio of the binder resin 17, the ratio A/B is about 10/12. However, in the electrophotographic photoreceptor 1 of this embodiment, since the enamine compound of high charge movability represented by the general formula (1) is used for the charge transporting substance 13, even when the binder resin 17 is added at a higher ratio than in the case of using the known charge transporting substance, at the ratio A/B of from 10/12 to 10/30, the light responsivity can be maintained. Accordingly, the printing resistance of the charge transporting layer 16 can be improved to improve the durability of the electrophotographic photoreceptor 1 by increasing the content of the binder resin 17 in the charge transporting layer 16 with the ratio A/B being at 10/12 to 10/30 without lowering the light responsivity.

In a case where the ratio A/B exceeds 10/12 and the ratio of the binder resin 17 is lowered, the printing resistance of the charge transporting layer 16 is lowered and the amount of wear of the photosensitive layer 14 is increased compared with a case where the ratio of the binder resin 17 is higher. Further, in a case where the ratio A/B is less than 10/30 and the ratio of the binder resin 17 is increased, since the viscosity of the coating solution increases to lower the coating speed in a case of forming the charge transporting layer 16 by a dip coating method to be described later, the productivity is worsened remarkably. Further, in a case where the amount of a solvent in the coating solution is increased in order to suppress the increase of the viscosity of the coating solution, brushing phenomenon occurs and clouding occurs in the formed charge transporting layer 16. Accordingly, the ratio A/B is defined as 10/12 to 10/30.

For improving the film forming property, the flexibility and the surface smoothness, additives such as a plasticizer or a leveling agent may also be added as required to the charge transporting layer 16. The plasticizer includes, for example, dibasic acid esters such as phthalate ester, fatty acid ester, phosphate ester, chlorinated paraffin, and epoxy plasticizer. The leveling agent can include, for example, silicone type leveling agent.

Further, for increasing the mechanical strength or improving the electric property, fine particles of an inorganic compound or an organic compound may also be added to the charge transport layer 16.

The charge transporting layer 16 is formed, for example, by dissolving or dispersing a charge transporting substance 13 containing the enamine compound represented by the general formula (1) and a binder resin 17 in an appropriate solvent to prepare a coating solution for charge transporting layer and coating the outer circumferential surface of the charge generating layer 15 with the obtained coating solution. In a case of incorporating the antioxidant and the light stabilizer in the charge transporting layer 16, a coating solution for charge transporting layer is prepared by dissolving the antioxidant and the light stabilizer together with the charge transporting substance 13 and the binder resin 17 in an appropriate solvent. Further, additives such as a plasticizer, leveling agent, or fine particles described above are added as required to the coating solution for charge transporting layer.

The solvent for the coating solution for charge transporting layer can include, for example, aromatic hydrocarbons such as benzene, toluene, xylene, and monochlorobenzene, halogenated hydrocarbons such as dichloromethane and dichloroethane, ethers such as tetrahydrofuran (THF), dioxane, and dimethoxymethyl ether, as well as aprotic polar solvents such N,N-dimethylformamide are used each alone or in admixture of two or more of them. Further, a solvent such as alcohols, acetonitrile, or methyl ethyl ketone may further be added to the solvent described above and used.

The coating method for the coating solution for charge transporting layer includes, for example, a spraying method, bar coating method, roll coating method, blade method, wringing method, or dip coating method. Among the coating methods described above, an optimal method can be selected while taking the physical property of the coating and the productivity into consideration. Among the coating methods described above, the dip coating method is a method of dipping a substrate into a coating bath filled with a coating solution and then pulling up the substrate at a constant speed or at a gradually changing speed to form a layer on the surface of the substrate and, since the method is relatively simple and excellent in view of the productivity and the cost, it has been often utilized in a case of manufacture an electrophotographic photoreceptor and also often utilized in a case of forming the charge transporting layer 16.

The film thickness of the charge transporting layer 16 is, preferably, 5 μm or more and 50 μm or less and, more preferably, 10 μm or more and 40 μm or less. In a case where the film thickness of the charge transporting layer 16 is less than 5 μm, the charge retainability on the surface of the photoreceptor is lowered. In a case where the film thickness of the charge transporting layer 16 exceeds 50 μm, resolution power of the photoreceptor 1 is lowered. Accordingly, it is defined as 5 μm or more and 50 μm or less.

The charge generating layer 15 contains the charge generating substance 12 as a main ingredient. The material effective as the charge generating substance 12 can include azo pigments such as a monoazo pigment, bisazo pigment, and trisazo pigment, indigo pigments such as indigo and thioindigo, perylene pigments such as peryleneimide and perylenic acid anhydride, polynuclear quinone pigments such as anthraquinone and pyrenequinone, phthalocyanine pigments such as metal phthalocyanines and non-metal phthalocyanines, squarylium dyes, pyrylium salts, and thiopyrylium salts, triphenylmethane dyes, and inorganic materials such as selenium and amorphous silicon. The charge generating substances may be used each alone or two or more of them may be used in combination.

Among the charge generating substances described above, use of oxotitanium phthalocyanine is preferred. Since oxotitanium phthalocyanine is a charge generating substance having high charge generating efficiency and charge injecting efficiency, it generates a great amount of charges by absorption of light and efficiently injects the generated charges, without accumulating them in the inside thereof, into the charge transporting substance 13. Further, since the enamine compound of high charge movability represented by the general formula (1) is used for the charge transporting substance 13, the charges generated from oxotitanium phthalocyanine as the charge generating substance 12 by light absorption are efficiently injected into the enamine compound represented by the general formula (1) as the charge transporting substance 13 and transported smoothly to the surface of the photosensitive layer 14. Accordingly, electrophotographic photoreceptor 1 of high sensitivity and high resolution power can be obtained by using oxotitanium phthalocyanine as the charge generating substance 12.

The charge generating substance 12 may be used in combination with sensitizing dyes, for example, triphenylmethane dyes typically represented by methyl violet, crystal violet, night blue, and Victoria blue, acrydine dyes typically represented by erythrosin, rhodamine B, rhodamine 3R, acrydine orange, and fraveosin, thiazine dyes typically represents by methylene blue and methylene green, oxazine dyes typically represented by capri blue and merdora blue, cyanine dyes, stylyl dyes, pyrylium salt dyes, or thiopyrylium salt dyes.

The method of forming the charge generating layer 15 can include, for example, a method of vacuum vapor depositing the charge generating substance 12 on the outer circumferential surface of the conductive substrate 11, or a method of coating a coating solution for charge generating layer obtained by dispersing the charge generating substance 12 in an appropriate solvent to the outer circumferential surface of the conductive substrate 11 is used. Among them, a method of dispersing the charge generating substance 12 into a binder resin solution obtained by mixing a binder resin as a binder into an appropriate solvent by a known method to prepare a coating solution for charge generating layer and coating the outer circumferential surface of the conductive substrate 11 with the obtained coating solution is used suitably. The method is to be described below.

The binder resin used for the charge generating layer 15 can include those resins, for example, polyester resin, polystyrene resin, polyurethane resin, phenol resin, alkyd resin, melamine resin, epoxy resin, silicone resin, acryl resin, methacryl resin, polycarbonate resin, polyarylate resin, phenoxy resin, polyvinyl butyral resin, and polyvinyl formal resin, as well as copolymer resins containing two or more of repetitive units constituting the resins described above. Specific examples of the copolymer resins include, for example, those insulative resins such as vinyl chloride-vinyl acetate copolymer resin, vinyl chloride-vinyl acetate-maleic acid anhydride copolymer resin, and acrylonitrile-styrene copolymer resin. The binder resin is not restricted to them but those resins used generally can be used as the binder resin. The resins may be used each alone or two or more of them may be used in admixture.

For the solvent of the coating solution for charge generating layer, halogenated hydrocarbons such as dichlomethane or dichloroethane, ketones such as acetone, methyl ethyl ketone or cyclohexanone, esters such as ethyl acetate or butyl acetate, ethers such as tetrahydrofuran (THF) or dioxane, alkyl ethers of ethylene glycol such as 1,2-dimethoxyethane, aromatic hydrocarbons such as benzene, toluene or xylene, or aprotic polar solvent such as N,N-dimethylformamide and N,N-dimethylacetamide are used. Further, a mixed solvent formed by mixing two or more of the solvents can also be used.

As the blending ratio between the charge generating substance 12 and the binder resin, it is preferred that the ratio of the charge generating substance 12 is within a range from 10% by weight to 99% by weight. In a case where the ratio of the charge generating substance 12 is less than 10% by weight, the sensitivity is lowered. In a case where the ratio of the charge generating substance 12 exceeds 99% by weight, since not only the film strength of the charge generating layer 15 is lowered but also the dispersibility of the charge generating substance 12 is lowered to increase coarse particles and sometimes decrease the surface charges at the portion other than the portion to be erased by exposure, this increases image defects, particularly, image fogging referred to as "black spot" where toners are deposited to the white back ground to form fine black spots. Accordingly, it is defined as from 10% by weight to 99% by weight.

Before being dispersed in the binder resin solution, the charge generating substance 12 may previously be pulverized by a pulverizer. The pulverizer used for pulverization include, for example, a ball mill, sand mill, attritor, vibration mill, and supersonic dispersing machine.

The dispersing machine used upon dispersing the charge generating substance 12 into the binder resin solution can include, for example, a paint shaker, ball mill, and sand mill. As the dispersion conditions, appropriate conditions are selected so as not to cause intrusion of impurities due to abrasion of members constituting the container or dispersing machine to be used.

In a case of incorporating the antioxidant and the light stabilizer in the charge generating layer 15, the antioxidant and the light stabilizer are dissolved together with the charge generating substance 12 into an appropriate solvent or a binder resin solvent to prepare a coating solution for charge generating layer.

The coating method of the coating solution for charge generating layer includes, for example, a spraying method, bar coating method, roll coating method, blade method, wringing method, and dip coating method. Among the coating methods described above, since the dip coating method is particularly excellent with various view points as described above, it has been often utilized also in a case of forming the charge generating layer 15. For the apparatus used for the dip coating method, a coating solution dispersing apparatus typically represented by a supersonic generation apparatus may be provided in order to stabilize the dispersibility of the coating solution.

The film thickness of the charge generating layer 15 is, preferably, 0.05 µm or more and 5 µm or less and, more preferably, 0.1 µm or more and 1 µm or less. In a case where the film thickness of the charge generating layer 15 is less than 0.05 µm, the light absorption efficiency is lowered to lower the sensitivity. In a case where the film thickness of the charge generating layer 15 exceeds 5 µm, the charge transfer in the charge generating layer constitutes a rate determining step in the process of erasing charges on the surface of the photoreceptor to lower the sensitivity. Accordingly, it is defined as 0.05 µm or more and 5 µm or less.

As described above, the photoconductive layer constituting the photosensitive layer 14 comprises a stacked structure of the charge generating layer 15 and the charge transporting layer 16 formed as described above. By sharing the charge generation function and the charge transportation function to separate layers, since materials optimal to the charge generation function and the charge transportation function respectively can be selected for the material constituting each of the layers, it is possible to obtain an electrophotographic photoreceptor 1 having further higher sensitivity and having high durability with further increased stability during repetitive use.

As the conductive material constituting the conductive substrate 11, metal materials, for example, elemental metals such as aluminum, copper, zinc, or titanium, as well as alloys such as aluminum alloys or stainless steels can be used. Further, with no particular restriction to such metal materials, polymeric materials such as polyethylene terephthalate, nylon, or polystyrene, hard paper or glass in which metal foils are laminated, metal materials are vapor deposited, or layers of a conductive compounds such as a conductive polymer, tin oxide, or indium oxide are vapor deposited or coated on the surface thereof can also be used. The conductive materials are fabricated into a predetermined shape for use. While the shape of the conductive substrate 11 is cylindrical in this embodiment, it is not restrictive but may be a circular columnar shape, sheet like shape, or endless belt shape.

The surface of the conductive substrate 11 may optionally be applied with an anodizing treatment, a surface treatment with chemicals or hot water, a coloring treatment or a random reflection treatment, for example, by surface roughening, within a range not affecting the picture quality. In the electrophotographic process using a laser as an exposure source, since the wavelength of laser beams is coherent, an laser light incident to and a light reflected from the photoreceptor may sometimes cause interference, and interference fringes caused by the interference may sometimes appear on the images to result in image defects. Image defects by the interference of the laser light of the coherent wavelength can be prevented by applying the treatment described above to the surface of the conductive substrate 11.

As has been described above, while the photosensitive layer 14 is constituted with a photoconductive layer in which the charge generating layer 15 and the charge transporting layer 16 are stacked in this order on the outer circumferential surface of the conductive substrate 11 in this embodiment, this is not restrictive but it may be constituted with a photoconductive layer in which the charge transporting layer 16 and the charge generating layer 15 are stacked in this order on the outer circumferential surface of the conductive substrate 11. FIG. 2 is a cross sectional view schematically showing the constitution of an electrophotographic photoreceptor 2 as a second embodiment of the invention. The electrophotographic photoreceptor 2 of this embodiment is similar to the electrophotographic photoreceptor 1 of the first embodiment, so that corresponding components will be denoted by the same reference numerals, and description thereof will be omitted.

In the electrophotographic photoreceptor 2, it is to be noted that an intermediate layer 18 is provided between a conductive substrate 11 and a photosensitive layer 14.

In a case where the intermediate layer 18 is not present between the conductive substrate 11 and the photosensitive layer 14, charges are injected from the conductive substrate 11 to the photosensitive layer 14, the chargeability of the photosensitive layer 14 is lowered, and surface charges at a portion other than the portion to be eliminated by exposure are decreased to sometimes cause defects such as fogging to images. Particularly, in a case of forming images by using a reversal development process, since toners are deposited to a portion where the surface charges are decreased by exposure to form toner images, when the surface charges are decreased by the factors other than exposure, the toners are deposited to a white background and form minute black spots to case fogging to the images referred to as black pots to sometimes deteriorate a picture quality remarkably. That is, in a case where the intermediate layer 18 is not present between the conductive substrate 11 and the photosensitive layer 14, chargeability is lowered in a minute region caused by the defects of the conductive substrate 11 or the photosensitive layer 14 to sometimes cause fogging of images such as black spots to result in remarkable image defects.

In the electrophotographic photoreceptor 2 of this embodiment, since the intermediate layer 18 is provided between the conductive substrate 11 and the photosensitive layer 14 as described above, injection of charges from the conductive substrate 11 to the photosensitive layer 14 can be prevented. Accordingly, lowering of the chargeability of the photosensitive layer 14 can be prevented, decrease of the surface charges in the portion other than the portion to be eliminated by exposure can be suppressed and formation of defects to images such as fogging can be prevented.

In addition, the intermediate layer 18 may cover the surface defects of the conductive 11 to thereby make the substrate have a uniform surface, and the film-forming ability of the photosensitive layer 14 is therefore enhanced. Further, the intermediate layer 15 prevents the photosensitive layer 14 from being peeled off from the conductive substrate 11, and the adhesiveness between the conductive substrate 11 and the photosensitive layer 14 is thereby enhanced.

The intermediate layer 18 may be a resin layer of various resin materials or an alumite layer.

The resin material to form the resin layer includes, for example, various resins such as polyethylene resins, polypropylene resins, polystyrene resins, acrylic resins, polyvinyl chloride resins, polyvinyl acetate resins, polyurethane resins, epoxy resins, polyester resins, melamine resins, silicone resins, polyvinyl butyral resins and polyamide resins; copolymer resins containing at least two repetitive units of these resins; casein, gelatin, polyvinyl alcohol, and ethyl cellulose. Of those, especially preferred are polyamide resins. Also preferred are alcohol-soluble nylon resins. Preferred examples of the alcohol-soluble nylon resins are so-called copolymer nylons prepared through copolymerization with 6-nylon, 6,6-nylon, 6,10-nylon, 11-nylon, 2-nylon, or 12-nylon; and chemically-modified nylon resins such as N-alkoxymethyl-modified nylon and N-alkoxyethyl-modified nylon.

The intermediate layer 18 may contain particles such as metal oxide particles or the like. The particles may control the volume resistivity of the intermediate layer 15 and will be effective for further preventing the charge injection from the conductive substrate 11 to the photosensitive layer 14, and, in addition, they may ensure the electric properties of the photoreceptors under different conditions.

The metal oxide particles may be, for example, particles of titanium oxide, aluminum oxide, aluminum hydroxide or tin oxide.

The intermediate layer 18 is formed, for example, by dissolving or dispersing the resin described above in an appropriate solvent to prepare a coating liquid for intermediate layer, and coating the outer circumferential surface of the conductive substrate 11 with the coating liquid. In a case of particles such as metal oxide particles described above in the intermediate layer 18, for example, the intermediate layer 18 can be formed by dispersing the particles in a resin solution obtained by dissolving the resin described above in an appropriate solvent to prepare a coating liquid for intermediate layer, and coating the surface of the conductive substrate 11 with the coating liquid.

For the solvent of the coating liquid for intermediate layer, water or various kinds of organic solvents or mixed solvents of them may be used. For example, a single solvent of water, methanol, ethanol or butanol or a mixed solvent such as of water and alcohol, two or more kinds of alcohols, acetone or dioxolane and alcohols, and chlorine type solvent such as dichloroethane, chloroform or trichloroethane and alcohols are used. Among the solvents, non-halogen organic solvents are preferably used in view of the global environment.

For the method of dispersing the particles in a resin solution, ordinary methods including the use of using a ball mill, sand mill, attritor, vibration mill, or ultrasonic wave dispersing machine can be used.

In the coating liquid for intermediate layer the ratio of the total content C of the resin and the metal oxide to the solvent content D of the coating liquid, C/D by weight preferably falls between 1/99 and 40/60, more preferably between 2/98 and 30/70. The ratio by weight of the content of the resin to the content of the metal oxide (resin/metal oxide), preferably falls between 90/10 and 1/99, more preferably between 70/30 and 5/95.

For applying the coating liquid for intermediate layer to the substrate, employable is a method of spraying, bar coating, roll coating, blade coating, ring coating or dipping. As so mentioned hereinabove, a dipping method is relatively simple and favorable in point of the productivity and the production costs, and it is much utilized in forming the intermediate layer 18.

The thickness of the intermediate layer 18 is preferably from 0.01 µm to 20 µm, more preferably from 0.05 µm to 10 µm. When the intermediate layer 18 is thinner than 0.01 µm, it could not substantially function as an intermediate layer 18, or that is, it could not cover the defects of the conductive substrate 11 to form a uniform surface, and it could not prevent the charge injection from the conductive substrate 11 to the photosensitive layer 14. As a result, the chargeability of the photosensitive layer 14 will lower. When the intermediate layer 18 is thicker than 20 µm and when such a thick intermediate layer 18 is formed according to a dipping method, the intermediate layer 18 will be difficult to form and, in addition, a uniform photosensitive layer 14 could not be formed on the intermediate layer 18, and the sensitivity of the photoreceptor will lower. Therefore, such a thick layer is unfavorable for the intermediate layer 18. Accordingly, a preferred range for the thickness of the intermediate layer 18 is defined as 0.01 µm or more and 20 µm or less.

Figure 3:
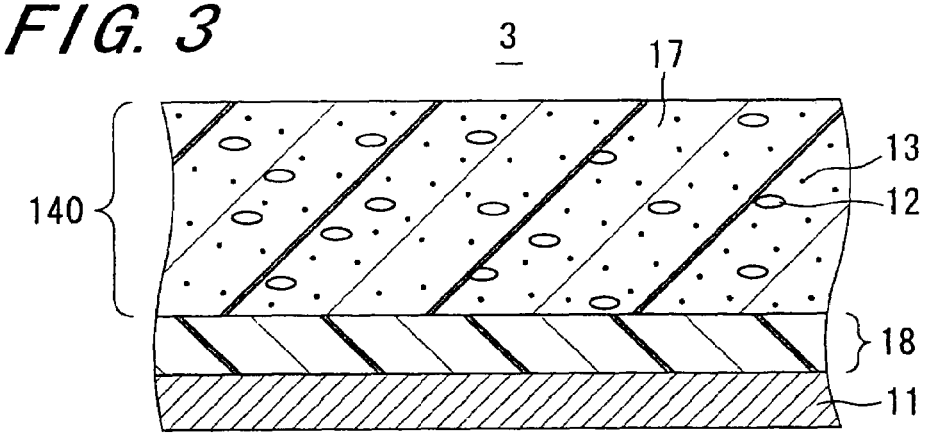
FIG. 3 is a cross sectional view schematically showing the constitution of an electrophotographic photoreceptor according to a third embodiment of the invention.

FIG. 3 is a cross sectional view schematically showing the constitution of an electrophotographic photoreceptor 3 according to a third embodiment of the invention. The electrophotographic photoreceptor 3 of this embodiment is similar to the electrophotographic photoreceptor 2 of the second embodiment, so that corresponding components will be denoted by the same reference numerals, and description thereof will be omitted.

In the electrophotographic photoreceptor 3, it is to be noted that the photosensitive layer 140 is constituted with a single layer containing a charge generating substance 12 and a charge transporting substance 13. That is, the electrophotographic photoreceptor 3 is a single layer type photoreceptor.

Like the first embodiment and the second embodiment, the enamine compound represented by the general formula (1) is used for the charge transporting substance 13 in this embodiment. Further, the photosensitive layer 140 contains at least one of the antioxidant and the light stabilizer. Accordingly, like in the first and second embodiments, it is possible to obtain a highly reliable electrophotographic photoreceptor 3 having high chargeability, sensitivity and light responsivity, not suffering from lowering of the characteristics described above even in a case where it is used under a low temperature circumstance or in a high speed electrophotographic process, or it is exposed to light, stable against an active gas such as ozone or NOx, UV-rays and heat, with less fatigue deterioration of the film after repetitive use.

The content of the antioxidant, the content of the light stabilizer, and the total content of the antioxidant and the light stabilizer in the photosensitive layer 140 are identical with the content of the antioxidant, the content of the light stabilizer, and the total content of the antioxidant and the light stabilizer in the photosensitive layer 14 of the first embodiment.

The photosensitive layer 140 is formed by the same method as for the charge transporting layer 16 disposed in the electrophotographic photoreceptor 1 of the first embodiment. For example, the photosensitive layer 140 can be formed by dissolving or dispersing the charge generating substance 12, the charge transporting substance 13 containing the enamine compound represented by the general formula (1), the binder resin 17, at least one of the antioxidant and the light stabilizer and, if necessary, the additives described above into an appropriate solvent like that of the coating solution for charge transporting layer to prepare a coating solution of photosensitive layer and coating the outer circumferential surface of an intermediate layer 18 with the coating solution for photosensitive layer, for example, by a dip coating method.

The ratio A'/B' for the weight A' of the charge transporting substance 13 and the weight B' for the binder resin 17 in the photosensitive layer 140 is preferably from 10/12 to 10/30 in the same manner as the ratio A/B for the weight A of the charge transporting substance 13 and for the weight B of the binder resin 17 in the charge transporting layer 16 of the first embodiment.

The thickness of the photosensitive layer 140 is, preferably, from 5 μm or more and 100 μm or less and, more preferably, 10 μm or more and 50 μm or less. In a case where the thickness of the photosensitive layer 140 is less than 5 μm, the charge retainability on the surface of the photoreceptor is lowered. In a case where the thickness of the photosensitive layer 140 exceeds 100 μm, the productivity is lowered. Accordingly, it is defined as 5 μm or more and 100 μm or less.

For the photosensitive layer 14 or 140, disposed to the electrophotographic photoreceptor 1, 2, or 3 for the first to third embodiments described above, one or more of electron accepting materials or dyes may also be added in order to improve the sensitivity and suppress the increase of the residual potential and fatigue during repetitive use.

As the electron accepting material, acid anhydrides, for example, succinic acid anhydride, maleic acid anhydride, phthalic acid anhydride, and 4-chloronaphthalic acid anhydride, cyano compounds such as tetracyanoethylene and terephthal malone dinitrile, aldehydes such as 4-nitrobenzaldehyde, anthraquinones such as anthraquinone and 1-nitroanthraquinone, polynuclear or heterocyclic nitro compounds such as 2,4,7-trinitrofluorenone and 2,4,5,7-tetranitrofuorenone, or electron accepting materials such as diphenoxy compounds can be used. Further, the polymerized electron accepting materials of them may also be used.

As the dye, for example, organic photoconductive compounds such as xanthene dye, thiazine dye, triphenylmethane dye, quinoline pigment or copper phthalocyanine can be used. Further, the organic photocnductive compounds function as the optical sensitizer.

Various layer constitutions can be adopted for the electrophotographic photoreceptor according to the invention not being restricted to the constitutions of the electrophotographic photoreceptors 1, 2, 3 of the first to third embodiments described above.

For example, in the electrophotographic photoreceptors 1, 2, and 3 of the first to third embodiments, a photosensitive layer 14 constituted with a photoconductive layer in which the charge generating layer 15 and the charge transporting layer 16 are stacked, or a photosensitive layer 140 constituted with a single photoconductive layer containing the charge generating substance 12 and the charge transporting substance 13 are provided, they are not limitative but a photosensitive layer formed by stacking a surface protective layer further on the photoconductive layer may also be provided.

By disposing the surface protective layer on the photoconductive layer, the printing resistance of the photosensitive layer can be improved and, at the same time, the undesired chemical effects of the active gas such as ozone or nitrogen oxide (NOx) generated by corona discharge upon charging the surface of the photoreceptor can be prevented further. For the surface protective layer, a layer formed of, for example, a resin, inorganic filler-containing resin or an inorganic oxide may be used.

In a case where the photosensitive layer has a surface protective layer stacked on the photoconductive layer, the antioxidant or the light stabilizer may be contained either in the photoconductive layer or in the surface protective layer and may be contained in both of the photoconductive layer and the surface protective layer.

Figure 4:
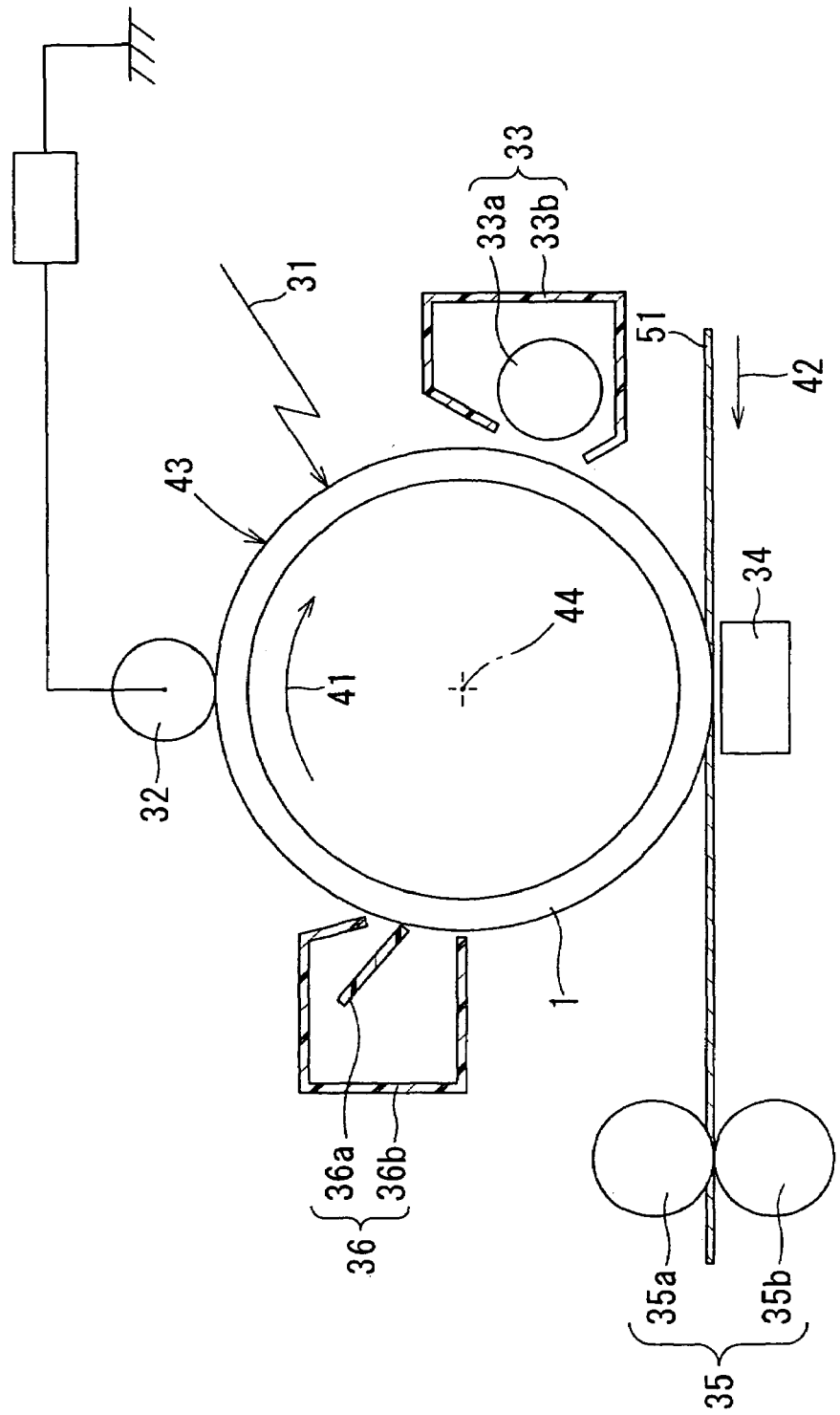
FIG. 4 is a side elevational view for an arrangement schematically showing the constitution of an image forming apparatus 100.

As an image forming apparatus of a fourth embodiment according to the invention, an image forming apparatus 100 having the electrophotographic photoreceptor 1 (photoreceptor 1) of the first embodiment described previously is illustrated. The image forming apparatus of the invention is not restricted to the contents of the following descriptions. FIG. 4 is a side elevational view for the arrangement schematically showing the constitution of the image forming apparatus 100.

The image forming apparatus 100 includes a photoreceptor 1 rotatably supported to an apparatus main body (not shown) and driving means (not shown) for rotationally driving the photoreceptor 1 around a rotational axis 44 in a direction of an arrow 41. The driving means has, for example, a motor as a source of power and rotationally drives the photoreceptor 1 at a predetermined circumferential speed by transmitting the power from the motor by way of gears (not shown) to a support constituting the core of the photoreceptor 1.

Around the periphery of the photoreceptor 1, a charger 32, exposure means (not shown), a developing device 33, a transfer device 34, and a cleaner 36 are arranged in this order from the upstream to the downstream in the rotational direction of the photoreceptor 1 shown by an arrow 41. The cleaner 36 is disposed together with a charge elimination lamp (not shown).

The charger 32 is charging means for charging the outer circumferential surface 43 of the photoreceptor 1 to a predetermined potential. The charger 32 is, for example, contact type charging means such as of a roller charging system.

The exposure means has, for example, a semiconductor laser as a light source and applies exposure in accordance with image information to the charged outer circumferential surface 43 of the photoreceptor 1 by irradiating the outer circumferential surface 43 of the photoreceptor 1 situated between the charger 32 and the developing device 33, with a light 31 such as a laser beam outputted from a light source.

The developing device 33 is developing means for developing electrostatic latent images formed by exposure at the outer circumferential surface 43 of the photoreceptor 1 by a developer, and has a developing roller 33a for supplying a toner to the outer circumferential surface 43 of the photoreceptor 1 disposed being opposed to the photoreceptor 1, and a casing 33b for rotatably supporting the developing roller 33a around a rotational axis in parallel with the rotational axis 44 of the photoreceptor 1 and housing the developer containing the toner in the inner space thereof.

The transfer device 34 is transfer means for transferring toner images as visible images formed by development at the outer circumferential surface 43 of the photoreceptor 1 by conveying means (not shown) onto a transfer paper 51 as a recording medium supplied by conveying means (not shown) in a direction of an arrow 42 to a position between the photoreceptor 1 and the transfer device 34. The transfer device 34 has, for example, charging means, which is non-contact type transfer means for giving electric charges at a polarity opposite to that of the toner to the transfer paper 51 and thereby transferring the toner images to the transfer paper 51.

The cleaner 36 is cleaning means for removing and recovering a toner remained on the outer circumferential surface 43 of the photoreceptor 1 after the transfer operation by the transfer device 34 and has a cleaning blade 36a for peeling the toner remaining on the outer circumferential surface 43 of the photoreceptor 1 from the outer circumferential surface 43 and a recovery casing 36b for containing the toner peeled by the cleaning blade 36a.

Further, a fixing device 35 as fixing means for fixing transferred images is provided in a direction in which the transfer paper 51 is conveyed after passage between the photoreceptor 1 and the transfer device 34. The fixing device 35 has a heating roller 35a having heating means (not shown), and a press roller 35b opposed to the heating roller 35a and pressed by the heating roller 35a to form an abutment portion.

The operation by the image forming apparatus 100 is to be described. At first, when the photoreceptor 1 is driven rotationally by the photoreceptor driving means in the direction of the arrow 41, the outer circumferential surface 43 of the photoreceptor 1 is uniformly charged to a predetermined positive or negative potential by the charger 32 which is disposed to the upstream of the focusing point of a light 31 from the exposure means in the rotational direction of the photoreceptor 1.

Then, the outer circumferential surface 43 of the photoreceptor 1 is irradiated with the light 31 from the exposure means. The light 31 from the light source is scanned repetitively in the longitudinal direction of the photoreceptor 1 as the main scanning direction. Exposure is applied in accordance with the image information to the outer circumferential surface 43 of the photoreceptor 1 by rotationally driving the photoreceptor 1 and scanning the light 31 from the light source repetitively. The surface charges at the portion being irradiated with the light 31 are eliminated by the exposure, and a difference is caused between the surface potential at a portion being irradiated with the light 31 and the surface potential at a portion being not irradiated with the light 31, to form electrostatic latent images to the outer circumferential surface 43 of the photoreceptor 1.

Then, a toner is supplied from the developing roller 33a of the developing device 33 disposed to the downstream of the focusing point of the light 31 from the light source in the rotational direction of the photoreceptor 1 to the outer circumferential surface 43 of the photoreceptor 1 formed with the electrostatic latent images. Thus the electrostatic latent images are developed and toner images are formed on the outer circumferential surface 43 of the photoreceptor 1.

Further, in synchronization with the exposure to the photoreceptor 1, the transfer paper 51 is supplied by the conveying means to a position between the photoreceptor 1 and the transfer device 34 in the direction of the arrow 42. When the transfer paper 51 is supplied between the photoreceptor 1 and the transfer device 34, the transfer device 34 gives electric charges at a polarity opposite to the polarity of the toner to the transfer paper 51. Thus, toner images formed on the outer circumferential surface 43 of the photoreceptor 1 are transferred on the transfer paper 51.

The transfer paper 51 transferred with the toner images is conveyed by the conveying means to the fixing device 35 and heated and pressurized upon passage through an abutment portion between the heating roller 35a and the pressure roller 35b of the fixing device 35. Thus, the toner images on the transfer paper 51 are fixed to form firm images on the transfer paper 51. The transfer paper 51 thus formed with the images is discharged by the conveying means to the outside of the image forming apparatus 100.

On the other hand, the toner remaining on the outer circumferential surface 43 of the photoreceptor 1 after the transfer operation by the transfer device 34 is separated by the cleaning blade 36a of the cleaner 36 from the outer circumferential surface 43 of the photoreceptor 1 and recovered in the recovery casing 36b. The charges on the outer circumferential surface 43 of the photoreceptor 1 thus removed with the toner are thus eliminated by a light from the charge elimination lamp, by which the electrostatic latent images on the outer circumferential surface 43 of the photoreceptor 1 are erased. Then the photoreceptor 1 is further driven rotationally and a series of operations starting from the charging of the photoreceptor 1 are repeated. As described above, images are formed continuously.

Since the photoreceptor 1 equipped in the image forming apparatus 100 has the photosensitive layer 14 containing the enamine compound represented by the general formula (1) as the charge transporting substance 13 and further containing at least one of the antioxidant and the light stabilizer, it has high chargeability, sensitivity, and light responsivity, does not suffer from lowering of the characteristics described above even in a case when it is used under a low temperature circumstance or in a high speed electrophotographic process, is stable against an active gas such as ozone or NOx, UV-rays and heat as described above, suffers from less fatigue degradation upon repetitive use and has high reliability. Accordingly, a highly reliable image forming apparatus 100 capable of providing high quality images stably for a long time under various circumstances can be obtained. Further, since the electrophotographic photoreceptor 1 of the invention does not suffer from lowering of the characteristics described above even in a case when it is exposed to light, it is possible to prevent lowering of the image quality caused by exposure of the electrophotographic photoreceptor 1 to the light during maintenance or the like to improve the reliability of the image forming apparatus 100.

As has been described above, while the image forming apparatus 100 of this embodiment has an electrophotographic photoreceptor 1 of the first embodiment, this is not restrictive and it may have the electrophotographic photoreceptor 2 of the second embodiment, the electrophotographic photoreceptor 3 of the third embodiment or an electrophotographic photoreceptor having a layer constitution different from the electrophotographic photoreceptor of the first to third embodiments 1, 2, and 3.

Further, while the charger 32 is contact type charging means, it is not restrictive but may also be a non-contact type charging means such as a corona discharging system.

Further, while the transfer device 34 is non-contact type transfer means having the charging means, for transferring toner images on the transfer paper 51 by applying charges at a polarity opposite to that of the toner to the transfer paper 51, this is not restrictive but may also be contact type transfer means having a roller, for transferring toner images on the transfer paper 51 by bringing the transfer paper 51 and the electrophotographic photoreceptor 1 in press contact with each other by using the rollers.

EXAMPLES

The present invention is to be describe further specifically by way of examples but the invention is not restricted to them.

Production Example 1

Production of Compound No. 1

Production Example 1-1

Production of Enamine Intermediate 23.3 g (1.0 equivalent) of N-(p-tolyl)-α-naphthylamine of the following structural formula (8), 20.6 g (1.05 equivalents) of diphenylacetaldehyde of the following structural formula (9), and 0.23 g (0.01 equivalent) of DL-10-camphorsulfonic acid were added to 100 ml of toluene and heated, and these were reacted for 6 hours while the side-product, water was removed out of the system through azeotropic distillation with toluene. After thus reacted, the reaction solution was concentrated to about 1/10, and gradually and dropwise added to 100 ml of hexane that was vigorously stirred, and this gave a crystal. The crystal was taken out through filtration, and washed with cold ethanol to obtain 36.2 g of a pale yellow powdery compound.

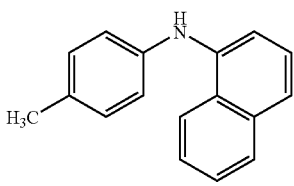

(8)

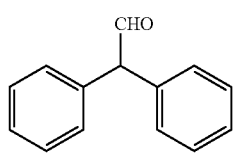

(9)

Thus obtained, the compound was analyzed through liquid chromatography-mass spectrometry (LC-MS), which gave a peak at 412.5 corresponding to the molecular ion [M+H]⁺ of an enamine intermediate (calculated molecular weight: 411.20) of the following structural formula (10) with a proton added thereto. This confirms that the compound obtained herein is the enamine intermediate represented by formula (10) (yield: 88%). In addition, the data of LC-MS further confirm that the purity of the enamine intermediate obtained herein is 99.5%.

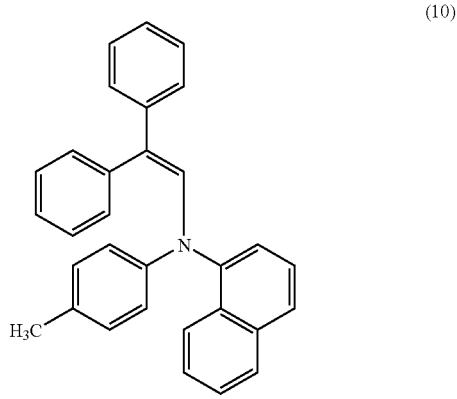

(10)

As in the above, the dehydrating condensation of N-(p-tolyl)-α-naphthylamine, a secondary amine represented by formula (8), and diphenylacetaldehyde, an aldehyde compound represented by formula (9) gives the enamine intermediate represented by formula (10).

Production Example 1-2

Production of Enamine-Aldehyde Intermediate 9.2 g (1.2 equivalents) of phosphorus oxychloride was gradually added to 100 ml of anhydrous N,N-dimethylformamide (DMF) and stirred for about 30 minutes to prepare a Vilsmeier reagent. 20.6 g (1.0 equivalent) of the enamine intermediate represented by formula (10) obtained in Production Example 1-1 was gradually added to the solution with cooling with ice. Next, this was gradually heated up to 80° C., and stirred for 3 hours while kept heated at 80° C. After thus reacted, the reaction solution was left cooled, and then this was gradually added to 800 ml of cold 4 N aqueous sodium hydroxide solution to form a precipitate. Thus formed, the precipitate was collected through filtration, well washed with water, and then recrystallized from a mixed solvent of ethanol and ethyl acetate to obtain 20.4 g of an yellow powdery compound.

Thus obtained, the compound was analyzed through LC-MS, which gave a peak at 440.5 corresponding to the molecular ion [M+H]⁺ of an enamine-aldehyde intermediate (calculated molecular weight: 439.19) of the following structural formula (11) with a proton added thereto. This confirms that the compound obtained herein is the enamine-aldehyde inter mediate represented by formula (11) (yield: 93%). In addition, the data of LC-MS further confirm that the purity of the enamine-aldehyde intermediate obtained herein is 99.7%.

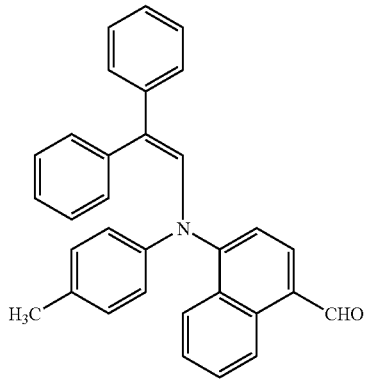

(11)

As in the above, the formylation of the enamine intermediate represented by formula (10) through Vilsmeier reaction gives the enamine-aldehyde intermediate represented by formula (11).

Production Example 1-3

Production of Compound No. 1

8.8 g (1.0 equivalent) of the enamine-aldehyde intermediate represented by formula (11) obtained in Production Example 1-2, and 6.1 g of diethyl cinnamylphosphonate of the following structural formula (12) were dissolved in 80 ml of anhydrous DMF, and 2.8 g (1.25 equivalents) of potassium t-butoxide was gradually added to the solution at room temperature, then heated up to 50° C., and stirred for 5 hours while kept heated at 50° C. The reaction mixture was left cooled, and poured into excess methanol. The deposit was collected, and dissolved in toluene to prepare a toluene solution thereof. The toluene solution was transferred into a separating funnel and washed with water, and the organic layer was taken out. Thus taken out, the organic layer was dried with magnesium sulfate. Solid matter was removed from the thus-dried organic layer, which was then concentrated and subjected to silica gel column chromatography to obtain 10.1 g of an yellow crystal.

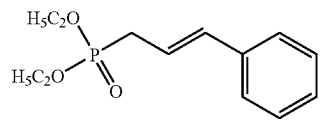

(12)

Thus obtained, the crystal was analyzed through LC-MS, which gave a peak at 540.5 corresponding to the molecular ion [M+H]+ of the intended enamine compound, Compound No. 1 in Table 1 (calculated molecular weight: 539.26) with a proton added thereto.

Figure 5:
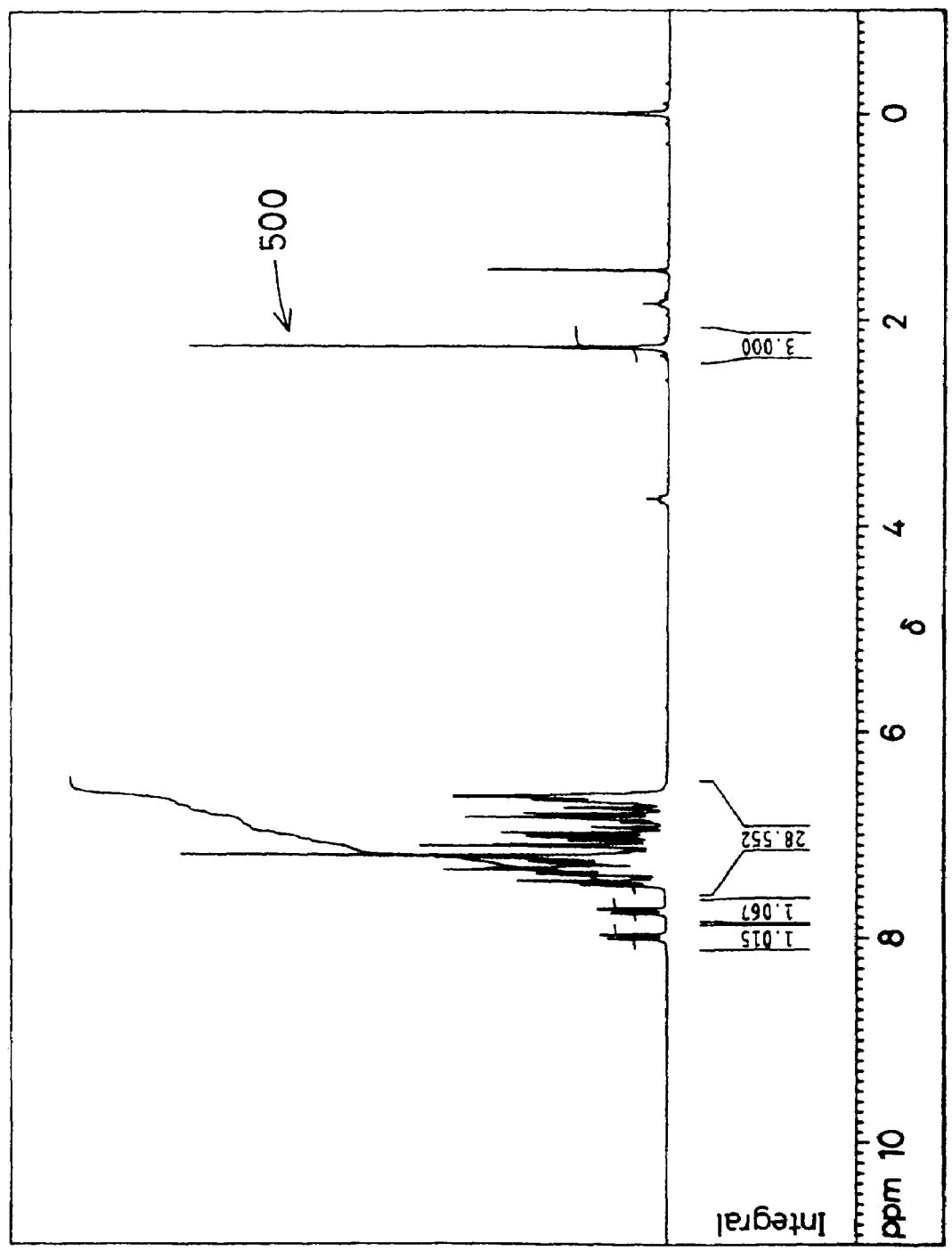
FIG. 5 is a $^1$H-NMR spectrum of a product in Production Example 1-3.
Figure 6:
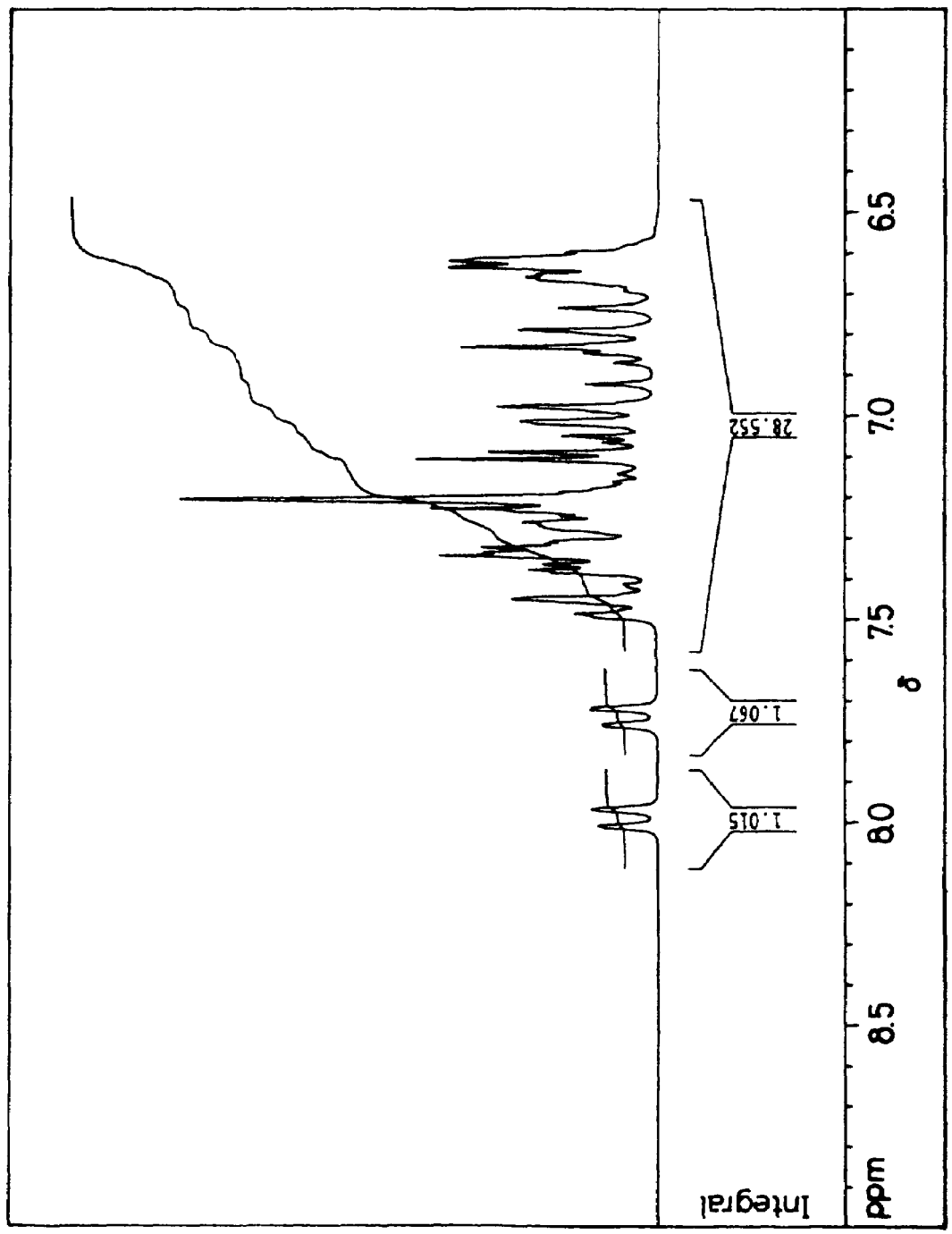
FIG. 6 is an enlarged view of the spectrum of FIG. 5 in the range of from 6 ppm to 9 ppm.
Figure 7:
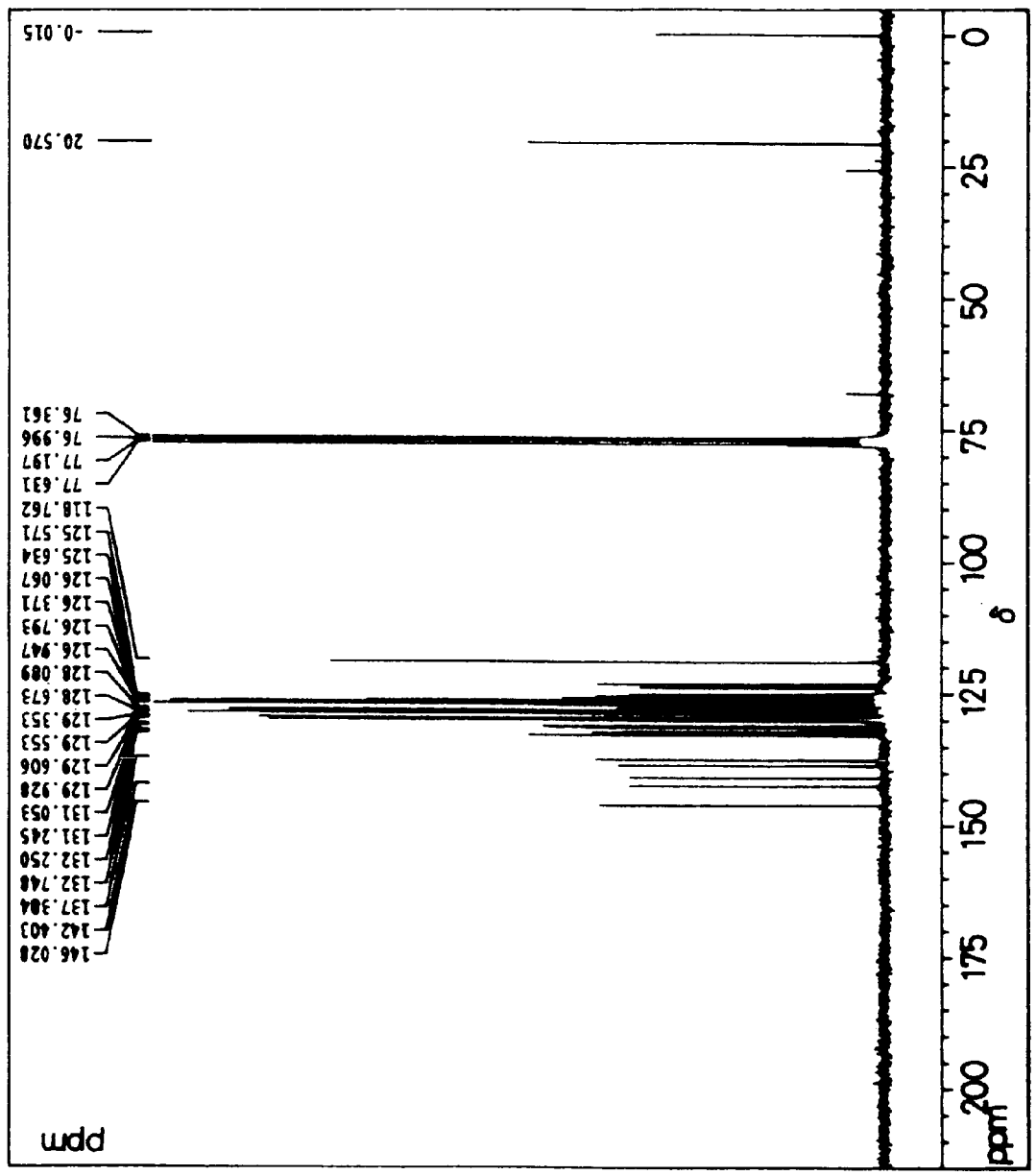
FIG. 7 is a $^{13}$C-NMR spectrum in ordinary measurement of the product in Production Example 1-3.
Figure 8:
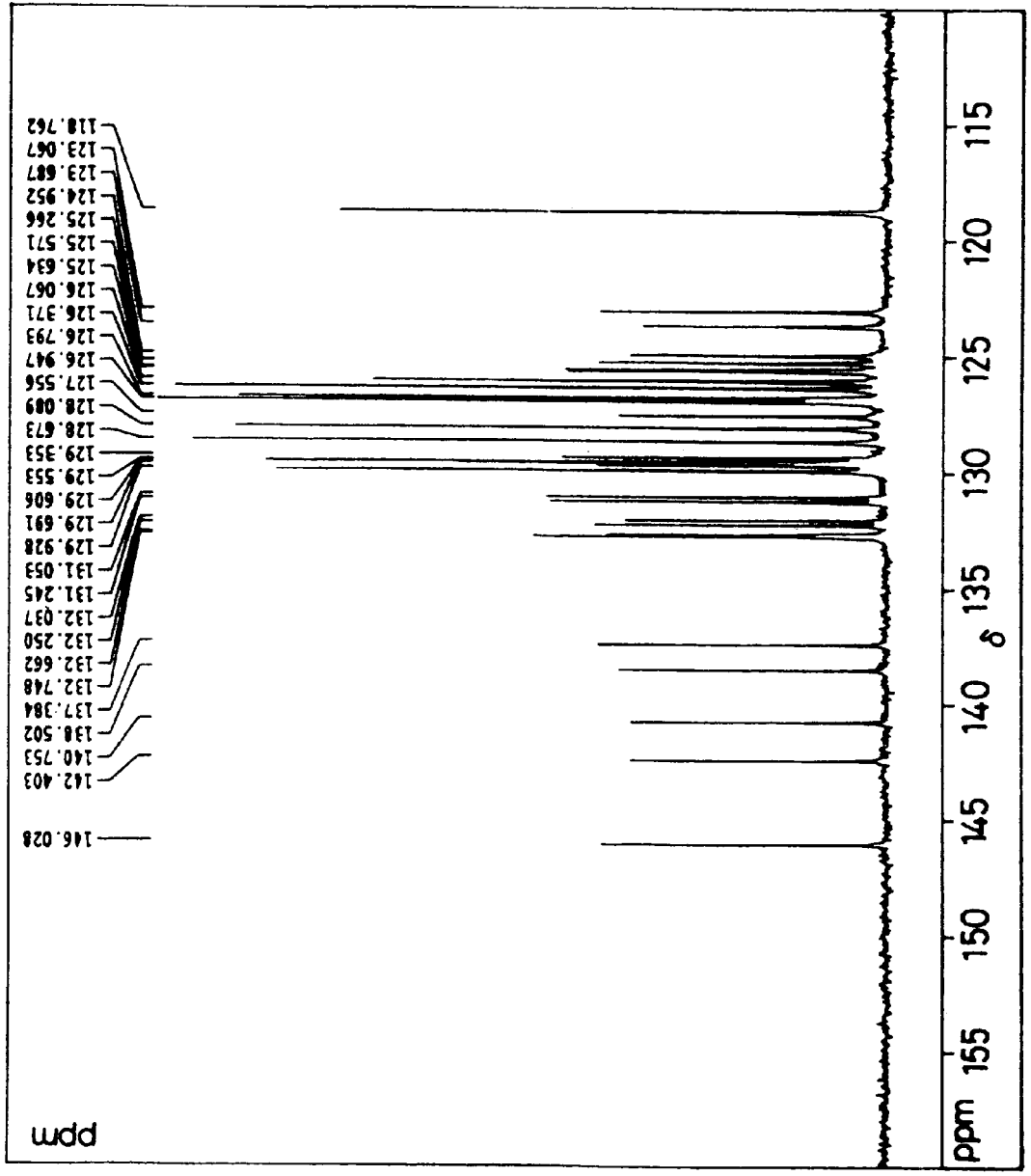
FIG. 8 is an enlarged view of the spectrum of FIG. 7 in the range of from 110 ppm to 160 ppm.
Figure 9:
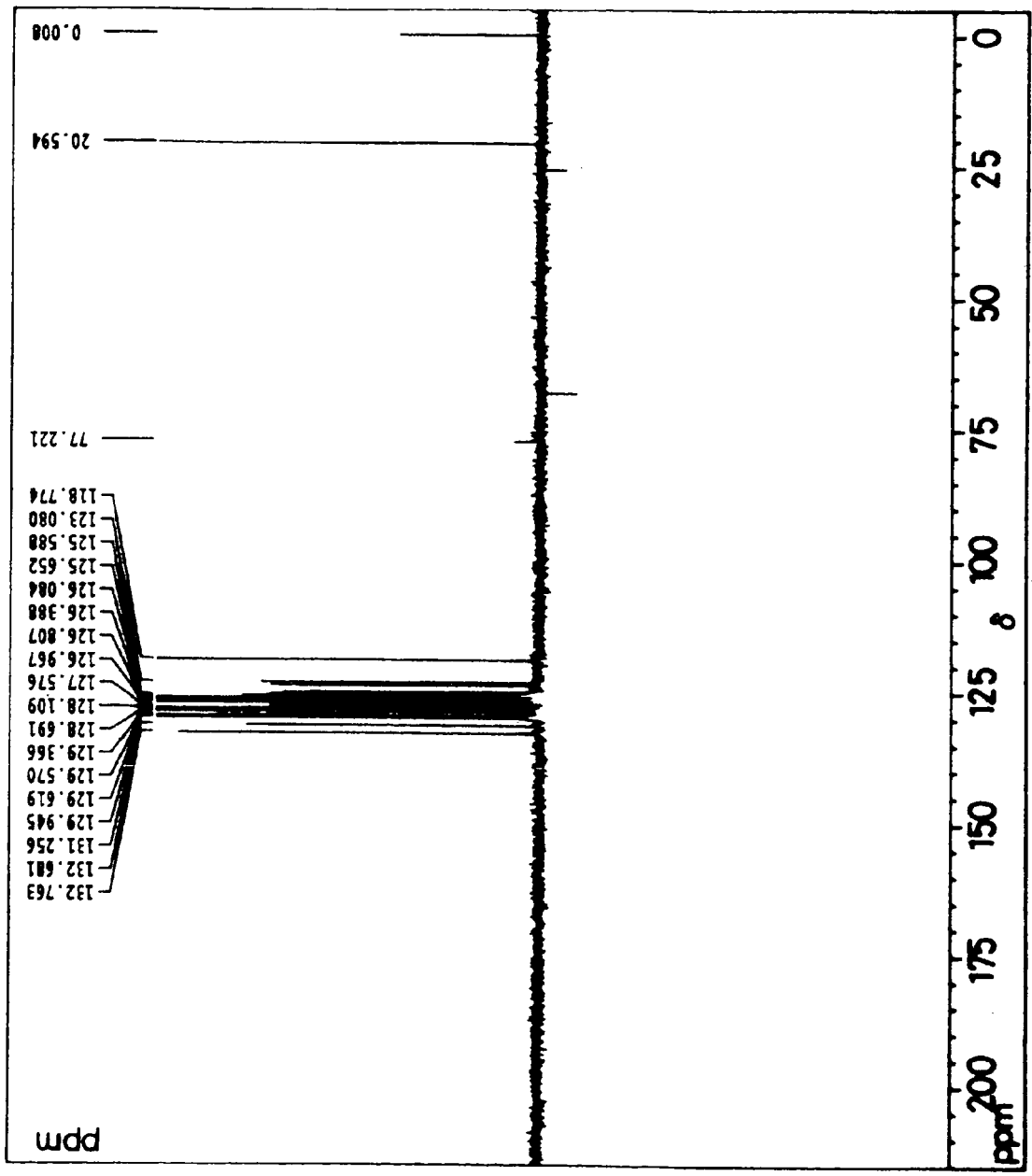
FIG. 9 is a $^{13}$C-NMR spectrum in DEPT135 measurement of the product in Production Example 1-3.
Figure 10:
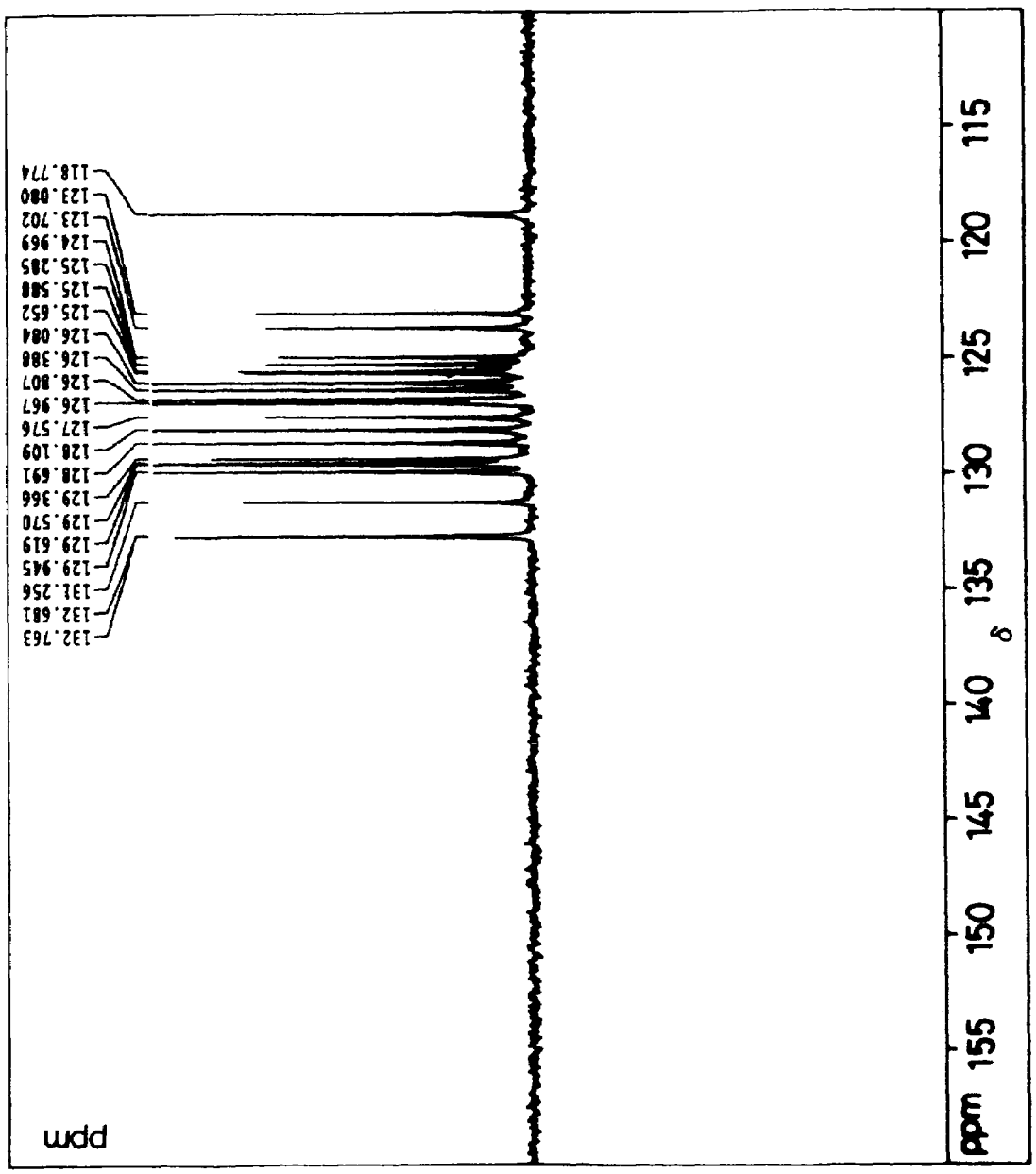
FIG. 10 is an enlarged view of the spectrum of FIG. 9 in the range of from 110 ppm to 160 ppm.

The nuclear magnetic resonance (NMR) spectrum of the crystal in heavy chloroform (chemical formula: $CDCl_3$) was measured, and this spectrum supports the structure of the enamine compound, Compound No. 1. FIG. 5 is the $^1$H-NMR spectrum of the product in this Production Example 1-3, and FIG. 6 is an enlarged view of the spectrum of FIG. 5 in the range of from 6 ppm to 9 ppm. FIG. 7 is the $^{13}$C-NMR spectrum in ordinary measurement of the product in Production Example 1-3, and FIG. 8 is an enlarged view of the spectrum of FIG. 7 in the range of from 110 ppm to 160 ppm. FIG. 9 is the $^{13}$C-NMR spectrum in DEPT135 measurement of the product in Production Example 1-3, and FIG. 10 is an enlarged view of the spectrum of FIG. 9 in the range of from 110 ppm to 160 ppm. In FIG. 5 to FIG. 10, the horizontal axis indicates the chemical shift δ (ppm) of the compound analyzed. In FIG. 5 and FIG. 6, the data written between the signals and the horizontal axis are relative integral values of the signals based on the integral value, 3, of the signal indicated by the reference numeral 500 in FIG. 5.

The data of LC-MS and the NMR spectrometry confirm that the crystal obtained herein is the enamine compound, Compound No. 1 (yield: 94%). In addition, the data of LC-MS further confirm that the purity of the enamine compound, Compound No. 1 obtained herein is 99.8%.

As in the above, the Wittig-Horner reaction of the enamine-aldehyde intermediate represented by formula (11) and the Wittig reagent, diethyl cinnamylphosphonate represented by formula (12) gives the enamine compound, Compound No. 1 shown in Table 1.

Production Example 2

Production of Compound No. 61

In the same manner as in Production Example 1 except that 4.9 g (1.0 equivalent) of N-(p-methoxyphenyl)-α-naphthylamine was used in place of 23.3 g (1.0 equivalent) of N-(p-tolyl)-α-naphthylamine represented by formula (8), an enamine intermediate was produced (yield: 94%) through dehydrating condensation and an enamine-aldehyde intermediate was produced (yield: 85%) through Vilsmeier reaction, and this was further subjected to Wittig-Horner reaction to obtain 7.9 g of an yellow powdery compound. The equivalent relationship between the reagent and the substrate used in each reaction was the same as that in Production Example 1.

Thus obtained, the compound was analyzed through LC-MS, which gave a peak at 556.7 corresponding to the molecular ion [M+H]+ of the intended enamine compound, Compound No. 61 in Table 9 (calculated molecular weight: 555.26) with a proton added thereto.

Figure 11:
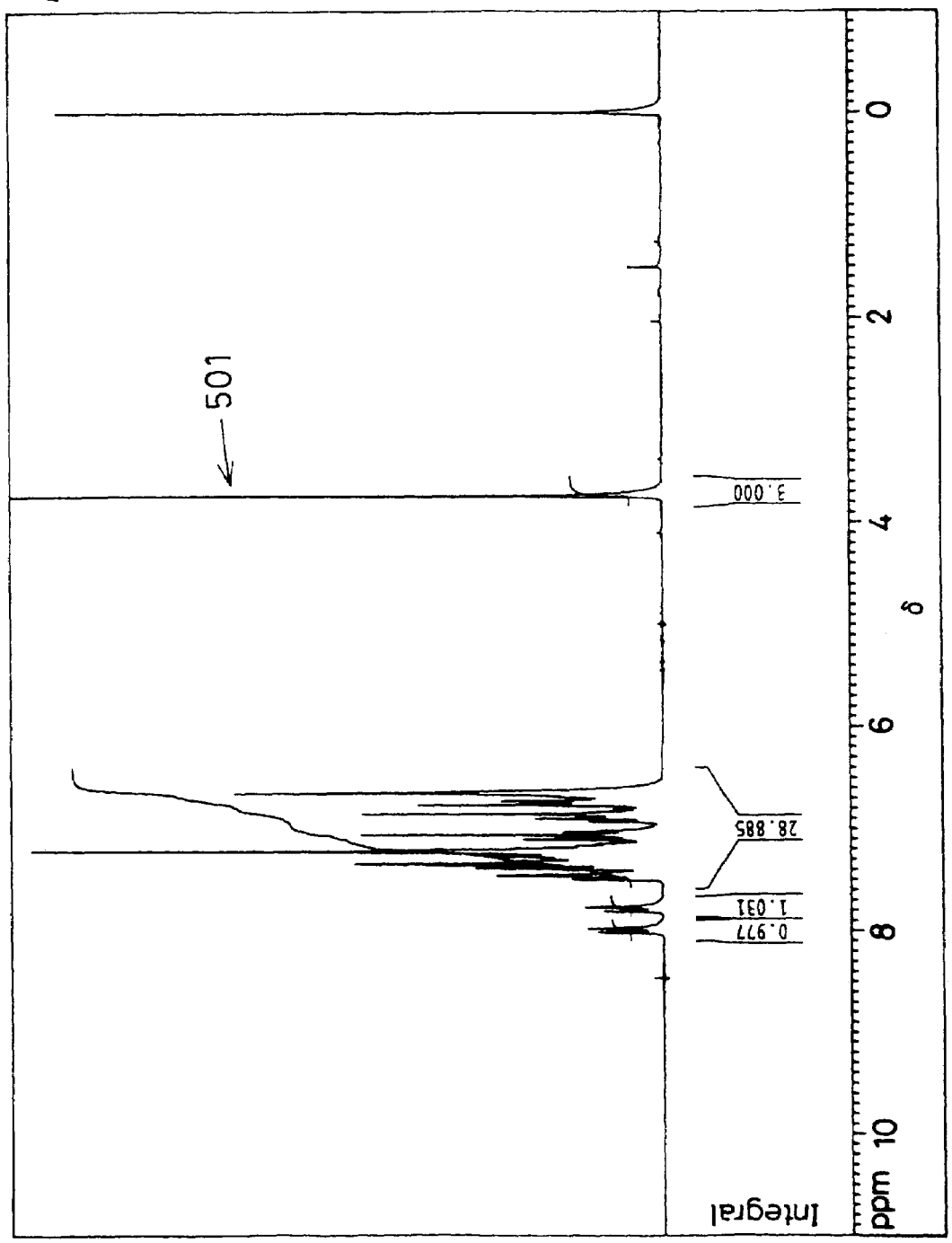
FIG. 11 is a $^1$H-NMR spectrum of the product in Production Example 2.
Figure 12:
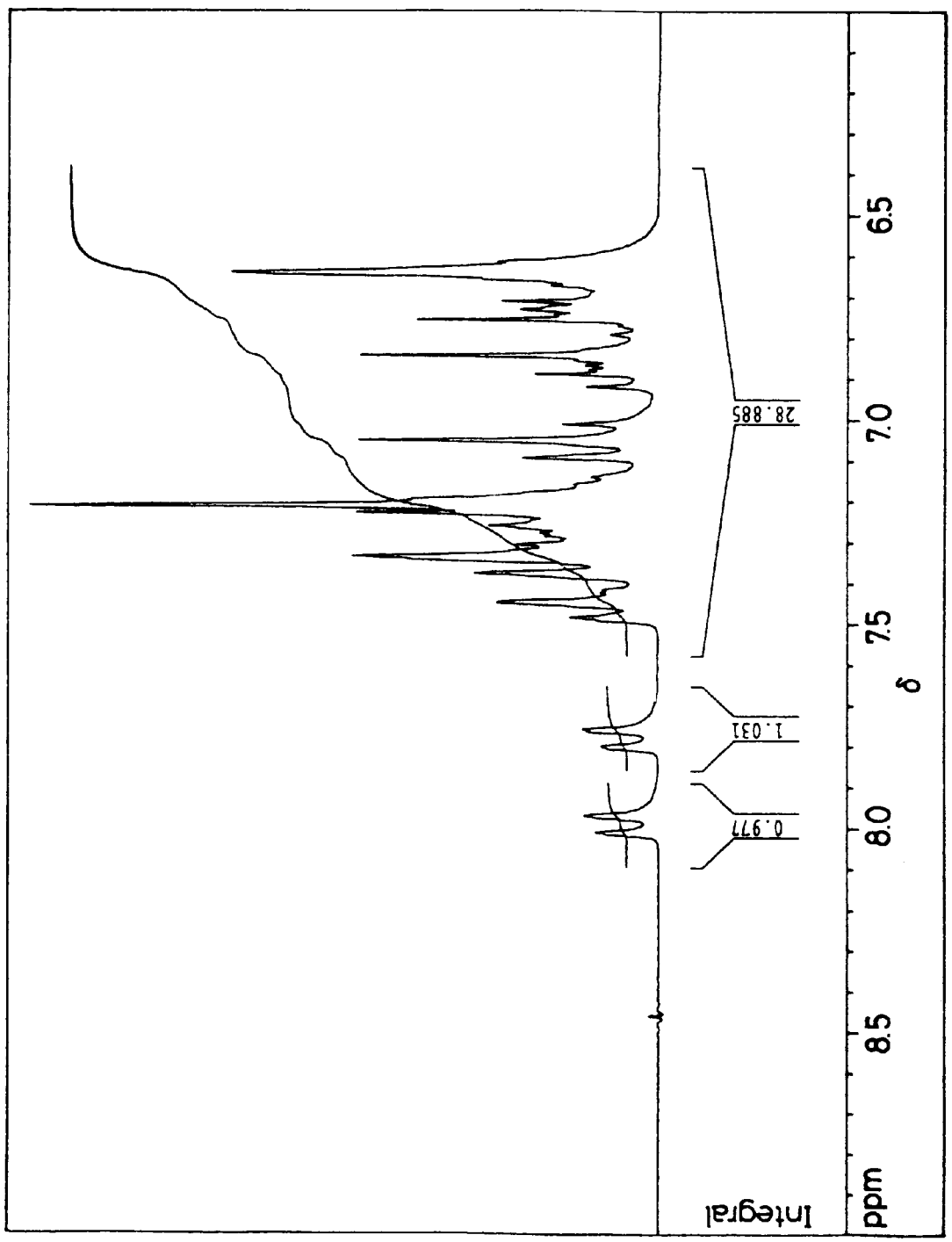
FIG. 12 is an enlarged view of the spectrum of FIG. 11 in the range of from 6 ppm to 9 ppm.
Figure 13:
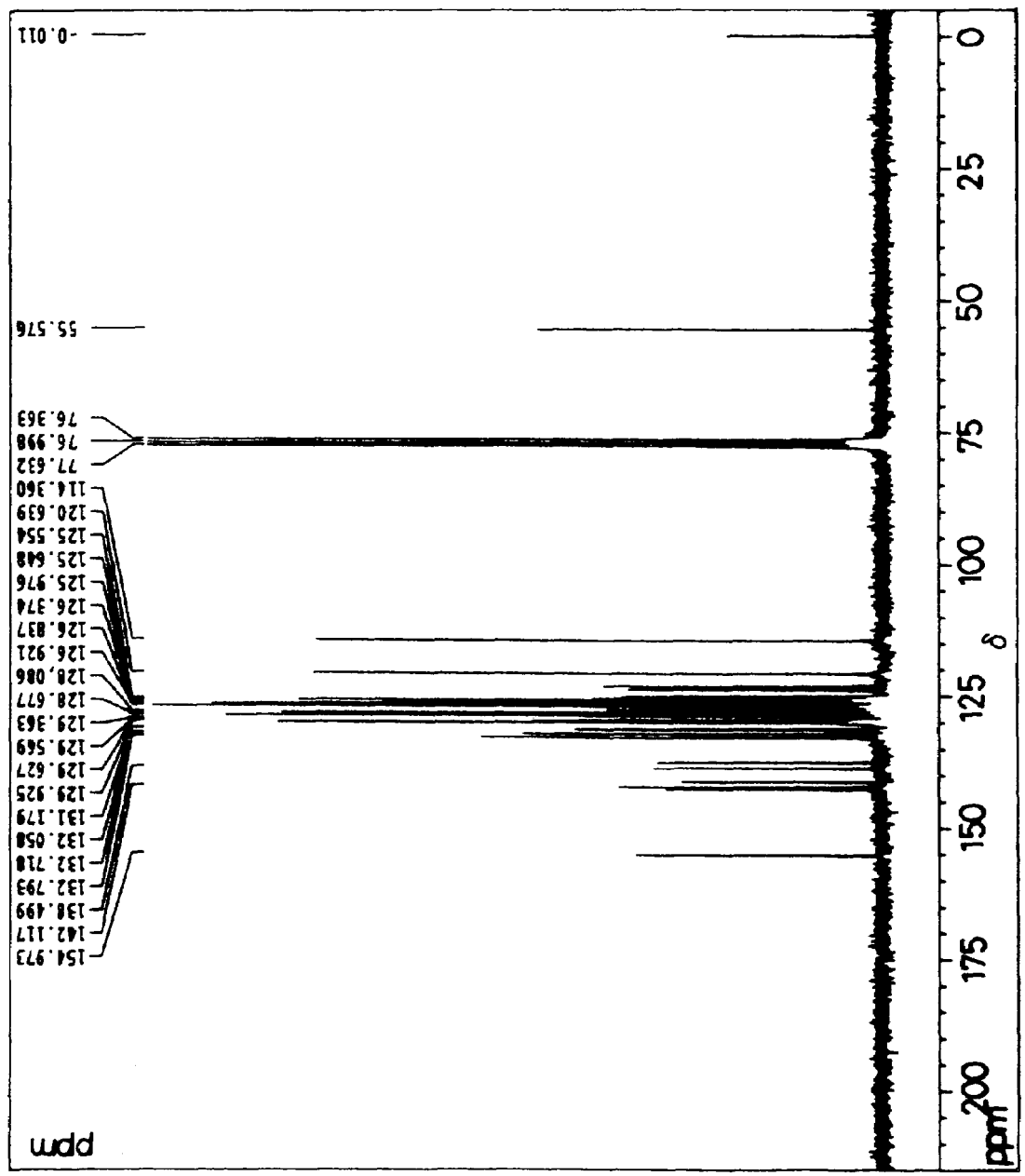
FIG. 13 is a $^{13}$C-NMR spectrum in ordinary measurement of the product in Production Example 2.
Figure 14:
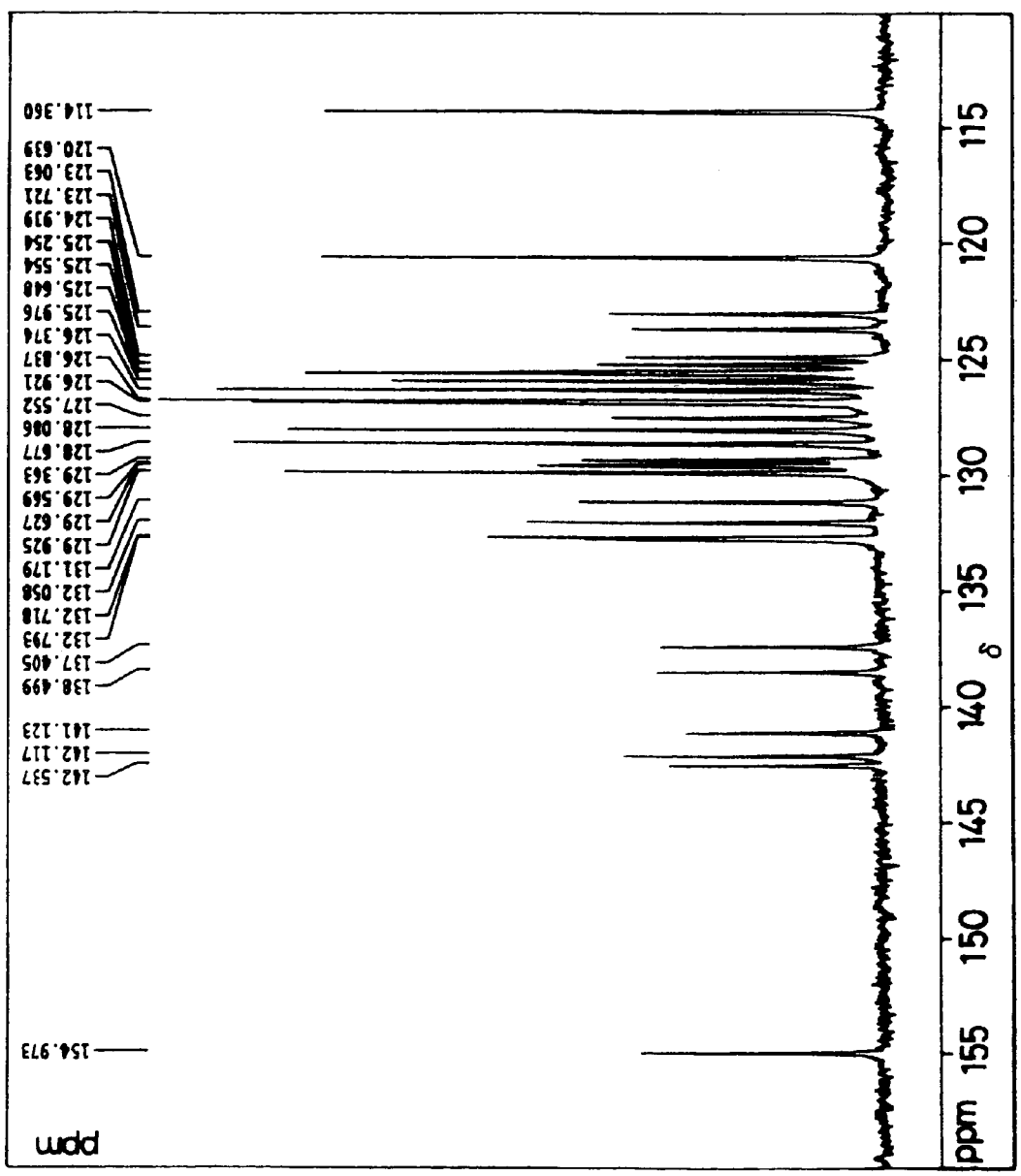
FIG. 14 is an enlarged view of the spectrum of FIG. 13 in the range of from 110 ppm to 160 ppm.
Figure 15:
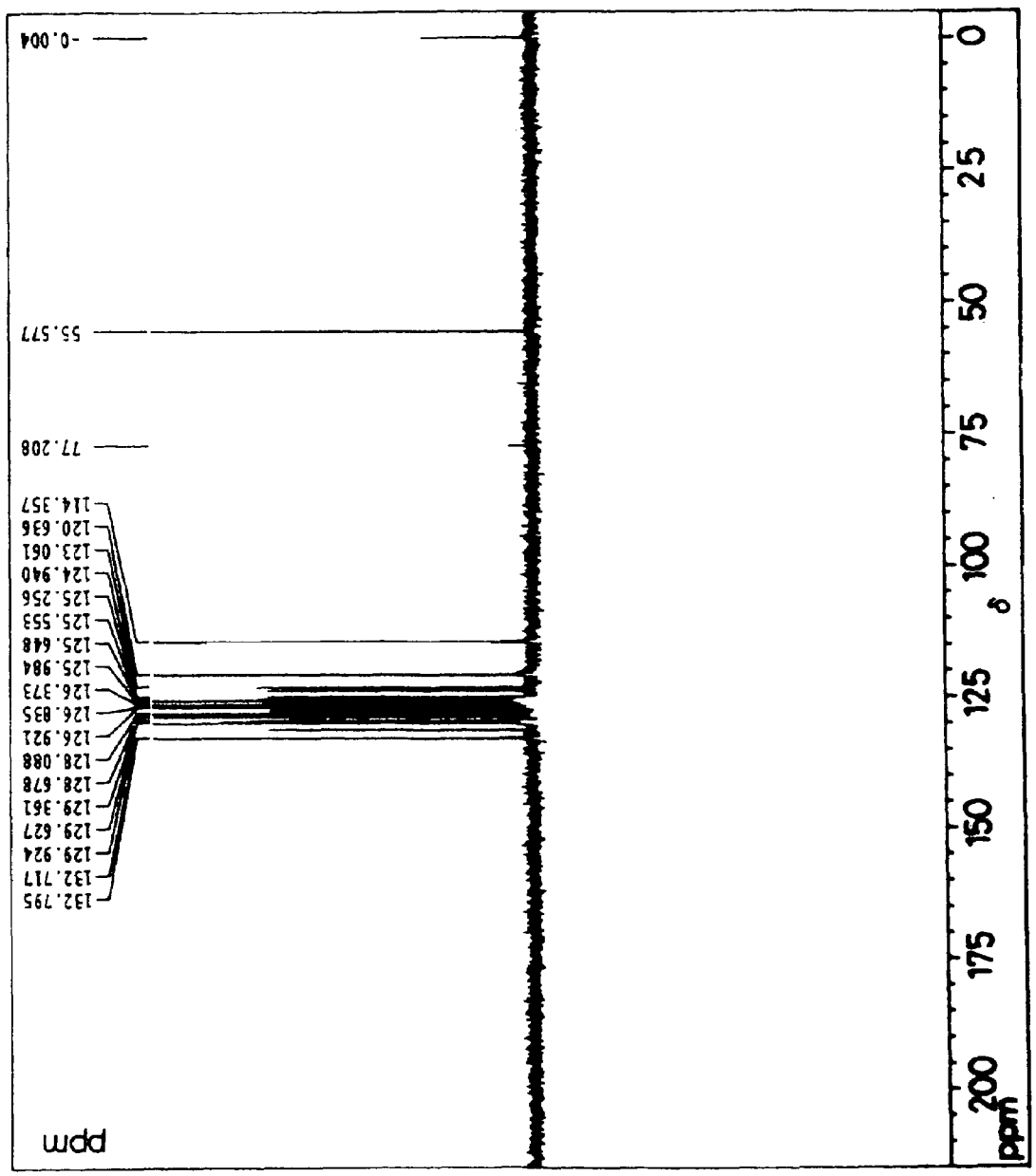
FIG. 15 is a $^{13}$C-NMR spectrum in DEPT135 measurement of the product in Production Example 2.
Figure 16:
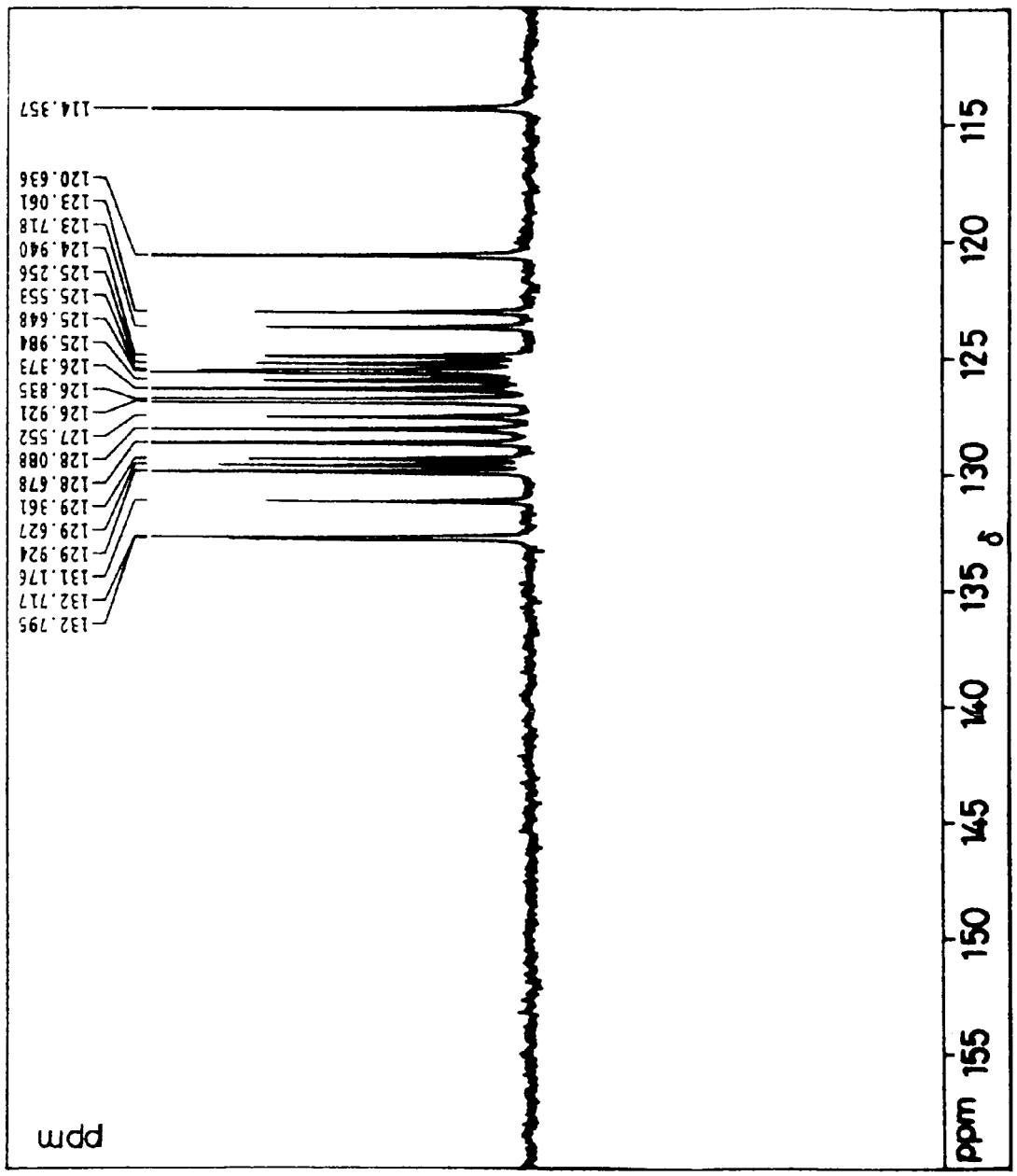
FIG. 16 is an enlarged view of the spectrum of FIG. 15 in the range of from 110 ppm to 160 ppm.

The NMR spectrum of the compound in heavy chloroform ($CDCl_3$) was measured, and this spectrum supports the structure of the enamine compound, Compound No. 61. FIG. 11 is the $^1$H-NMR spectrum of the product in this Production Example 2, and FIG. 12 is an enlarged view of the spectrum of FIG. 11 in the range of from 6 ppm to 9 ppm. FIG. 13 is the $^{13}$C-NMR spectrum in ordinary measurement of the product in Production Example 2, and FIG. 14 is an enlarged view of the spectrum of FIG. 13 in the range of from 110 ppm to 160 ppm. FIG. 15 is the $^{13}$C-NMR spectrum in DEPT135 measurement of the product in Production Example 2, and FIG. 16 is an enlarged view of the spectrum of FIG. 15 in the range of from 110 ppm to 160 ppm. In FIG. 11 to FIG. 16, the horizontal axis indicates the chemical shift δ (ppm) of the compound analyzed. In FIG. 11 and FIG. 12, the data written between the signals and the horizontal axis are relative integral values of the signals based on the integral value, 3, of the signal indicated by the reference numeral 501.

The data of LC-MS and the NMR spectrometry confirm that the compound obtained herein is the enamine compound, Compound No. 61 (yield: 92%). In addition, the data of LC-MS further confirm that the purity of the enamine compound, Compound No. 61 obtained herein is 99.0%.

As in the above, the three-stage reaction process that comprises dehydrating condensation, Vilsmeier reaction and Wittig-Horner reaction gives the enamine compound, Compound No. 61 shown in Table 9, and the overall three-stage yield of the product was 73.5%.

Production Example 3

Production of Compound No. 46

2.0 g (1.0 equivalent) of the enamine-aldehyde intermediate represented by formula (11) obtained in Production Example 1-2, and 1.53 g (1.2 equivalents) of a Wittig reagent of the following structural formula (13) were dissolved in 15 ml of anhydrous DMF, and 0.71 g (1.25 equivalents) of potassium t-butoxide was gradually added to the solution at room temperature, then heated up to 50° C., and stirred for 5 hours while kept heated at 50° C. The reaction mixture was left cooled, and poured into excess methanol. The deposit was collected, and dissolved in toluene to prepare a toluene solution thereof. The toluene solution was transferred into a separating funnel and washed with water, and the organic layer was taken out. Thus taken out, the organic layer was dried with magnesium sulfate. Solid matter was removed from the thus-dried organic layer, which was then concentrated and subjected to silica gel column chromatography to obtain 2.37 g of an yellow crystal.

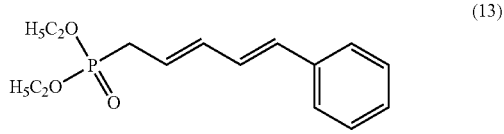

(13)

Thus obtained, the crystal was analyzed through LC-MS, which gave a peak at 566.4 corresponding to the molecular ion [M+H]$^+$ of the intended enamine compound, Compound No. 46 in Table 7 (calculated molecular weight: 565.28) with a proton added thereto. This confirms that the crystal obtained herein is the enamine compound, Compound No. 46 (yield: 92%). In addition, the data of LC-MS further confirm that the purity of the enamine compound, Compound No. 46 is 99.8%.

As in the above, the Wittig-Horner reaction of the enamine-aldehyde intermediate represented by formula (11) and the Wittig reagent represented by formula (13) gives the enamine compound, Compound No. 46 shown in Table 7.

Comparative Production Example 1

Production of Compound of Structural Formula (14)

2.0 g (1.0 equivalent) of the enamine-aldehyde intermediate represented by formula (11) obtained in Production Example 1-2 was dissolved in 15 ml of anhydrous THF, and 5.23 ml (1.15 equivalents) of a THF solution of a Grignard reagent, allylmagnesium bromide prepared from allyl bromide and metal magnesium (molar concentration: 1.0 mol/liter) was gradually added to the solution at 0° C. This was stirred at 0° C. for 0.5 hour, and then checked for the reaction progress through thin-layer chromatography, in which no definite reaction product was confirmed but some different products were found. This was post-processed, extracted and concentrated in an ordinary manner. Then, the reaction mixture was isolated and purified through silica gel column chromatography.

However, the intended compound of the following structural formula (14) could not be obtained.

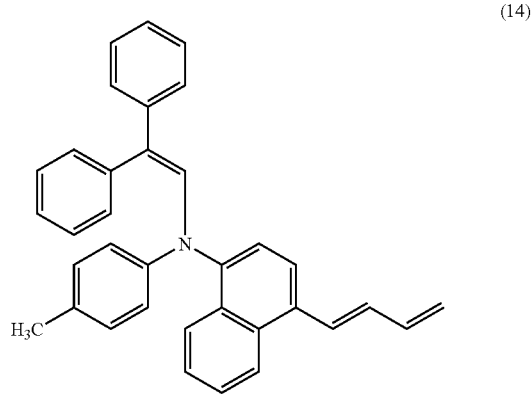

(14)

Example

Example 1

9 parts by weight of dendritic titanium oxide applied with a surface treatment with aluminum oxide (chemical formula: $Al_2O_3$) and zirconium dioxide (chemical formula: $ZrO_2$) (manufactured by Ishihara Sangyo Co.: TTO-D-1), and 9 parts by weight of copolymerized nylon resin (manufactured by Toray Co.: Amilan CM8000) were added to a mixed solvent of 41 parts by weight of 1,3-dioxolane and 41 parts by weight of methanol, and they were dispersed for 12 hours by a paint shaker to prepare a coating solution for intermediate layer. An aluminum substrate of 0.2 mm thickness as a conductive substrate 11 was coated with the coating solution for intermediate layer by a baker applicator, it was then dried to form an intermediate layer 18 of 1 μm film thickness.

After adding 2 parts by weight of an azo compound represented by the following structural formula (15) as a charge generating substance 12 into a resin solution obtained by dissolving 1 part by weight of polyvinyl butyral resin (manufactured by Sekisui Chemical Industry Co. S-LEC BX-1) into 97 parts by weight of THF, they were dispersed by a paint shaker for 10 hours to prepare a coating solution for charge generating layer. The previously formed intermediate layer 18 was coated with the obtained coating solution for charge generating layer by a baker applicator, it was then dried to form a charge generating layer 15 of 0.3 μm film thickness.

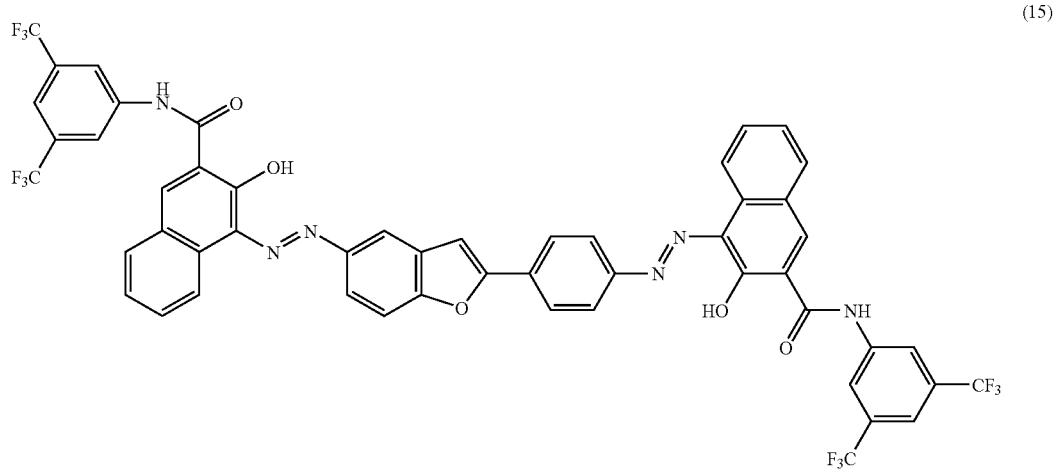

(15)

Then, 10 parts by weight of an enamine compound of Exemplified Compound No. 1 shown in Table 1 as a charge transporting substance 13, 14 parts by weight of polycarbonate resin (manufactured by Mitsubishi Gas Chemical Co., Inc.: Z200) as a binder resin 17, and 1 part by weight (about 4% based on the photosensitive layer) of a hindered phenol compound of Exemplified Compound HP-1 shown in Table 33 as an antioxidant were dissolved in 80 parts by weight of THF, to prepare a coating solution for charge transporting layer. Then, after coating the previously formed charge generating layer 15 with the obtained coating solution for charge transporting layer by a baker applicator, it was dried to form a charge transporting layer 16 of 18 μm thickness.

As described above, a layered type electrophotographic photoreceptor having a layer structure as shown in FIG. 2 satisfying the constituent factors of the invention were formed.

Examples 2 to 6

Five kinds of electrophotographic photoreceptors satisfying the constituent factors of the invention were formed in the same manner as in Example 1 except for using Exemplified Compound No. 3 shown in Table 1, Exemplified Compound No. 61 shown in Table 9, Exemplified Compound No. 106 shown in Table 16, Exemplified Compound No. 146 shown in Table 21 or Exemplified Compound No. 177 shown in Table 26 instead of Exemplified Compound No. 1 as the charge transporting substance 13 in Example 1.

Comparative Example 1

An electrophotographic photoreceptor not satisfying the constituent factors of the invention was formed in the same manner as in Example 1 except for using Comparative Compound A represented by the following structural formula (16) instead of Exemplified Compound No. 1 as the charge transporting substance 13.

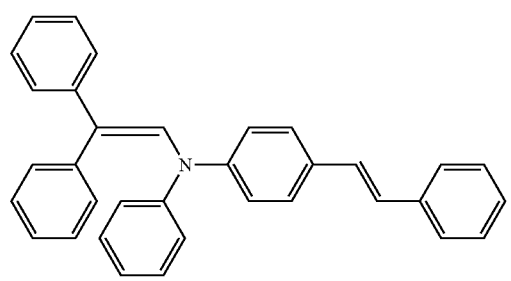

(16)

Comparative Example 2

An electrophotographic photoreceptor not satisfying the constituent factors of the invention was formed in the same manner as in Example 1 except for using Comparative Compound B represented by the following structural formula (17) instead of Exemplified Compound No. 1 as the charge transporting substance 13 in Example 1.

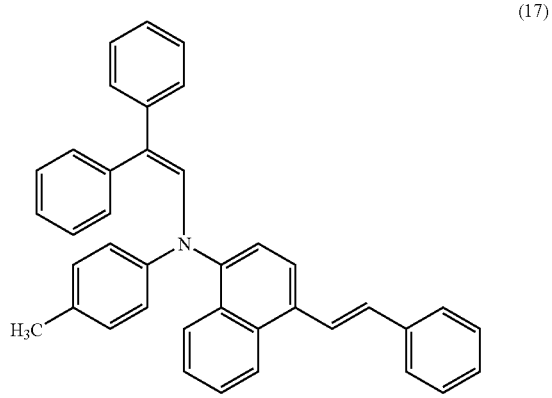

(17)

Comparative Example 3

An electrophotographic photoreceptor not satisfying the constituent factors of the invention was formed in the same manner as in Example 1 except for using Comparative Compound C represented by the following structural formula (18) instead of Exemplified Compound No. 1 as the charge transporting substance 13 in Example 1.

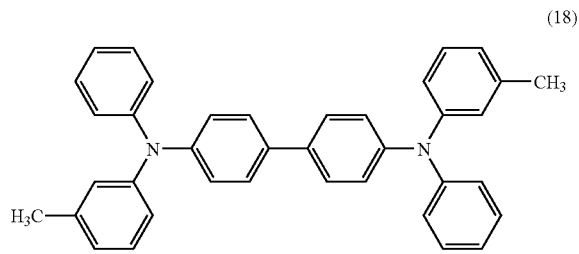

(18)

Example 7

In the same manner as in Example 1, an intermediate layer 18 of 1 μm thickness was formed on an aluminum substrate of 0.2 mm thickness as a conductive substrate 11.

Then, 1 part by weight of an azo compound represented by the structural formula (15) as the charge generating substance 12, 12 parts by weight of polycarbonate resin (manufactured by Mitsubishi Gas Chemical Co., Inc.: Z-400) as a binder resin 17, 10 parts by weight of an enamine compound of Exemplified Compound No. 1 shown in Table 1 as the charge transporting substance 13, 0.5 part by weight (about 2% by weight based on the photosensitive layer) of a hindered phenol compound of Exemplified Compound HP-1 shown in Table 33 as an antioxidant, 5 parts by weight of 3,5-dimethyl-3',5'-di-t-butyl diphenoquinone, and 65 parts by weight of THF were dispersed in a ball mill for 12 hours to form a coating solution for photosensitive layer. The previously formed intermediate layer 18 was coated with the obtained coating solution for photosensitive layer by a baker applicator, it was then dried by hot blow at 110° C. for one hour to form a photosensitive layer 140 of 20 μm thickness.

As described above, a single layer type electrophotographic photoreceptor having a layer structure shown in FIG. 3 satisfying constituent factors of the invention was formed.

Example 8

An electrophotographic photoreceptor satisfying the constituent factors of the invention was formed in the same manner as in Example 1 except for using X-type non-metal phthalocyanine instead of an azo compound represented by the structure formula (15) as the charge generating substance 12 in Example 1.

Example 9 to 13

An electrophotographic photoreceptor satisfying the constituent factors of the invention was formed in the same manner as in Example 1 except for using X-type non-metal phthalocyanine instead of the azo compound represented by the structure formula (15) as the charge generating substance 12, and using Exemplified Compound No. 3 shown in Table 1, Exemplified Compound No. 61 shown in Table 9, Exemplified Compound No. 106 shown in Table 16, Exemplified Compound No. 146 shown in Table 21, or Exemplified Compound No. 177 shown in Table 26 instead of the Exemplified Compound No. 1 as the charge transporting substance 13 in Example 1.

Comparative Examples 4 to 6

Three kinds of electrophotographic photoreceptors not satisfying the constituent factors of the invention were formed in the same manner as in Example 1 except for using X-type non-metal phthalocyanine instead of the azo compound represented by the structural formula (15) as the charge generating substance 12, and using Comparative Compound A represented by the structural formula (16), Comparative Compound B represented by the structural formula (17) or Comparative Compound C represented by the structural formula (18) instead of Exemplified Compound No. 1 as the charge transporting substance 13 in Example 1.

Comparative Example 7

An electrophotographic photoreceptor not satisfying the constituent factors of the invention was formed in the same manner as in Example 1 except for using X-type non-metal phthalocyanine instead of the azo compound represented by the structural formula (15) as the charge generating substance 12, and using Comparative Compound D represented by the structural formula (19) instead of Exemplified Compound No. 1 as the charge transporting substance 13 in Example 1.

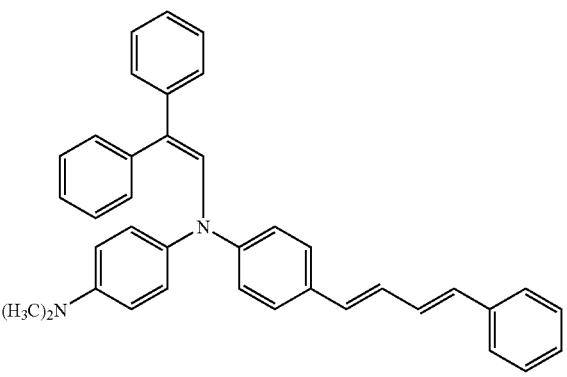

(19)

Comparative Example 8

An electrophotographic photoreceptor not satisfying the constituent factors of the invention was formed in the same manner as in Example 1 except for using X-type non-metal phthalocyanine instead of the azo compound represented by the structural formula (15) as the charge generating substance 12, and using Comparative Compound E represented by the structural formula (20) instead of Exemplified Compound No. 1 as the charge transporting substance 13 in Example 1.

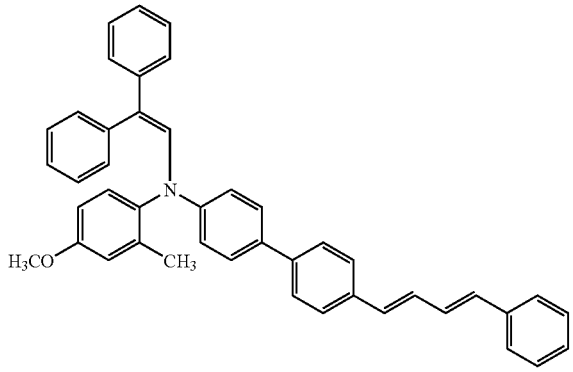
(20)

<Evaluation 1>

For each of the electrophotographic photoreceptors manufactured in Examples 1 to 13 and Comparative Examples 1 to 8, initial characteristics and characteristics after repetitive use were evaluated by using an electrostatic copy paper testing apparatus (manufactured by Kawaguchi Denki Seisakusho Co.: EPA-8200). The evaluation was conducted in such a manner as described below under an N/N (Normal Temperature/Normal Humidity) circumstance at a temperature of 22° C. and at a relative humidity of 65% (22° C./65% RH), and under an L/L (Low temperature/Low Humidity) circumstance at a temperature of 5° C. and at a relative humidity of 20% (5° C./20% RH).

The surface of the photoreceptor was charged by applying a voltage at negative (−)5 kV to a photoreceptor and the surface potential on the photoreceptor in this case was measured as a charge potential $V_0$ (V). However, in a case of the single layered type photoreceptor in Example 7, the surface of the photoreceptor was charged by applying a voltage at positive (+) 5 kV.

Then, exposure was applied to the charged surface of the photoreceptor, and the energy required for decaying the surface potential on the photoreceptor to one-half of the charge potential $V_0$ was measured as a half-decay exposure amount $E_{1/2}$ (μJ/cm$^2$). Further, the surface potential on the photoreceptor at the time with lapse of 10 sec from the start of exposure was measured as a residual potential Vr (V). For the exposure, a white light at an exposure energy of 1 μW/cm$^2$ was used in the case of Examples 1 to 7 and Comparative Examples 1 to 3 using the azo compound represented by the structural formula (15) as the charge generating substance 12, and a light at a wavelength of 780 nm and at an exposure energy of 1 μm/cm$^2$ obtained by spectralyzing by a monochromer was used in the case of Examples 8 to 13 and Comparative Examples 4 to 8 using X-type non-metal phthalocyanine as the charge generating substance 12. The results of the measurements were used as the results of measurements in the initial state.

After repeating the operation of charging and exposure for 5000 times as one cycle, the charge potential $V_0$, the half-decay exposure amount $E_{1/2}$, and the residual potential $V_r$ were measured in the same manner as in the evaluation for initial characteristics. The results of the measurements were used as the results of measurements after repetitive use.

Table 56 shows the results of the measurements for the initial characteristics and the characteristics after repetitive use.

TABLE 56

| | Charge generating substance | Charge transporting substance | N/N: 22° C./65% RH Initial state | | |
|---|---|---|---|---|---|
| | | | $E_{1/2}$ (μJ/cm$^2$) | $V_0$(V) | Vr(V) |
| Example 1 | Azo Compound (15) | Exemplified Compound 1 | 0.16 | −584 | −10 |
| Example 2 | Azo Compound (15) | Exemplified Compound 3 | 0.15 | −586 | −13 |
| Example 3 | Azo Compound (15) | Exemplified Compound 61 | 0.14 | −583 | −14 |
| Example 4 | Azo Compound (15) | Exemplified Compound 106 | 0.14 | −586 | −13 |
| Example 5 | Azo Compound (15) | Exemplified Compound 146 | 0.15 | −581 | −15 |
| Example 6 | Azo Compound (15) | Exemplified Compound 177 | 0.16 | −585 | −15 |
| Comp. Example 1 | Azo Compound (15) | Comparative Compound A | 0.20 | −578 | −35 |
| Comp. Example 2 | Azo Compound (15) | Comparative Compound B | 0.21 | −575 | −38 |
| Comp. Example 3 | Azo Compound (15) | Comparative Compound C | 0.21 | −591 | −42 |
| Example. 7 | Azo Compound (15) | Exemplified Compound 1 | 0.24 | 559 | 19 |
| Example. 8 | X-type non-metal phthalocyanine | Exemplified Compound 1 | 0.11 | −585 | −10 |
| Example. 9 | X-type non-metal phthalocyanine | Exemplified Compound 3 | 0.12 | −581 | −12 |
| Example. 10 | X-type non-metal phthalocyanine | Exemplified Compound 61 | 0.10 | −584 | −9 |
| Example 11 | X-type non-metal phthalocyanine | Exemplified Compound 106 | 0.10 | −586 | −9 |
| Example 12 | X-type non-metal phthalocyanine | Exemplified Compound 146 | 0.13 | −583 | −11 |
| Example 13 | X-type non-metal phthalocyanine | Exemplified Compound 177 | 0.13 | −581 | −13 |
| Comp. Example 4 | X-type non-metal phthalocyanine | Comparative Compound A | 0.15 | −586 | −25 |
| Comp. Example 5 | X-type non-metal phthalocyanine | Comparative Compound B | 0.15 | −585 | −28 |
| Comp. Example 6 | X-type non-metal phthalocyanine | Comparative Compound C | 0.15 | −581 | −30 |
| Comp. Example 7 | X-type non-metal phthalocyanine | Comparative Compound D | 0.13 | −585 | −98 |
| Comp. Example 8 | X-type non-metal phthalocyanine | Comparative Compound E | 0.15 | −587 | −22 |

TABLE 56-continued

|  | N/N: 22° C./65% RH | | | L/L: 5° C./20% RH | | | | | |
| --- | --- | --- | --- | --- | --- | --- | --- | --- | --- |
|  | After repetitive use | | | Initial state | | | After repetitive use | | |
|  | $E_{1/2}$ ($\mu J/cm^2$) | $V_0(V)$ | $Vr(V)$ | $E_{1/2}$ ($\mu J/cm^2$) | $V_0(V)$ | $Vr(V)$ | $E_{1/2}$ ($\mu J/cm^2$) | $V_0(V)$ | $Vr(V)$ |
| Example 1 | 0.18 | −574 | −15 | 0.18 | −586 | −15 | 0.19 | −576 | −18 |
| Example 2 | 0.16 | −576 | −17 | 0.16 | −587 | −13 | 0.18 | −579 | −19 |
| Example 3 | 0.15 | −578 | −18 | 0.16 | −585 | −18 | 0.18 | −573 | −20 |
| Example 4 | 0.16 | −577 | −15 | 0.16 | −584 | −16 | 0.17 | −576 | −19 |
| Example 5 | 0.16 | −575 | −19 | 0.17 | −581 | −16 | 0.20 | −575 | −19 |
| Example 6 | 0.19 | −573 | −18 | 0.18 | −583 | −18 | 0.22 | −572 | −23 |
| Comp. Example 1 | 0.22 | −576 | −36 | 0.42 | −579 | −50 | 0.45 | −571 | −51 |
| Comp. Example 2 | 0.24 | −577 | −42 | 0.44 | −578 | −55 | 0.48 | −577 | −59 |
| Comp. Example 3 | 0.25 | −589 | −54 | 0.45 | −581 | −55 | 0.51 | −579 | −65 |
| Example. 7 | 0.26 | 542 | 25 | 0.26 | 551 | 25 | 0.29 | 540 | 30 |
| Example. 8 | 0.12 | −573 | −13 | 0.13 | −583 | −12 | 0.15 | −573 | −15 |
| Example. 9 | 0.12 | −574 | −15 | 0.15 | −584 | −15 | 0.18 | −576 | −18 |
| Example. 10 | 0.11 | −573 | −13 | 0.12 | −587 | −12 | 0.14 | −575 | −15 |
| Example 11 | 0.12 | −574 | −12 | 0.11 | −586 | −10 | 0.13 | −572 | −13 |
| Example 12 | 0.15 | −574 | −15 | 0.16 | −586 | −13 | 0.18 | −574 | −16 |
| Example 13 | 0.14 | −575 | −18 | 0.17 | −584 | −14 | 0.19 | −573 | −18 |
| Comp. Example 4 | 0.17 | −576 | −27 | 0.36 | −580 | −45 | 0.38 | −578 | −46 |
| Comp. Example 5 | 0.19 | −575 | −35 | 0.38 | −582 | −48 | 0.42 | −575 | −55 |
| Comp. Example 6 | 0.19 | −575 | −40 | 0.38 | −579 | −50 | 0.45 | −570 | −59 |
| Comp. Example 7 | 0.18 | −571 | −115 | 0.21 | −580 | −115 | 0.23 | −572 | −123 |
| Comp. Example 8 | 0.18 | −574 | −31 | 0.35 | −582 | −49 | 0.44 | −572 | −60 |

It was found from the Table 56 that all of the photoreceptors in Examples 1 to 13 and Comparative Examples 1 to 8 each containing the antioxidant in the photosensitive layer had less fatigue degradation upon repetitive use showing less difference between the result of measurement in the initial state and the result of measurement after repetitive use.

Further, it was found that among photoreceptors of Examples 1 to 13 and Comparative Examples 1 to 8, the photoreceptors of Examples 1 to 13 using the enamine compound represented by the general formula (1) for the charge transporting substance 13 had higher sensitivity showing less half-decay exposure amount $E_{1/2}$ and were more excellent in the light responsivity showing smaller absolute value for residual potential Vr as compared with the photoreceptors of Comparative Examples 1 to 8 using Comparative Compounds A, B, C, D or E for the charge transporting substance 13. Further, it was found that the photoreceptors of Examples 1 to 13 was more excellent in the stability of characteristics relative to the change of circumstances showing less difference between the result of measurement under N/N circumstance and the result of measurement under an L/L circumstance, and caused no deterioration for the characteristics even under the L/L circumstance, whereas the photoreceptors of Comparative Examples 1 to 8 show more difference between the result of measurement under the N/N circumstance and the result of measurement under the L/L circumstance, and showed larger deterioration for the characteristics under the L/L circumstance.

Example 14

21 parts by weight of titanium oxide (manufactured by Ishihara Sangyo Co.: TTO55A) and 39 parts by weight of copolymerized nylon resin (manufactured by Toray Co.: Amilan CM8000) were added to a mixed solvent of 329 parts by weight of methanol and 611 parts by weight of 1,2-dichloroethane, and they were dispersed using a paint shaker for 8 hours to prepare a coating solution for intermediate layer. An aluminum substrate of 0.2 mm thickness, as a conductive substrate 11 was coated with the obtained coating solution for intermediate layer by a baker applicator, it was then dried to form an intermediate layer 18 of 1 μm thickness.

Then, after adding 2 parts by weight of Y-type oxotitanium phthalocyanine as a charge generating substance 12 to a resin solution obtained by dissolving 1 part by weight of polyvinyl butyral resin (manufactured by Sekisui Chemical Industry Co.: S-LEC BX-1) in 97 parts by weight of methyl ethyl ketone, they were dispersed by a paint shaker for 10 hours to prepare a coating solution for charge generating layer. The previously formed intermediate layer 18 was coated with the obtained coating solution for charge generating layer, it was then dried to form a charge generating layer 15 of 0.4 μm thickness.

Then, 10 parts by weight of the enamine compound of Exemplified Compound No. 61 shown in Table 9 as a charge transporting substance 13, 18 part by weight of polycarbonate resin (manufactured by Mitsubishi Gas Chemical Co., Inc.: PCZ400) as a binder resin 17, and 1.4 parts by weight (about 5% based on the photosensitive layer) of a hindered phenol compound of Exemplified Compound HP-1 shown in Table 33 as an antioxidant were dissolved in 100 parts by weight of THF, to prepare a coating solution for charge transporting layer. The previously formed charge generating layer 15 was coated with the obtained coating solution for charge transporting layer by a baker applicator, it was then dried to form a charge transporting layer 16 of 23 μm film thickness.

As described above, a stacked type electrophotographic photoreceptor having a layer structure shown in FIG. 2 satisfying the constituent factors of the invention was formed.

Examples 15 to 17

Three kinds of electrophotographic photoreceptors satisfying the constituent factors of the invention were formed in the same manner as in Example 14 except for using Exemplified Compound HP-9 shown in Table 33, Exemplified Compound P-7 shown in Table 40, or Exemplified Compound S-6 shown in Table 45 instead of the Exemplified Compound HP-1 as an antioxidant in Example 14.

Examples 18 to 20

Three kinds of electrophotographic photoreceptors satisfying the constituent factors of the invention were formed in the same manner as in Example 14 except for using Exemplified Compound HA-3 shown in Table 47, Exemplified Compound HA-10 shown in Table 48, or Exemplified Compound TZ-5 shown in Table 50 as a light stabilizer instead of Exemplified Compound HP-1 as an antioxidant in Example 14.

Example 21

An electrophotographic photoreceptor satisfying the constituent factors of the invention was formed in the same manner as in Example 14 except for using Exemplified Compound No. 3 shown in Table 1 instead of Exemplified Compound No. 61 as a charge transporting substance 13, and using Exemplified Compound HP-26 shown in Table 35 instead of Exemplified Compound HP-1 as antioxidant in Example 14.

Example 22

An electrophotographic photoreceptor satisfying the constituent factors of the invention was formed in the same manner as in Example 14 except for using Exemplified Compound No. 146 shown in Table 21 instead of Exemplified Compound No. 61 as a charge transporting substance 13, and using Exemplified Compound HA-10 shown in Table 48 as a light stabilizer instead of Exemplified compound HP-1 as an antioxidant in Example 14.

Example 23

After storing the coating solution for charge transporting layer obtained in Example 14 under a circumstance at a temperature of 40° C. in a dark place for one month, an electrophotographic photoreceptor satisfying the constituent factors of the invention was formed in the same manner as in Example 14 using the coating solution for charge transporting layer.

Example 24

An electrophotographic photoreceptor satisfying the constituent factors of the invention was formed in the same manner as in Example 14 except for changing the amount of the hindered phenol compound of Exemplified Compound HP-1 as an antioxidant to 5.4 parts (about 16% by weight based on the photosensitive layer) in Example 14.

Example 25

An electrophotographic photoreceptor satisfying the constituent factors of the invention was formed in the same manner as in Example 14 except for using 3.5 parts by weight (about 11% by weight based on the photosensitive layer) of the hindered amine compound of Exemplified Compound HA-3 shown in Table 47 as a light stabilizer instead of 1.4 parts by weight of the hindered phenol compound of Exemplified Compound HP-1 as an antioxidant in Example 14.

Comparative Example 9

An electrophotographic photoreceptor not satisfying the constituent factors of the invention was formed in the same manner as in Example 14 except for not using the hindered phenol compound of Exemplified Compound HP-1 as an antioxidant in Example 14.

Comparative Example 2

After storing the coating solution for charge transporting layer obtained in Comparative Example 1 under a circumstance at a temperature of 40° C. in a dark place for one month, an electrophotographic photoreceptor not satisfying the constituent factors of the invention was formed using the coating solution for charge transporting layer in the same manner as in Example 14.

<Evaluation 2>

For each of the electrophotographic photoreceptors manufactured in Examples 14 to 25 and Comparative Examples 9 and 10, initial characteristics and characteristics after repetitive use were evaluated by a so-called Dynamic method for conducting charge and measurement alternately while rotating a rotational disk on which a sample was placed using an electrostatic copy paper testing apparatus (manufactured by Kawaguchi Denki Seisakusho Co.: EPA-8200). The evaluation was conducted as described below under a high temperature and high humidity circumstance at a temperature of 35° C. and relative humidity of 85% (35° C./85% RH).

The surface of the photoreceptor was charged by applying a voltage at negative (−)600V to a photoreceptor while rotating a rotatable disk on which a sample was placed at a number of revolution of 1100 rpm/min. Then, exposure was applied to the charged surface of the photoreceptor by a monochromatic light having a wavelength of 780 nm at an exposure energy of 1 µW/cm$^2$, and the energy required for decaying the surface potential on the photoreceptor to one-half from negative (−)600V as the charge potential to negative (−)300V, was measured as a half-decay exposure amount $E_{1/2}$ (µJ/cm$^2$). Further, exposure was applied to the surface of the photoreceptor charged to negative (−)600V at an exposure amount of 2 µJ/cm$^2$, and the surface potential on the photoreceptor just after the exposure was measured as the residual potential $V_R$ (V). The results of the measurements were used as the results at initial state.

Then, after repeating the operation of the charging and exposure for 50000 times as one cycle, the half-decay exposure amount $E_{1/2}$ and the residual potential $V_R$ were measured in the same manner for those in the initial state. The results of the measurements were used as the results of measurement after repetitive use.

Table 57 shows the results of measurements in the initial state and after repetitive use.

TABLE 57

| | | Antioxidant · light stabilizer | | Initial stage | | After repetitive use | | |
|---|---|---|---|---|---|---|---|---|
| | Charge transporting substance | Exemplified Compound | Content (wt %) | $E_{1/2}(\mu J/cm2)$ | $V_n(V)$ | $E_{1/2}(\mu J/cm2)$ | $V_n(V)$ | Remarks |
| Example 14 | Exemplified Compound 61 | HP-1 | 5 | 0.15 | −15 | 0.17 | −21 | |
| Example 15 | Exemplified Compound 61 | HP-9 | 5 | 0.15 | −18 | 0.18 | −25 | |
| Example 16 | Exemplified Compound 61 | P-7 | 5 | 0.15 | −22 | 0.18 | −30 | |
| Example 17 | Exemplified Compound 61 | S-6 | 5 | 0.16 | −28 | 0.2 | −35 | |
| Example 18 | Exemplified Compound 61 | HA-3 | 5 | 0.14 | −15 | 0.17 | −22 | |
| Example 19 | Exemplified Compound 61 | HA-10 | 5 | 0.15 | −19 | 0.17 | −25 | |
| Example 20 | Exemplified Compound 61 | TZ-5 | 5 | 0.15 | −22 | 0.18 | −30 | |
| Example 21 | Exemplified Compound 3 | HP-26 | 5 | 0.17 | −25 | 0.21 | −31 | |
| Example 22 | Exemplified Compound 146 | HA-10 | 5 | 0.13 | −18 | 0.17 | −23 | |
| Example 23 | Exemplified Compound 61 | HP-1 | 5 | 0.16 | −16 | 0.18 | −23 | Manufactured after storing coating solution for one month |
| Example 24 | Exemplified Compound 61 | HP-1 | 16 | 0.16 | −52 | 0.18 | −58 | |
| Example 25 | Exemplified Compound 61 | HA-3 | 11 | 0.16 | −65 | 0.18 | −69 | |
| Comp. Example 9 | Exemplified Compound 61 | None | | 0.15 | −15 | 0.22 | −55 | |
| Comp. Example 10 | Exemplified Compound 61 | None | | 0.18 | −75 | 0.25 | −120 | Manufactured after storing coating solution for one month |

It was found from Table 57 that among the photoreceptors of Examples 14 to 25 and Comparative Examples 9 and 10 using the enamine compound represented by the general formula (1) for the charge transporting substance 13, the photoreceptors of Examples 14 to 25 containing an antioxidant or a light stabilizer in the photosensitive layer showed less fatigue degradation upon repetitive use, showing smaller difference between the result of the measurements in the initial state and the result of the measurements after repetitive use. On the contrary, it was found that the photoreceptors of Comparative Examples 9 and 10 containing none of the antioxidant or light stabilizer in the photosensitive layer showed a larger difference between the result of measurements in the initial state and the result of measurements after repetitive use and caused larger fatigue degradation upon repetitive use.

Further, it was found from the comparison between Example 14 and Example 23 that in a case where the antioxidant was added to the coating solution for charge transporting layer, photoreceptors having substantially identical characteristics were obtained even when photoreceptors were formed immediately after the preparation of the coating solution for charge transporting layer or when they were formed after lapse of a long time. On the contrary, in a case where the coating solution for charge transporting layer was incorporated with none of the antioxidant or light stabilizer as in the case of Comparative Example 9 and Comparative Example 10, the characteristics of the photoreceptor of Comparative Examples 9 prepared immediately after preparation of the coating liquid for charge transporting layer greatly differ from the characteristics of the photoreceptor of Comparative Example 10 prepared after lapse of a long time. In particular, the photoreceptor of Comparative Example 10 showed a larger absolute value of the residual potential $V_R$ as compared with that of the photoreceptor of Comparative Example 9 and caused degradation of the light responsivity. Based on the results described above, it can be seen that the stability of the coating liquid was improved by addition of the antioxidant.

Further, it was found from the comparison between Example 14 and Example 24 that, the photoreceptor of Example 24 having the content of the antioxidant in the photosensitive layer of exceeding 15% by weight was had somewhat larger absolute value of the residual potential $V_R$ and was somewhat poor in the light responsivity compared with the photoreceptor of Example 14 with the content of the antioxidant in the photosensitive layer within a range of from 0.1 to 15% by weight.

Further, it was found from the comparison between Example 18 and Example 25 that the photoreceptor of Example 25 having the content of the light stabilizer in the photosensitive layer of exceeding 10% by weight showed somewhat larger absolute value of the residual potential $V_R$ and was somewhat poor in the light responsivity compared with that of the photoreceptor of Example 18 having the content of the light stabilizer in the photosensitive layer within a range of from 0.1 to 10% by weight.

Example 26

21 parts by weight of titanium oxide (manufactured by Ishihara Sangyo Co.: TTO55A) and 39 parts by weight of copolymerized nylon resin (manufactured by Toray Co.: Amilan CM8000) were added to a mixed solvent of 329 parts by weight of methanol and 611 parts by weight of 1,2-dichloroethane, and they were dispersed for 8 hours using a paint shaker to prepare a coating solution for intermediate layer. The obtained coating solution for intermediate layer was filled in a coating tank. A cylindrical aluminum conductive substrate 11 of 40 mm diameter and 340 mm length was dipped in the coating tank and then pulled up and dried to form an intermediate layer 18 of 1.0 μm thickness on the outer peripheral surface of the conductive substrate 11.

Then, 2 parts by weight of oxotitanium phthalocyanine having a crystal structure showing an apparent diffraction peak at least at a Bragg angle of 2θ (error: 2θ±0.2°) of 27.2° in the X-ray diffraction spectrum for Cu-Kα characteristic X-rays (wavelength: 1.54 Å) as the charge generating substance 12, 1 part by weight of polyvinyl butyral resin (manufactured by Sekisui Chemical Industry Co.: S-LEC BX-S)

and 97 parts by weight of methyl ethyl ketone were mixed and dispersed by a paint shaker to prepare a coating solution for charge generating layer. The outer circumferential surface of the previously formed intermediate layer 18 was coated with the obtained coating solution for charge generating layer by a dip coating method, which was the same method for the intermediate layer 18, and it was then dried to form a charge generating layer 15 of 0.4 μm thickness.

Then, 10 parts by weight of Exemplified Enamine Compound No. 61 as the charge transporting substance 13, 18 parts by weight of polycarbonate resin (manufactured by Mitsubishi Engineering Plastics Co.: Eupiron Z200) as the binder resin 17, 1.4 parts by weight (about 5% by weight based on the photosensitive layer) of the hindered phenol compound of Exemplified Compound HP-1 shown in Table 33 as the antioxidant, and 0.004 part by weight of dimethylpolysiloxane (Shin-Etsu Chemical Co., Ltd.: KF-96) were dissolved in 110 parts by weight of tetrahydrofuran to prepare a coating solution for charge transporting layer. The outer circumferential surface of the previously formed charge generating layer 15 was coated with the obtained coating solution of charge transporting layer by a dip coating method, which was the same method for the intermediate layer 18, and it was then dried at 110° C. for one hour to form a charge transporting layer 16 of 23 μm thickness.

As described above, the electrophotographic photoreceptor having a constitution shown in FIG. 2 satisfying the constituent factors of the invention was formed.

Examples 27 and 28

Two kinds of electrophotographic photoreceptors satisfying the constituent factors of the invention were formed in the same manner as in Example 26 except for using Exemplified Compound P-36 shown in Table 42 or Exemplified Compound S-12 shown in Table 46 instead of Exemplified Compound HP-1 as an antioxidant in Example 26.

Examples 29 and 30

Two kinds of electrophotographic photoreceptors satisfying the constituent factors of the invention were formed in the same manner as in Example 26 except for using Exemplified Compound HA-3 shown in Table 47 or Exemplified Compound TZ-4 shown in Table 50 as a light stabilizer instead of Exemplified Compound HP-1 as an antioxidant in Example 26.

Example 31

An electrophotographic photoreceptor satisfying the constituent factors of the invention was formed in the same manner as in Example 26 except for using Exemplified Compound X-19 shown in Table 55 instead of Exemplified Compound HP-1 as an antioxidant in Example 26.

Example 32

An electrophotographic photoreceptor satisfying the constituent factors of the invention was formed in the same manner as in Example 26 except for using Exemplified Compound 159 shown in Table 23 instead of Exemplified Compound No. 61 as the charge transporting substance in Example 26.

Example 33

An electrophotographic photoreceptor satisfying the constituent factors of the invention was formed in the same manner as in Example 26 except for using 1 part by weight of the hindered phenol compound of Exemplified Compound HP-1 and 0.4 part of the hindered amine compound of Exemplified Compound HA-3 shown in Table 47 as a light stabilizer to be used as a mixture (in an amount of about 5% by weight in total based on the photosensitive layer) instead of 1.4 parts by weight of the hindered phenol compound of Exemplified Compound HP-1 as an antioxidant in Example 26.

Example 34

An electrophotographic photoreceptor satisfying the constituent factors of the invention was formed in the same manner as in Example 26 except for using 0.3 part by weight of the hindered phenol compound of Exemplified Compound HP-26 shown in Table 35 as an antioxidant and 0.2 part of the hindered amine compound of Exemplified Compound HA-10 shown in Table 48 as a light stabilizer to be used as a mixture (in an amount of about 2% by weight of content in total based on the photosensitive layer) instead of 1.4 parts by weight of the hindered phenol compound of Exemplified Compound HP-1 as an antioxidant in example 26.

Example 35

An electrophotographic photoreceptor satisfying the constituent factors of the invention was formed in the same manner as in Example 26 except for using 1 part by weight of the hindered phenol compound of Exemplified Compound HP-1 and 1 part of Exemplified Compound X-16 shown in Table 54 as a mixture (about 7% by weight of content in total based on the photosensitive layer) instead of 1.4 parts by weight of the hindered phenol compound of Exemplified Compound HP-1 as an antioxidant in Example 26.

Comparative Example 11

An electrophotographic photoreceptor not satisfying the constituent factors of the invention was formed in the same manner as in Example 26 except for using the hindered phenol compound of Exemplified Compound HP-1 as an antioxidant in Example 26.

<Evaluation 3>

Each of the electrophotographic photoreceptors formed in Examples 26 to 35 and Comparative Example 11 described above were loaded on a commercially available small-sized digital copier (manufactured by Sharp Corp.: AR-C260) modified such that the surface potential of the photoreceptors in the image forming process could be measured with a surface potential meter (manufactured by GEN-TECH Inc.: CATE751). The surface potential of the photoreceptor was measured just after charging as a charge potential $V_0$ (V) under a circumstance at a temperature of 22° C. and a relative humidity of 20% (22° C./20% RH) Further the surface potential of the photoreceptor was measured just after the exposure of a laser light as an after exposure potential $V_L$ (V). The results of the measurement were used as the results of measurement in an initial state.

Then, after conducting actual reproduction aging of copying test images of a predetermined pattern on 10,000 common paper, the charge potential $V_0$ (V) and the after exposure potential $V_L$ (V) were measured in the same manner as in the initial state. The results of the measurement were used as results of the measurement after actual reproduction aging.

Then, half-tone images were formed on JIS (Japan Industrial Standards) A3 common paper. In this case, the half tone images are images in which shading of image was expressed by black and white gradation dots. The obtained images were visually observed, and the image quality was evaluated with respect to the extent of image defects such as blanking, black streaks and image blurring.

The image quality was evaluated with reference to the following scores.
A: Good. No image defects.
B: Somewhat poor. Somewhat negligible image defects.
C: Poor. Distinct image defects.

Table 58 shows the results of measurements in the initial state and those after actual reproduction aging and the result of evaluation for the images after actual reproduction aging.

those of the photoreceptors of Examples 26 to 35 in the initial state, but the absolute value for the charge potential $V_0$ was greatly lowered after the actual reproduction aging and the absolute value for the after exposure potential $V_L$ was increased remarkably. Further, apparent image defects were formed in the images formed by the copying machine mounting the photoreceptor of Comparative Example 11 after actual reproduction aging.

As described above, by the incorporation of the enamine compound represented by the general formula (1) and at least one of the antioxidant and the light stabilizer in combination to the photosensitive layer, it was possible to obtain a highly reliable electrophotographic photoreceptor having high chargeability, sensitivity and light responsivity, not suffering from deterioration of the characteristics described above even when it is used under a low temperature circumstance, stable against an active gas such as ozone or NOx, and UV-rays and heat and with less fatigue deterioration after repetitive use.

The invention may be embodied in other specific forms without departing from the spirit or essential characteristics thereof. The present embodiments are therefore to be considered in all respects as illustrative and not restrictive, the scope

TABLE 58

| | Charge transporting substance | Antioxidant · light stabilizer | Initial stage | | After actual copying and aging | | Evaluation of image quality |
|---|---|---|---|---|---|---|---|
| | | | $V_0(V)$ | $V_L(V)$ | $V_0(V)$ | $V_L(V)$ | |
| Example 26 | Exemplified Compound 61 | HP-1 | −605 | −45 | −602 | −55 | A |
| Example 27 | Exemplified Compound 61 | P-36 | −604 | −48 | −605 | −59 | B |
| Example 28 | Exemplified Compound 61 | S-12 | −600 | −51 | −603 | −65 | B |
| Example 29 | Exemplified Compound 61 | HA-3 | −608 | −46 | −605 | −54 | A |
| Example 30 | Exemplified Compound 61 | TZ-4 | −604 | −49 | −608 | −61 | B |
| Example 31 | Exemplified Compound 61 | X-19 | −602 | −49 | −600 | −61 | B |
| Example 32 | Exemplified Compound 159 | HP-1 | −608 | −45 | −605 | −54 | A |
| Example 33 | Exemplified Compound 61 | HP-1 + HA-3 | −607 | −45 | −601 | −52 | A |
| Example 34 | Exemplified Compound 61 | HP-26 + HA-10 | −608 | −46 | −605 | −53 | A |
| Example 35 | Exemplified Compound 61 | HP-1 + X-16 | −604 | −46 | −604 | −52 | A |
| Comp. Example 11 | Exemplified Compound 61 | None | −602 | −48 | −485 | −115 | C |

From Table 58, it has been found that among the photoreceptors of Examples 26 to 35 and Comparative Example 11 using the enamine compound represented by the general formula (1) for the charge transporting substance 13, the photoreceptors of Examples 26 to 35 containing the antioxidant and the light stabilizer in the photosensitive layer showed no remarkable lowering of the absolute value for the charged potential $V_0$ even after exposure to ozone or Nox during charging, exposure, and actual reproduction aging under load such as exposure to light or heat upon charge elimination and no remarkable increase of the absolute value for the after exposure potential $V_L$ and had excellent electrical characteristics. Further, images formed by a copying machine mounting photoreceptors of Examples 26 to 35 after actual reproduction aging scarcely showed image defects such as image blurring due to the fatigue deterioration and were at a substantially good quality.

On the contrary, the photoreceptor of Comparative Example 11 containing neither the antioxidant nor the light stabilizer in the photosensitive layer showed the same extent of charge potential $V_0$ and the after exposure potential $V_L$ as of the invention being indicated by the appended claims rather than by the foregoing description and all changes which come within the meaning and the range of equivalency of the claims are therefore intended to be embraced therein.

INDUSTRIAL APPLICABILITY

As has been described above, according to the invention, since the photosensitive layer contains an enamine compound of high charge movability having a specified structure and at least one of the antioxidant and the light stabilizer in the photosensitive layer, it is possible to obtain a highly reliable electrophotographic photoreceptor having high chargeability, sensitivity and light responsivity, not suffering from lowering of the characteristics described above even in a case when it is used under a low temperature circumstance or in a high speed electrophotographic process, stable against an active gas such as ozone or NOx, UV-rays and heat, and with less fatigue deterioration after repetitive use. Further, the stability of the coating solution upon forming the photosensitive layer by coating can be increased to improve the stability of quality and the productivity of the electrophotographic photoreceptor.

Further, according to the invention, since the photosensitive layer contains an enamine compound of a specified structure having a particularly high charge movability, and synthesized relatively easily at a high yield and capable of being produced at a reduced cost, it is possible to manufacture an electrophotographic photoreceptor having higher sensitivity and light responsivity at a reduced manufacturing cost.

Further, according to the invention, since the photosensitive layer contains a specified antioxidant, it is possible to particularly suppress the decomposition or degradation of the enamine compound having the specified structure contained as the charge transporting substance in the photosensitive layer to further mitigate the fatigue deterioration upon repetitive use and further improve the durability of the electrophotographic photoreceptor, as well as further increase the stability of the coating solution upon forming the photosensitive layer by coating to further improve the stability of quality and the productivity of the electrophotographic photoreceptor.

Further, according to the invention, since the photosensitive layer contains a specified light stabilizer, it is possible to particularly suppress the decomposition or degradation of the enamine compound having the specified structure contained as the charge transporting substance in the photosensitive layer to further mitigate the fatigue deterioration upon repetitive use and further improve the durability of the electrophotographic photoreceptor, as well as further increase the stability of the coating solution upon forming the photosensitive layer by coating to further improve the stability of quality and the productivity of the electrophotographic photoreceptor.

Further, according to the invention, since the content of the antioxidant contained in the photosensitive layer is selected within a preferred range, this can provide a sufficient effect for the improvement of the durability of the electrophotographic photoreceptor and improvement for the stability of the coating solution, and lowering of the characteristics of the electrophotographic photoreceptor caused by incorporation of the antioxidant can be minimized.

Further, according to the invention, since the content of the light stabilizer contained in the photosensitive layer is selected within a preferred range, can provide a sufficient effect for the improvement of the durability of the electrophotographic photoreceptor and improvement for the stability of the coating solution, and lowering of the characteristics of the electrophotographic photoreceptor caused by incorporation of the light stabilizer can be minimized.

Further, according to the invention, since the image forming apparatus has a highly reliable electrophotographic photoreceptor having high chargeability, sensitivity and light responsivity, not suffering from deterioration of the characteristics described above even in a case where it is used under a low temperature circumstance or in a high speed electrophotographic process or in a case where it is exposed to the light, stable against an active gas such as ozone or NOx and UV-rays and heat, and with less fatigue deterioration upon repetitive use, it is possible to obtain a highly reliable image forming apparatus capable of providing high quality images stably over a long time under various circumstances and with no deterioration of image quality caused by the exposure of the electrophotographic photoreceptor to the light, for example, during maintenance.

The invention claimed is:

1. An electrophotographic photoreceptor comprising:
a conductive substrate composed of a conductive material; and
a photosensitive layer disposed on the conductive substrate and containing an enamine compound represented by the following general formula (1), and a hindered phenol compound having a hindered phenol structural unit as an antioxidant and a light stabilizer selected from the group consisting of HA-3, HA-10 and X-16:

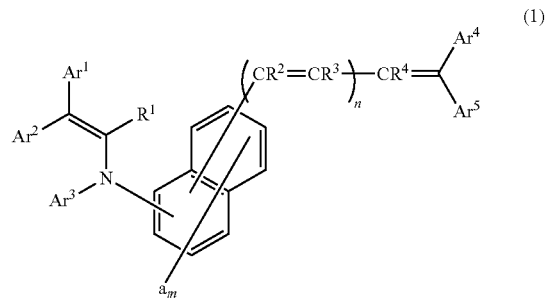

wherein $Ar^1$ and $Ar^2$ each represent an aryl group which may have a substituent or a heterocyclic group which may have a substituent; $Ar^3$ represents an aryl group which may have a substituent, a heterocyclic group which may have a substituent, an aralkyl group which may have a substituent, or an alkyl group which may have a substituent; $Ar^4$ and $Ar^5$ each represent a hydrogen atom, a aryl group which may have a substituent, a heterocyclic group which may have a substituent, an aralkyl group which may have a substituent, or an alkyl group which may have a substituent, but it is excluded that $Ar^4$ and $Ar^5$ are hydrogen atoms at the same time; $Ar^4$ and $Ar^5$ may bond to each other via an atom or an atomic group to form a cyclic structure; "a" represents an alkyl group which may have a substituent, an alkoxy group which may have a substituent, a dialkylamino group which may have a substituent, an aryl group which may have a substituent, a halogen atom, or a hydrogen atom; m indicates an integer of from 1 to 6; when m is 2 or more, then the "a"s may be the same or different and may bond to each other to form a cyclic structure; $R^1$ represents a hydrogen atom, a halogen atom, or an alkyl group which may have a substituent; $R^2$, $R^3$ and $R^4$ each represent a hydrogen atom, an alkyl group which may have a substituent, an aryl group which may have a substituent, a heterocyclic group which may have a substituent, or an aralkyl group which may have a substituent; n indicates an integer of from 0 to 3; when n is 2 or 3, then the $R^2$s may be the same or different and the $R^3$s may be the same or different, but when n is 0, $Ar^3$ is a heterocyclic group which may have a substituent, said HA-3, HA-10 and X-16 having the following structures:

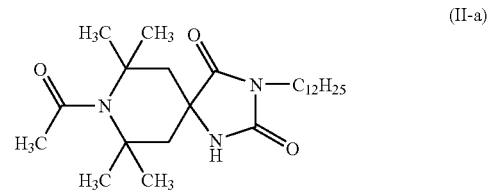

(II-a)

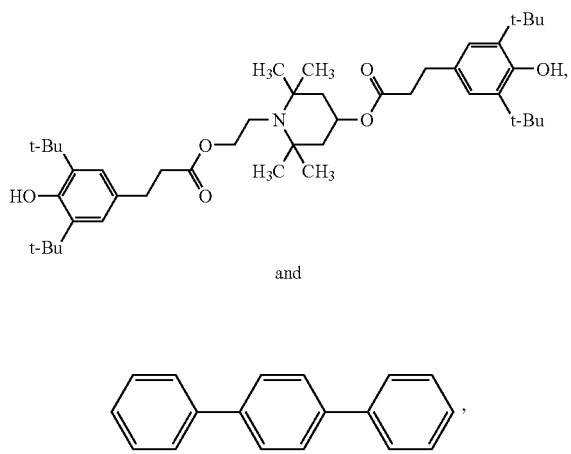

and

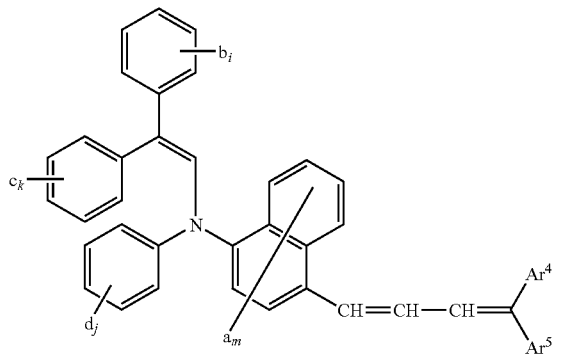

respectively.

2. The electrophotographic photoreceptor of claim 1, wherein the enamine compound represented by the general formula (1) is an enamine compound represented by the following general formula (2):

(2)

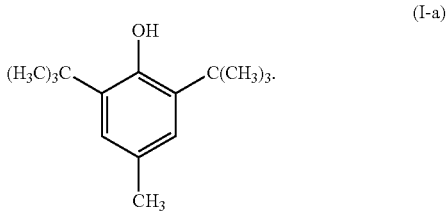

wherein "b", "c" and "d" each represent an alkyl group which may have a substituent, an alkoxy group which may have a substituent, a dialkylamino group which may have a substituent, an aryl group which may have a substituent, a halogen atom, or a hydrogen atom; "i", "k" and "j" each indicate an integer of from 1 to 5; when "i" is 2 or more, then the "b"s may be the same or different and may bond to each other to form a cyclic structure; when "k" is 2 or more, then the "c"s may be the same or different and may bond to each other to form a cyclic structure; and when "j" is 2 or more, then the "d"s may be the same or different and may bond to each other to form a cyclic structure; $Ar^4$, $Ar^5$, "a" and "m" represent the same as those defined in formula (1).

3. The electrophotographic photoreceptor of claim 1, wherein the enamine compound represented by the general formula (1) is an enamine compound represented by the following general formula (1 a):

(1a)

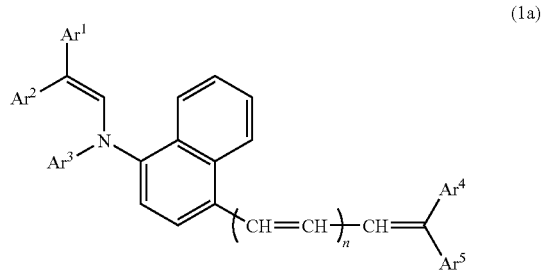

wherein $Ar^1$ and $Ar^2$ each represents a phenyl group; $Ar^3$ represents a tolyl group, p-methoxyphenyl group, naphthyl group, or 5-methyl-2-thienyl group; $Ar^4$ represents a hydrogen atom, lower alkyl group or phenyl group; $Ar^5$ represents a phenyl group or p-methoxyphenyl group; and n represents an integer of 1 to 2.

4. The electrophotographic photoreceptor of claim 1, wherein the hindered phenol compound is a compound represented by the following structural formula (I-a):

(I-a)

$(H_3C)_3C$ — [phenol ring with OH, two $C(CH_3)_3$ groups and $CH_3$] — $C(CH_3)_3$ 5. The electrophotographic photoreceptor of any one of claims 1-3 and 4, wherein the photosensitive layer contains 0.1 to 15% by weight of the antioxidant.

6. The electrophotographic photoreceptor of any one of claims 1-3 and 4, wherein the photosensitive layer contains 0.1 to 10% by weight of the light stabilizer.

7. An image forming apparatus comprising:
the electrophotographic photoreceptor of any one of claims 1-3 and 4;
charging means for charging the electrophotographic photoreceptor;
exposure means for applying exposure to the charged electrophotographic photoreceptor; and
developing means for developing electrostatic latent images formed by exposure.

* * * * *